US009102636B2

(12) United States Patent
Mannion et al.

(10) Patent No.: US 9,102,636 B2
(45) Date of Patent: Aug. 11, 2015

(54) ANALGESIC COMPOUNDS, COMPOSITIONS, AND USES THEREOF

(75) Inventors: James C. Mannion, Plainsboro, NJ (US); Scott L. Dax, Landenberg, PA (US)

(73) Assignee: Galleon Pharmaceuticals, Inc., Horsham, PA (US)

( * ) Notice: Subject to any disclaimer, the term of this patent is extended or adjusted under 35 U.S.C. 154(b) by 1014 days.

(21) Appl. No.: 13/043,159

(22) Filed: Mar. 8, 2011

(65) Prior Publication Data

US 2011/0224269 A1   Sep. 15, 2011
US 2012/0202860 A2   Aug. 9, 2012

Related U.S. Application Data

(60) Provisional application No. 61/312,482, filed on Mar. 10, 2010, provisional application No. 61/378,781, filed on Aug. 31, 2010.

(51) Int. Cl.
*C07D 277/18*   (2006.01)

(52) U.S. Cl.
CPC .................................. *C07D 277/18* (2013.01)

(58) Field of Classification Search
USPC ................................................. 548/190, 194
See application file for complete search history.

(56) References Cited

U.S. PATENT DOCUMENTS 3,993,766 A  * 11/1976 Behner et al. ................. 514/370
2010/0324096 A1 * 12/2010 Hanyu et al. ................. 514/342

FOREIGN PATENT DOCUMENTS

WO   WO-2006/131737 A2 * 12/2006
WO   WO-2009/099195 A1 *  8/2009

OTHER PUBLICATIONS

Chemical Abstracts Registry No. 524705-05-3, indexed in the Registry file on STN Jun. 3, 2003.*
Madayag, et al., "Repeated N-Acetylcysteine Administration Alters Plasticity-Dependent Effects of Cocaine," *The Journal of Neuroscience*, Dec. 19, 2007, 27(51):13968-13976.
Zhou, et al., "N-Acetylcysteine Reduces Extinction Responding and Induces Enduring Reductions in Cue- and Heroin-Induced Drug-Seeking," *Biol Psychiatry*, 2008, 63:338-340.
Ng, et al., "Oxidative stress in psychiatric disorders: evidence base and therapeutic implications," *International Journal of Neuropsychopharmacology*, 2008, 11:851-876.
Bhardwaj, et al., "A Randomized Controlled Trial of Antioxidant Supplementation for Pain Relief in Patients with Chronic Pancreatitis," *Gastroenterology*, 2009, 136:149-159.
Choi, et al., "The Structure-Activity Relationship of Flavonoids as Scavengers of Peroxynitrite," *Phytotherapy Research*, 2002, 16:232-235.
Olmos, et al., "Drugs Modulating the Biological Effects of Peroxynitrite and Related Nitrogen Species," *Medicinal Research Reviews*, 2007, 27(1):1-64.
Muscoli, et al., "Therapeutic manipulation of peroxynitrite attenuates the development of opiate-induced antinociceptive tolerance in mice," *The Journal of Clinical Investigation*, Nov. 2007, 117(11):3530-3539.
Bryant, et al., "Spinal ceramide and neuronal apoptosis in morphine antinociceptive tolerance," *Neuroscience Letters*, 2009, 463:49-53.
Lam, et al., "Analgesic and anti-arthritic effects of Lingzhi and San Miao San supplementation in a rat model of arthritis induced by Freund's complete adjuvant," *Journal of Ethnopharmacology*, 2008, 120:44-50.
Sindrup, et al., "Efficacy of pharmacological treatments of neuropathic pain: an update and effect related to mechanism of drug action," *Pain*, 1999, 83:389-400.
Kim, et al., "An experimental model for peripheral neuropathy produced by segmental spinal nerve ligation in the rat," *Pain*, 1992, 50:355-363.
Jumbelic, "Deaths with Transdermal Fentanyl Patches," *Am J Forensic Med Pathol*, Mar. 2010, 31(1):18-21.
Hargreaves, et al., "A new and sensitive method for measuring thermal nociception in cutaneous hyperalgesia," *Pain*, 1988, 32:77-88.
Whiteside, et al., "The Role of Central and Peripheral μ Opioid Receptors in Inflammatory Pain and Edema: A Study Using Morphine and DiPOA ([8-(3,3-Diphenyl-propyl)-4-oxo-1-phenyl-1,3,8-triaza-spiro[4.5]dec-3-yl]-acetic Acid)," *The Journal of Pharmacology and Experimental Therapeutics*, 2005, 314(3):1234-1240.

* cited by examiner

*Primary Examiner* — Laura L. Stockton
(74) *Attorney, Agent, or Firm* — Saul Ewing LLP; Kathryn Doyle; Domingos J. Silva

(57) ABSTRACT

The invention relates to compounds, compositions, and methods for diminishing pain in a subject in need thereof comprising administering the compounds and compositions herein described.

3 Claims, 31 Drawing Sheets

Compound 2 = 25 mg/kg, IV, Indomethacin = 15 mg/kg, IV, n=6/group
*p<0.05, p<0.01, *p<0.001, compared to the vehicle time-point on the same day Compound 2 = 25 mg/kg, IV, Indomethacin = 15 mg/kg, IV, n=6/group
*p<0.05 compared to vehicle time-point on the same day

ANALGESIC COMPOUNDS, COMPOSITIONS, AND USES THEREOF

CROSS REFERENCE TO RELATED APPLICATIONS

The present application is entitled to priority under 35 U.S.C. §119(e) to U.S. Provisional Applications No. 61/312,482, filed Mar. 10, 2010 and No. 61/378,781, filed Aug. 31, 2010, which applications are hereby incorporated by reference herein in their entireties.

BACKGROUND OF THE INVENTION

Pain is defined as an unpleasant sensory and emotional experience. However, pain can be informative and useful. For example, nociceptive pain is often indicative of injury (e.g., tissue damage) and such pain typically evokes escape or protective behaviors in animals or in a human in order to remove itself, or protect itself, from further exposure to the insult. However, inflammation, cellular and neuronal damage and other processes resulting from injury or disease can lead to states of chronic pathological pain and enhanced sensitivity called hyperalgesia, in which the perception of pain is exaggerated. In such cases, there is a need for new compounds, new methods and new inventions that treat pain and hyperalgesia.

In some cases, such as surgical procedures, the diminution or abolishment of nociceptive pain may be desired and the application of analgesia may be employed. A variety of compounds and medicines are known to be effective in alleviating nociceptive pain and some are analgesic such as opioids.

Post surgically, pain arising from the procedure, for example such as pain at or near the site of an incision, is common. In such cases, there is a desire to alleviate pain and thus there is a need for new compounds, new methods and new inventions that treat post-surgical and incisional pain.

The administration of opioids to treat pain is a well recognized and commonly employed therapy in medicine. Unfortunately, tolerance to opioids (tachyphylaxis) and opioid-induced hyperalgesia can often result during the course of therapy. In such patients, increasingly higher doses of opioids are needed to provide an acceptable level of pain relief. Administering these higher does, though, can cause adverse side effects implicating the safety concerns associated with opioids. Side effects associated with opioid administration may include respiratory depression, constipation, nausea, and vomiting. Safety concerns include the possibility of developing dependence, suffering withdrawal upon discontinuation of treatment, and the potential for abuse. Tachyphylaxis is a phenomenon in which the repeated administration of a drug, such as a narcotic analgesic, results in a rapidly appearing and marked decrease in the effectiveness of that drug. In opioid-induced hyperalgesia, prolonged administration of opioids also results in a paradoxical increase in pain, or a hypersensitivity to a stimulus that is thought to be unrelated to the original injury or insult. Opioid-induced tachyphylaxis and opioid-induced hyperalgesia have been well documented in animal models of nociception as well as in human clinical trials. These phenomena present significant clinical challenges for the treatment of pain and therefore new compounds, new methods and new inventions to treat pain and/or to alleviate hyperalgesia and tolerance are needed.

Reactive oxygen species (ROS) and reactive nitrogen species (RNS) are highly reactive small molecules that include, for example, oxygen ions and free radicals such as peroxide, hydroxyl radical and other species such as peroxynitrite (OONO$^-$). Peroxynitrite is the product of the interaction between superoxide (O$_2^-$) and nitric oxide (NO). In cells, ROS and RNS form normally, as a by-product of normal metabolism, but they also play an important role in the pathogenesis of many disorders, including those affecting the lung, the central nervous system and skeletal muscle. In addition, during times of stress (such as, for example, hypoxia) ROS and/or RNS levels can increase significantly, which can lead to damage to cell components.

Peroxynitrite activity has been implicated in the development of opiate-induced antinociceptive (pain) tolerance (tachyphylaxis) (Muscoli et al., 2007, J Clin Invest 117:3530-3539). In 2007, Muscoli proposed that peroxynitrite formation is a key pathway in the development of narcotic analgesic tachyphylaxis. Previous attempts at reducing the damaging effects of peroxynitrite have been focused on flavonoids and simpler phenols, some of which have proven to be ineffective or toxic when administered to animals and man (Olmos et al., 2007, Med Res Rev 27:1-64; Choi et al., 2002, Phytother Res 16:232-235). Thus, collectively there exists a need for new compounds, new methods and new inventions that decrease the level or activity of reactive oxygen/nitrogen species, such as peroxynitrite.

Thus, there exists a need for compounds, compositions, and methods for preserving or extending opioid analgesia without opioid dose-escalation. Similarly, there exists a need for compounds, compositions, and methods that are dose-sparing with respect to opioid therapy. The current invention fulfills these needs.

BRIEF SUMMARY OF INVENTION

The invention includes a compound according to Formula I or a salt thereof

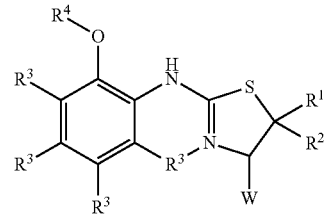

Formula I wherein:

$R^1$ and $R^2$ are, independently, hydrogen or alkyl, or $R^1$ and $R^2$ form together, a radical according to the formula $(CH_2)_n$, wherein 2≤n≤6;

$R^3$ is, independently at each occurrence, hydrogen, alkyl, substituted alkyl, alkenyl, alkynyl, halogen, phenyl, substituted phenyl, aryl, substituted aryl, heteroaryl, substituted heteroaryl, hydroxyl, alkoxy, cyano, nitro, acyl, carboxy, carboxyalkyl, or amido;

$R^4$ is hydrogen, alkyl, substituted alkyl, or acyl; and

W is hydrogen, alkyl, aryl, substituted aryl, heteroaryl, substituted heteroaryl, carboxy, or carboxyalkyl.

In one embodiment, $R^1$ and $R^2$ are $CH_3$. In another embodiment, the compound according to Formula I is selected from the group consisting of (S)-2-(2-hydroxyphenylamino)-thiazoline-5,5-dimethyl-4-carboxylic acid, (R)-2-(2-hydroxyphenylamino)-thiazoline-5,5-dimethyl-4-carboxylic acid, (R)-2-(2-Hydroxy-4-methoxyphenylamino)-thiazoline-4-carboxylic acid, (R)-2-(4-Fluoro-2-hydroxyphenylamino)-thiazoline-4-carboxylic acid, (R)-2-(3,5-Dichloro-2-hydroxy-4-methylphenylamino)-thiazoline-4-carboxylic acid, (R)-2-(5-tert-Butyl-2-hydroxyphenylamino)-thiazoline-4-carboxylic acid, (R)-2-(2-Hydroxy-4-methoxycarbonylphenylamino)-thiazoline-4-carboxylic acid, (R)-2-(5-Ethanesulfonyl-2-hydroxy-phenylamino)-thiazoline-4-carboxylic acid, (R)-2-(4-Chloro-2-hydroxyphenylamino)-thiazoline-4- carboxylic acid, (R)-2-(2-Hydroxy-5-methoxyphenylamino)-thiazoline-4-carboxylic acid, (S)-2-(2-Hydroxy-5-chlorophenylamino)-thiazoline-5,5-dimethyl-4-carboxylic acid methyl ester, (S)-2-(2-Hydroxy-5-chlorophenylamino)-thiazoline-5,5-dimethyl-4-carboxylic acid, (S)-2-(2-Hydroxy-5-methylphenylamino)-thiazoline-5,5-dimethyl-4-carboxylic acid methyl ester, (S)-2-(2-Hydroxy-5-methylphenylamino)-thiazoline-5,5-dimethyl-4-carboxylic acid, (S)-2-(2-Hydroxy-4-methoxyphenylamino)-thiazoline-5,5-dimethyl-4-carboxylic acid, (S)-2-(2-Hydroxy-4-methoxyphenylamino)-thiazoline-5,5-dimethyl-4-carboxylic acid methyl ester, (S)-2-(4-Chloro-2-hydroxyphenylamino)-thiazoline-5,5-dimethyl-4-carboxylic acid, (S)-2-(2-Hydroxy-5-nitrophenylamino)-thiazoline-5,5-dimethyl-4-carboxylic acid methyl ester, (S)-2-(2-Hydroxy-5-nitrophenylamino)-thiazoline-5,5-dimethyl-4-carboxylic acid, (S)-2-(5-Ethanesulfonyl-2-hydroxyphenylamino)-thiazoline-5,5-dimethyl-4-carboxylic acid methyl ester, (S)-2-(5-Ethanesulfonyl-2-hydroxyphenylamino)-thiazoline-5,5-dimethyl-4-carboxylic acid, (R)-2-(2-hydroxyphenylamino)-thiazoline-4-carboxylic acid methyl ester, (S)-2-(2-hydroxyphenylamino)-thiazoline-5,5-dimethyl-4-carboxylic acid methyl ester, (R)-2-(4-chloro-2-hydroxyphenylamino)-thiazoline-4-carboxylic acid methyl ester, (S)-2-(4-chloro-2-hydroxyphenylamino)-thiazoline-5,5-dimethyl-4-carboxylic acid methyl ester, (R)-2-(4-chloro-2-hydroxyphenylamino)-thiazoline-4-carboxylic acid, and (R)-2-(2-hydroxyphenylamino)-thiazoline-5,5-dimethyl-4-carboxylic acid methyl ester, mixtures thereof and salts thereof.

The invention also includes a method of making a compound according to Formula I, or a salt thereof. The method comprises: reacting a compound according to formula A:

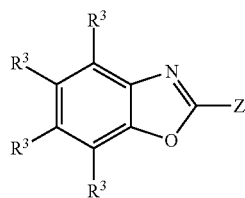

with a compound according to formula C:

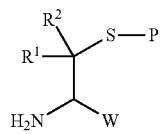

to give a compound according to formula D:

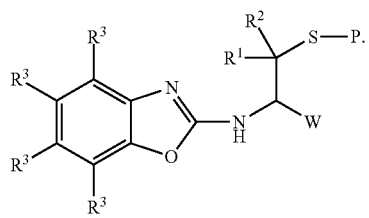

The method further comprises deprotecting the compound according to formula D to give the compound according to Formula I or a salt thereof;
wherein
$R^1$ and $R^2$ are, independently, hydrogen or alkyl, or $R^1$ and $R^2$ form together a radical according to the formula $(CH_2)_n$, wherein $2 \leq n \leq 6$;

$R^3$ is, independently at each occurrence, hydrogen, alkyl, substituted alkyl, alkenyl, alkynyl, halogen, phenyl, substituted phenyl, aryl, substituted aryl, heteroaryl, substituted heteroaryl, hydroxyl, alkoxy, cyano, nitro, acyl, carboxy, carboxyalkyl, or amido;

$R^4$ is hydrogen, alkyl, substituted alkyl, or acyl;

W is hydrogen, alkyl, aryl, substituted aryl, heteroaryl, substituted heteroaryl, carboxy, or carboxyalkyl;

Z is Cl, Br, or I; and

P is a thiol protecting group.

The invention further includes a method of making a compound according to Formula I. The method comprises reacting a compound according to formula A or a salt thereof:

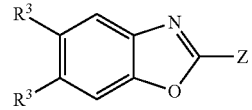

with a compound according to formula B:

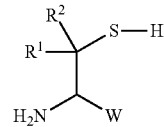

to give the compound according to Formula I or a salt thereof;
wherein
$R^1$ and $R^2$ are, independently, hydrogen or alkyl, or $R^1$ and $R^2$ form together a radical according to the formula $(CH_2)_n$, wherein $2 \leq n \leq 6$;

$R^3$ is, independently at each occurrence, hydrogen, alkyl, substituted alkyl, alkenyl, alkynyl, halogen, phenyl, substituted phenyl, aryl, substituted aryl, heteroaryl, substituted heteroaryl, hydroxyl, alkoxy, cyano, nitro, acyl, carboxy, carboxyalkyl, or amido;

$R^4$ is hydrogen, alkyl, substituted alkyl, or acyl;

W is hydrogen, alkyl, aryl, substituted aryl, heteroaryl, substituted heteroaryl, carboxy, or carboxyalkyl; and Z is Cl, Br, or I.

The invention further includes a method of diminishing the dosage of a narcotic analgesic required to achieve pain relief in a subject in need thereof, the method comprising the step of administering to the subject a therapeutically effective amount of at least one compound according to Formula I or a salt thereof, Formula I

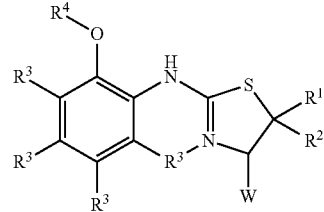

wherein:
$R^1$ and $R^2$ are, independently, hydrogen or alkyl, or $R^1$ and $R^2$ form together a radical according to the formula $(CH_2)_n$, wherein $2 \leq n \leq 6$;

$R^3$ is, independently at each occurrence, hydrogen, alkyl, substituted alkyl, alkenyl, alkynyl, halogen, phenyl, substituted phenyl, aryl, substituted aryl, heteroaryl, substituted heteroaryl, hydroxyl, alkoxy, cyano, nitro, acyl, carboxy, carboxyalkyl, or amido;

$R^4$ is hydrogen, alkyl, substituted alkyl, or acyl; and

W is hydrogen, alkyl, aryl, substituted aryl, heteroaryl, substituted heteroaryl, carboxy, or carboxyalky.
whereby the dosage of the narcotic analgesic required to achieve pain relief in the subject
diminished.

In one embodiment, the compound is administered in a therapeutic dosing regimen or a preconditioning dosing regimen. In another embodiment, the subject is a human.

The invention further includes a method of extending the duration of action or analgesic efficacy of a narcotic analgesic in a subject in need thereof, the method comprising the step of administering to the subject a therapeutically effective amount of at least one compound according to Formula I or a salt thereof,

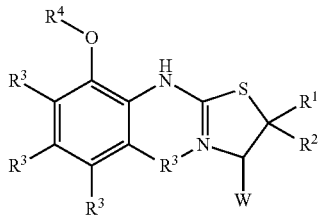

Formula I wherein:
$R^1$ and $R^2$ are, independently, hydrogen or alkyl, or $R^1$ and $R^2$ form together a radical according to the formula $(CH_2)_n$, wherein $2 \le n \le 6$;
$R^3$ is, independently at each occurrence, hydrogen, alkyl, substituted alkyl, alkenyl, alkynyl, halogen, phenyl, substituted phenyl, aryl, substituted aryl, heteroaryl, substituted heteroaryl, hydroxyl, alkoxy, cyano, nitro, acyl, carboxy, carboxyalkyl, or amido;
$R^4$ is hydrogen, alkyl, substituted alkyl, or acyl; and
W is hydrogen, alkyl, aryl, substituted aryl, heteroaryl, substituted heteroaryl, carboxy, or carboxyalky.
whereby the duration of action or analgesic efficacy of the narcotic analgesic in the subject is extended.

In one embodiment, the compound is administered in a therapeutic dosing regimen or a preconditioning dosing regimen. In another embodiment, the subject is a human.

The invention further includes a method of preventing tachyphylaxis in a subject in need thereof, the method comprising the step of administering to the subject a therapeutically effective amount of at least one compound according to Formula I or a salt thereof,

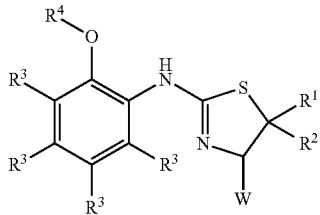

Formula I wherein:
$R^1$ and $R^2$ are, independently, hydrogen or alkyl, or are together a radical according to the formula $(CH_2)_n$, wherein $2 \le n \le 6$;
$R^3$ is, independently at each occurrence, hydrogen, alkyl, substituted alkyl, alkenyl, alkynyl, halogen, phenyl, substituted phenyl, aryl, substituted aryl, heteroaryl, substituted heteroaryl, hydroxyl, alkoxy, cyano, nitro, acyl, carboxy, carboxyalkyl, or amido;
$R^4$ is hydrogen, alkyl, substituted alkyl, or acyl;
W is hydrogen, alkyl, aryl, substituted aryl, heteroaryl, substituted heteroaryl, carboxy, or carboxyalkyl.
whereby tachyphylaxis in the subject is prevented.

In one embodiment, the compound is administered in a therapeutic dosing regimen or a preconditioning dosing regimen. In another embodiment, the subject is a human.

The invention further includes a method of reducing the level of activity of reactive oxygen species and reactive nitrogen species in a subject in need thereof, the method comprising the step of administering to the subject a therapeutically effective amount of at least one compound according to Formula I or a salt thereof,

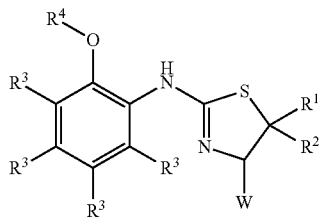

Formula I wherein:
$R^1$ and $R^2$ are, independently, hydrogen or alkyl, or $R^1$ and $R^2$ form together a radical according to the formula $(CH_2)_n$, wherein $2 \le n \le 6$;
$R^3$ is, independently at each occurrence, hydrogen, alkyl, substituted alkyl, alkenyl, alkynyl, halogen, phenyl, substituted phenyl, aryl, substituted aryl, heteroaryl, substituted heteroaryl, hydroxyl, alkoxy, cyano, nitro, acyl, carboxy, carboxyalkyl, or amido;
$R^4$ is hydrogen, alkyl, substituted alkyl, or acyl; and
W is hydrogen, alkyl, aryl, substituted aryl, heteroaryl, substituted heteroaryl, carboxy, or carboxyalkyl.
whereby the level of activity of reactive oxygen species and reactive nitrogen species in the subject is reduced.

In one embodiment, the reactive oxygen species is peroxynitrite. In another embodiment, the subject exhibits symptoms of at least one disorder from the group consisting of: stroke, myocardial infarction, chronic heart failure, circulatory shock, chronic inflammatory diseases, cancer, neurogenerative disorders, sleep apnea, diabetes, narcotic analgesic tachyphylaxis, pancreatitis pain, addictive behavior, and hypertension. Yet in another embodiment, the compound is administered in a therapeutic dosing regimen or a preconditioning dosing regimen. Yet in another embodiment, the level of activity of reactive oxygen species is reduced by diminishing reactive oxygen species production. Yet in another embodiment, the subject is a human.

BRIEF DESCRIPTION OF THE DRAWINGS

The following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings. In the drawings:

FIG. 9A and FIG. 9B, depicts the results of an example experiment demonstrating that compound 2 inhibits the development of hyperalgesia following incisional surgery.

FIG. 10A and FIG. 10B, depicts the results of an example experiment demonstrating that compound 2 reverses hyperalgesia following incisional surgery.

FIG. 18A and FIG. 18B, illustrates the effect of preemptively dosed 25 mg/kg Compound 2 i.v. on FCA induced thermal hyperalgesia and tactile allodynia.

FIG. 19A and FIG. 19B, illustrates the effect of 3-100 mg/kg Compound 2 p.o. on FCA tactile allodynia when dosed 24-72 hours post-FCA FIG. 20, comprising

FIG. 21A and FIG. 21B, illustrates the effect of 10 and 30 mg/kg Compound 2 p.o. on carrageenan-induced thermal hyperalgesia and edema when dosed curatively.

FIG. 22A and FIG. 22B, illustrates the effect of 10 and 30 mg/kg Compound 2 p.o. on carrageenan-induced thermal hyperalgesia and edema when dosed preemptively.

DETAILED DESCRIPTION OF THE INVENTION

Figure 1:
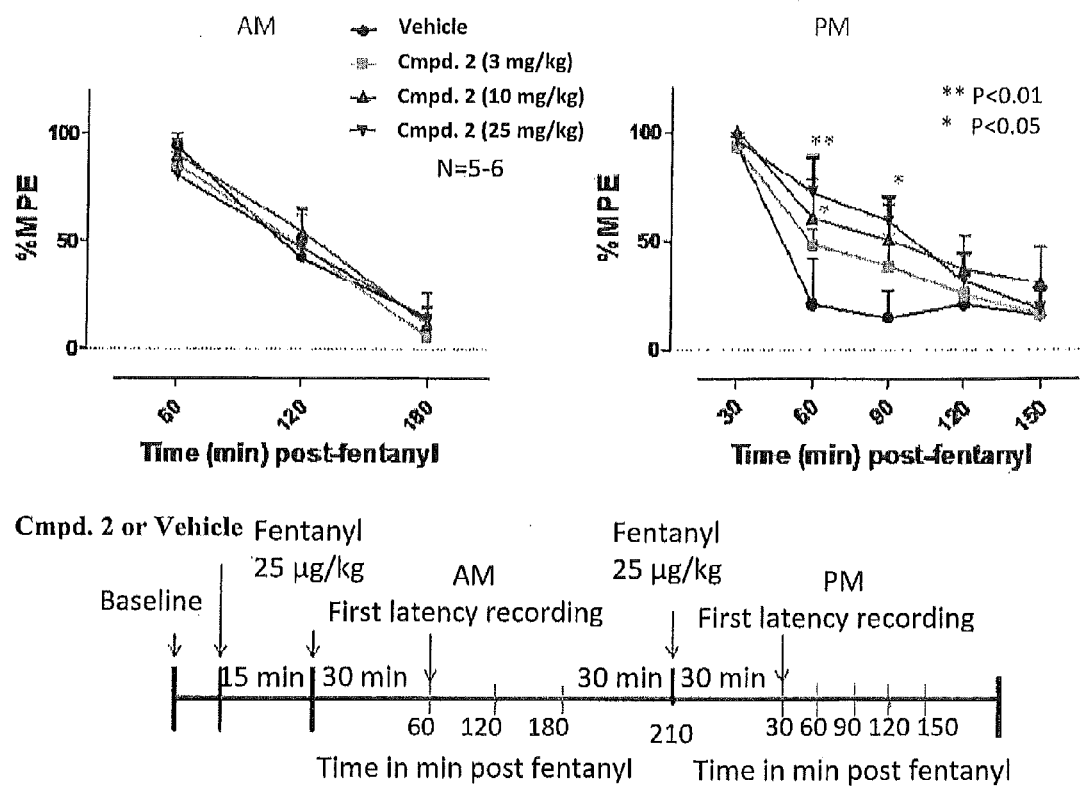
FIG. 1 depicts the results of an example experiment demonstrating that compound 2 dose-dependently preserves fentanyl analgesia in rat tail flick model.

The invention relates to compounds, compositions, and methods for diminishing pain in a subject in need thereof. In one embodiment, the invention is a compound according to Formula I:

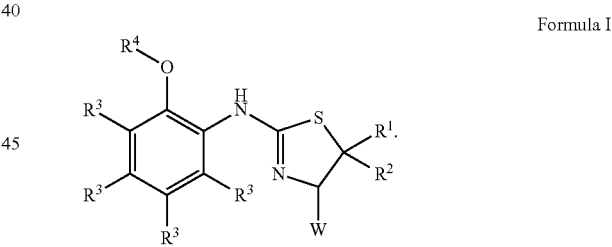

Formula I

In another embodiment, the invention relates to a composition comprising a compound according to formula I. In another embodiment, the invention is a method of administering a compound and/or composition of the invention to provide analgesia. In various embodiments, the invention relates to compounds, compositions, and methods for reducing or abolishing incisional pain in a subject in need thereof. The invention also provides methods for reducing or abolishing hyperalgesia in a subject in need thereof. It is also an aspect of the invention that the compounds and/or compositions disclosed herein can be administered to a subject to reduce, prevent or reverse hyperalgesia occurring in response to the administration of a drug, such as a narcotic analgesic.

In one aspect, the invention is a compound and/or composition that leads to an increase in the duration of action of narcotic analgesic agents such as, for example, fentanyl or morphine. In another aspect, the invention is a method that leads to an increase in the duration of action of narcotic analgesic agents, such as fentanyl or morphine.

In another embodiment, the invention is a compound and/or composition that diminishes the effective dosage of a narcotic analgesic agent such as, for example, fentanyl or morphine. In still another embodiment, the invention is a method that leads to a decrease in the effective dosage of a narcotic analgesic agent, such as fentanyl or morphine. A decrease in the effective dosage means that, when administered in conjunction with the compounds, compositions, or methods of the invention, a lower dosage of a narcotic analgesic is sufficient to achieve the same level of analgesia as compared with when the analgesic agent is administered alone.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent on the context in which it is used.

As used herein, the term "modulate" is meant to refer to any change in biological state, i.e. increasing, decreasing, and the like.

As used herein, a "therapeutically effective amount" is the amount of a therapeutic composition sufficient to provide a beneficial effect to a subject to which the composition is administered.

The terms "inhibiting," "reducing," "preventing," or "diminishing," and variations of these terms, as used herein include any measurable decrease, including complete or substantially complete inhibition.

The term "or," as used herein, means "and/or" unless explicitly indicated to refer to alternatives only or the alternatives are mutually exclusive, although the disclosure supports a definition that refers to only alternatives and "and/or."

The term "treat" or "treatment," as used herein, refers to the alleviation (i.e., "diminution") and/or the elimination of a sign/symptom or a source of a sign/symptom. By way of several non-limiting examples, a disorder can be treated by alleviating a sign/symptom of a disorder. A sign/symptom of a disorder can also be treated by altogether eliminating a sign/symptom of the disorder.

The phrase "therapeutic dosing regimen" as used herein, means to administer a compound of the invention to a subject, at time when the subject is experiencing a disorder as elsewhere described herein, in a manner, including dosage, timing of doses, and frequency of doses, so as to produce a beneficial consequence in the subject, such as treatment of a disorder, or a symptom of a disorder, in the subject.

The phrase "preconditioning dosing regimen" as used herein, means to administer a compound of the invention to a subject, at a time before the subject is experiencing a disorder as elsewhere described herein, in a manner, including dosage, timing of doses, and frequency of doses, so as to produce a beneficial consequence in the subject, such as treatment of a disorder, or a symptom of a disorder, in the subject.

The term "subject," as used herein, refers to a mammal, including dogs, cats, pigs, cows, sheep, goats, horses, rats, and mice and humans. Preferably the subject is a human.

As used herein, a "decrease in the effective dosage" means that, when administered in conjunction with the compositions or methods of the invention, a lower overall dosage of a narcotic analgesic, over time, is sufficient to achieve the same level of analgesia as compared with when the analgesic agent is administered alone.

Description

Tachyphylaxis is a phenomenon in which the repeated administration of a drug, such as a narcotic analgesic, results in a rapidly appearing and marked decrease in the effectiveness of that drug. It is a further aspect of the invention that the compounds and/or compositions described herein can be administered to a subject to reduce, prevent or reverse tachyphylaxis occurring in response to the administration of a drug, such as a narcotic analgesic.

Narcotic analgesics are known to cause respiratory depression. The compounds, compositions, and methods of the invention can be used to prevent a loss of normal breathing, or to restore normal breathing after a loss occurs. One non-limiting example of a loss of normal breathing is respiratory depression. Respiratory depression results in hypoventilation, which further results in hypoxia. A primary initial clinical manifestation of hypoxia is drowsiness or excessive daytime sleepiness. Accordingly, drugs that cause decreased respiratory drive and the resulting hypoxia are sometimes limited in their usefulness due to the fear of a life-threatening respiratory depression and/or the excessive daytime sleepiness that negatively impacts quality of life.

There are a wide variety of disorders that have loss of normal breathing or respiratory depression as a primary or secondary feature of the disorder, which can be treated using the compounds, compositions, and methods of the present invention. Examples of a primary loss of normal breathing include: apneas (central, mixed and obstructive) and congenital central hypoventilation syndrome. Secondary loss of normal breathing may be due to certain drugs (e.g., anesthetics, sedatives, anxiolytics, hypnotics, alcohol, opioid analgesics), chronic cardio-pulmonary diseases (e.g., heart failure, chronic bronchitis, emphysema, and impending respiratory failure), excessive weight (e.g., obesity-hypoventilation syndrome) and/or factors that affect the neurological system (e.g., stroke, tumor, trauma, radiation damage, ALS).

Generally, patients in need of analgesia or anesthesia may receive one agent, or a combination of multiple agents, to create a state of partial or full unconsciousness to allow for medical procedures, such as surgery, to be performed. A common undesirable action of many agents used for analgesia and anesthesia (e.g., opioid analgesics, barbiturates, benzodiazepines, inhaled anesthetics, propofol) is respiratory depression. Examples of opioid analgesics include morphine, codeine, fentanyl, buprenorphine, meperidine, methadone, sufentanil, alfentanil, and the like. Examples of barbiturates include allobarbital, alphenal, amobarbital, aprobarbital, barbexaclone, barbital, brallobarbital, butabarbital, butalbital, butobarbital, butallylonal, crotylbarbital, cyclobarbital, cyclopal, ethallobarbital, febarbamate, heptabarbital, hexethal, hexobarbital, mephobarbital, metharbital, methohexital, methylphenobarbital, narcobarbital, nealbarbital, pentobarbital, phenobarbital, probarbital, propallylonal, proxibarbal, proxibarbital, reposal, secbutabarbital, secobarbital, sigmodal, talbutal, thialbarbital, thiamylal, thiobarbital, thiobutabarbital, thiopental, valofane, vinbarbital, and vinylbital. Examples of benzodiazepines include midazolam, clonazepam, diazepam, alprazolam and the like. Examples of inhaled anesthetics included halothane, enflurane, isoflurane, sevoflurane, desflurane, and the like. Not only can the respiratory depressant effect occur soon after administration of the agent, but the effects of the anesthetic and/or analgesic agent can linger for hours or days after the procedure. The compounds, compositions, and methods of the invention can be used to diminish, prevent or reverse drug-induced respiratory depression.

In one embodiment of the invention the compounds and/or compositions disclosed herein diminish the level of, or inhibit the activity of, ROS or RNS (such as, by way of example only, peroxynitrite). In another embodiment, the invention includes a compound and/or composition that diminishes the level or inhibits the activity of ROS and RNS, such as peroxynitrite, which leads to an increase in the duration of action of a narcotic analgesic agent, such as, by way of non-limiting examples, fentanyl and morphine. In another embodiment, the invention includes a compound and/or composition that diminishes the level or inhibits the activity of ROS and RNS, such as, by way of non-limiting example, peroxynitrite, which contributes to a decrease in the effective dosage of a narcotic analgesic agent such as, by way of non-limiting examples, fentanyl and morphine. In still another embodiment, the invention is a method of diminishing the level or activity of ROS and RNS, such as, by way of non-limiting example, peroxynitrite, which leads to a decrease in the effective dosage of a narcotic analgesic agent, such as, by way of non-limiting examples, fentanyl or morphine.

The therapeutic uses of the compounds, compositions, and methods of the invention include, but are not limited to, combating the effects of ROS and RNS, such as, by way of non-limiting example, peroxynitrite. Potential disease targets are extensive and include, but are not limited to; stroke, myocardial infarction, chronic heart failure, circulatory shock, chronic inflammatory diseases, cancer, neurogenerative disorders, sleep apnea, diabetes, narcotic analgesic tachyphylaxis, pancreatitis pain, addictive behavior, and hypertension (see also Pacher 2007, Physiol Rev 87:315-424).

While not wishing to be limited by any specific example, several uses of the compounds, compositions, and methods of the invention include: extending the therapeutic potency and efficacy of narcotic analgesics for pain relief, reducing the side effects of narcotic analgesics, and improving the safety profile of narcotic, and other, analgesics, improving muscle strength in patients experiencing hypoxia (see Clanton, 2007, J Appl Physiol 102:2379-2388) and restoring the ability of breathing control chemoreceptors to function properly (Zakynthinos et al., 2007, Am J Respir Crit Care Med 175: 62-68). Additional examples also include: enhancing muscle strength for certain types of neuromuscular disease such as Duchenne Muscular Dystrophy, (Williams et al., 2007, Am J Physiol Heart Circ Physiol 293:H1969-H1977; Tidball and Wehling-Hendricks, 2007, J Appl Physiol 102:1677-1686; Whitehead et al., 2008, J Physiol 7:2003-2014), Huntington's disease (Perez-De La Cruz et al., 2009, Behav Brain Res 199:210-217), and Parkinson's Disease (Pinnen et al., 2009, J Med Chem 52:559-563).

In one nonlimiting embodiment, the compounds, compositions, and methods of the invention are used as an anti-oxidant therapy, including for example, anti-oxidant therapy to treat psychiatric disorders, metabolic disorders, and addiction. Anti-oxidant therapy has been suggested for a wide variety of psychiatric and metabolic disorders (Bhardwaj et al., 2009, Gastroenterology 136:149-159; Ng et al., 2008, Int J Neuropsychopharmacol 11:851-76). For example, N-acetylcysteine, an antioxidant, has also been proposed for addiction behavior/neurological damage including methamphetamine (Imam et al., 2001, Ann NY Acad Sci 939:366-380), cocaine or heroin addiction (Madayag et al., 2007, J Neuroscience 27:13968-13976; LaRowe et al., 2007, Am J Psychiatry 164:1115-1117; Zhou and Kalicas, 2008, Biol Psychiatry 63:338-340; Mardikian et al., 2007, Prog Neuro-psychopharmacol Biol Psychiatry 31:389-394).

In another aspect of the invention, the analgesic pain relieving effects of narcotic analgesics are preserved and decoupled from their dangerous and discomforting side effects. For example, for treatment of moderate to severe pain, the narcotic analgesics (e.g., morphine) are still the mainstay of therapy for many indications. The major drawbacks to the use of narcotic analgesics include a variety of side effects including respiratory depression, constipation, sedation and urinary retention. Thus, in one embodiment, the compounds, compositions, and methods of the invention extend the analgesic effect of narcotic analgesics. In another embodiment, the compound, compositions, and methods of the invention blunt the respiratory depression associated with the use of narcotic analgesics. In still another embodiment, the compound, compositions, and methods of the invention extend the analgesic effect of narcotic analgesics and blunt the respiratory depression associated with the use of narcotic analgesics. In various embodiments of the invention, the decreased dose of narcotic analgesic necessary to achieve the same level of analgesia provides for fewer or less severe side effects, such as, respiratory depression, constipation, sedation, and urinary retention. Similarly, reducing the dose of narcotic needed to achieve adequate pain relief can also reduce the likelihood of a patient developing dependence on opioids or suffering opioid withdrawal upon discontinuation of treatment, thereby reducing the likelihood of narcotic abuse.

Methods of treatment of the invention also include administration of a compound and/or composition of the invention to stabilize the breathing rhythm of a subject, as well as administration of a compound and/or composition of the invention to increase minute ventilation of a subject. In an embodiment, a method of the invention includes administration of a compound and/or composition of the invention to stabilize the breathing rhythm of a subject. In another embodiment, a method of the invention includes administration of a compound and/or composition of the invention to increase minute ventilation of a subject. In an aspect, minute ventilation of a subject is increased at the level of the brainstem respiratory control center in the nucleus tractus solitarius.

Compounds of the Invention

The compounds of the invention include those compounds having a structure according to Formula I or a salt thereof.

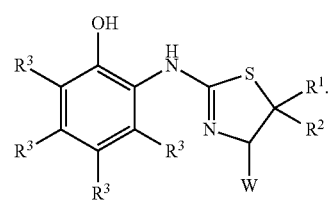

Formula I

In Formula I, $R^1$ and $R^2$ can be, independently, hydrogen or alkyl. Alternatively, $R^1$ and $R^2$ can together form a radical according to the formula $(CH_2)_n$, wherein $2 \leq n \leq 6$.

$R^3$ can be, independently at each occurrence, hydrogen, alkyl, substituted alkyl, alkenyl, alkynyl, halogen, phenyl, substituted phenyl, aryl, substituted aryl, heteroaryl, substituted heteroaryl, hydroxyl, alkoxy, cyano, nitro, acyl, carboxy, carboxyalkyl, or amido.

$R^4$ can be hydrogen, alkyl, substituted alkyl, or acyl.

W can be hydrogen, alkyl, aryl, substituted aryl, heteroaryl, substituted heteroaryl, carboxy, or carboxyalkyl.

As used herein, the term "alkyl", by itself or as part of another substituent means a saturated straight, branched, or cyclic hydrocarbon having the number of carbon atoms designated according to the notation $C_x$-$C_y$ wherein $1 \leq x \leq y \leq 10$. According to this notation, ($C_1$-$C_6$)alkyl means the group of saturated straight, branched, or cyclic hydrocarbons having from 1 to 6 carbon atoms. Examples of alkyl groups include, but are not limited to, methyl, ethyl, propyl, isopropyl, butyl, isobutyl, tertbutyl, pentyl, neopentyl, hexyl, cyclohexyl and cyclopropylmethyl.

As used herein the term "acyl" refers to an alkyl group connected to a carbonyl group. Acyl groups may be represented by the formula —C(O)alkyl. Examples of acyl groups include, but are not limited to, acetyl, pivaloyl, propanoyl, and isobutanoyl.

The term "alkenyl" employed alone or in combination with other terms, means, unless otherwise stated, a stable monounsaturated or di-unsaturated straight chain, branched chain or cyclic hydrocarbon group having the number of carbon atoms designated according to the notation $C_x$-$C_y$ wherein $1 \leq x \leq y \leq 10$. According to this notation, ($C_1$-$C_6$)alkenyl means the group of mono- or di-unsaturated straight, branched, or cyclic hydrocarbons having from 1 to 6 carbon atoms. Examples of alkenyl radicals include, but are not limited to, vinyl, propenyl (allyl), crotyl, isopentenyl, butadienyl, 1,3-pentadienyl, 1,4-pentadienyl, cyclopentenyl, cyclopentadienyl and the higher homologs and isomers. Alkenyl groups may be represented by according to the notation $CH_2$=$CHCH_2$—.

The term "alkoxy" employed alone or in combination with other terms refers to a group having the structure "alkyl-O—". Examples include but are not limited to, methoxy ($CH_3O$—), ethoxy ($CH_3CH_2O$—), 1-propoxy ($CH_3CH_2CH_2O$—), and isopropoxy ($CH_3(CHO$—)$CH_3$). Preferred embodiments include ($C_1$-$C_3$)alkoxy, particularly ethoxy and methoxy.

The term "alkoxycarbonyl," as used herein, refers to an alkoxy group, bound to a carbonyl group, said alkoxycarbonyl group having the structure "alkoxy-C(O)—"

The term "carboxy" or "carboxyl," as used herein, refers to a —$CO_2H$ group.

The term "carboxyalkyl," as used herein, refers to a compound having the formula "—C(O)O-alkyl".

The term "aryl", employed alone or in combination with other terms, means a carbocyclic aromatic system containing one or more rings (typically one, two or three rings) wherein said rings may be attached together in a pendent manner, such as a biphenyl, or may be fused, such as in naphthalene. Examples include, but are not limited to, phenyl, anthracyl, and naphthyl.

The term "heterocycle" or "heterocyclic," as defined herein, refers to monocyclic, bicyclic, or tricyclic ring systems containing at least one heteroatom. Monocyclic ring systems are exemplified by any 3- or 4-membered ring containing a heteroatom independently selected from oxygen, nitrogen and sulfur; or a 5-, 6- or 7-membered ring containing one, two, three, or four heteroatoms wherein the heteroatoms are independently selected from nitrogen, oxygen and sulfur. The 5-membered ring has from 0-2 double bonds and the 6- and 7-membered ring has from 0-3 double bonds. Representative examples of monocyclic ring systems include, but are not limited to, azetidinyl, azepinyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, N-methylpiperazinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridyl, pyrimidinyl, pyridazinyl, pyrrolyl, pyrrolinyl, pyrrolidinyl, tetrahydrofuranyl, tetrahydrothienyl, tetrazinyl, tetrazolyl, 1,2,3-thiadiazolyl, 1,2,4-thiadiazolyl, 1,3,4-thiadiazolyl, thiadiazolinyl, thiadiazolidinyl, thiazolyl, thiazolinyl, thiazolidinyl, thienyl, thiomorpholinyl, 1,1-dioxidothiomorpholinyl, thiopyranyl, triazinyl, triazolyl, and trithianyl.

The term "heteroaryl" refers specifically to mono and polycyclic heterocycles having aromatic character. Examples of monocyclic heteroaryl groups include, but are not limited to, pyridyl, pyrazinyl, pyrimidinyl, pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heteroaryl groups include, but are not limited to, indolyl, indolinyl, quinolyl, tetrahydroquinolyl, isoquinolyl, 1,2,3,4-tetrahydroisoquinolyl, cinnolinyl, quinoxalinyl, quinazolinyl, phthalazinyl, 1,8-naphthyridinyl, 1,4-benzodioxanyl, coumarin, dihydrocoumarin, benzofuryl, 2,3-dihydrobenzofuryl, 1,2-benzisoxazolyl, benzothienyl, benzoxazolyl, benzthiazolyl, purinyl, benzimidazolyl, benztriazolyl, thioxanthinyl, carbazolyl, carbolinyl, acridinyl, pyrrolizidinyl, and quinolizidinyl.

The term "halogen" means, unless otherwise stated, a fluorine, chlorine, bromine, or iodine atom.

The term "($C_x$-$C_y$)perfluoroalkyl," wherein $x<y$, means an alkyl group with a minimum of x carbon atoms and a maximum of y carbon atoms, wherein all hydrogen atoms are replaced by fluorine atoms. Examples include, but are not limited to, trifluoromethyl and pentafluoroethyl.

Tautomerism

"Tautomers" are structurally distinct isomers that interconvert by tautomerization. "Tautomerization" is a form of isomerization involving the migration of a proton accompanied by changes in bond order, often the interchange of a single bond with an adjacent double bond. Where tautomerization is possible, (e.g., in solution), a chemical equilibrium of tautomers can be reached. One well known example of tautomerization is between a ketone and its corresponding enol. Compounds according to Formula I may also undergo tautomerization and may exist in Form 1, Form 2, or as a mixture thereof.

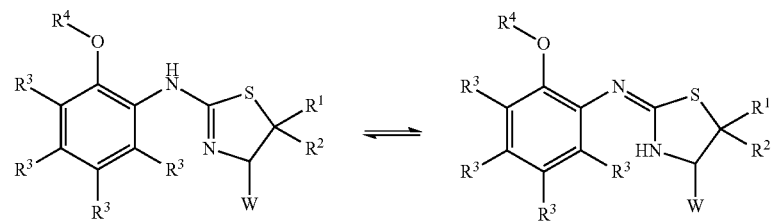

Form 1        Form 2

For purposes of the present invention, all compounds will be drawn in only one tautomeric configuration. It should be understood, though, that both tautomeric forms of a given compound are contemplated and within the scope of the present invention. Thus, any discussion of any compound disclosed herein should be understood to include both tautomeric forms of that compound, unless otherwise specified.

Acid Addition Salts

Compounds according to Formula I contain a basic nitrogen that can be protonated by a sufficiently strong protic acid. Although any sufficiently strong protic acid may be used, pharmaceutically-acceptable acids are preferred so that pharmaceutically-acceptable acid addition salts are formed when pharmaceutical compositions are desired. Pharmaceutically-acceptable acids refers to those acids that are not toxic or otherwise biologically undesirable. Pharmaceutically acceptable acid addition salts may be formed with pharmaceutically-acceptable inorganic acids including, but not limited to, hydrochloric acid, hydrobromic acid, sulfuric acid, sulfamic acid, nitric acid, phosphoric acid, and the like.

Pharmaceutically acceptable acid addition salts may also be formed with pharmaceutically acceptable organic acids. Examples of pharmaceutically-acceptable organic acids, include but are not limited to, acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid, and the like.

Methods of Preparation

Compounds of the invention or a salt thereof may be prepared according to the following general schemes. For example, according to Scheme 1, a compound of the invention may be prepared by reacting a compound according to formula A, wherein Z is a leaving group, with an aminoalkylthiol B. This results in product compounds according to Formula I.

Scheme 1

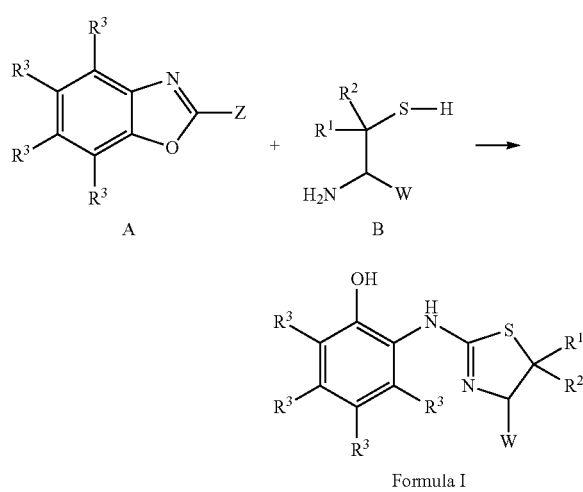

Alternatively, a protected aminoalkylthiol C can be reacted with a compound of formula A, wherein Z is a leaving group and P is a thiol protecting group, to give the corresponding adduct D. Subsequent S-deprotection produces compounds according to Formula I. Suitable thiol protecting groups are identified in Wuts, et al. Greene's Protective Groups in Organic Synthesis, 4$^{th}$ Edition. New York. John Wiley & Sons. 2007, the entirety of which is incorporated herein by reference. Preferred thiol protecting groups include triphenylmethyl, also referred to as "trityl" or "Tr", and 4-methoxybenzyl.

Scheme 2

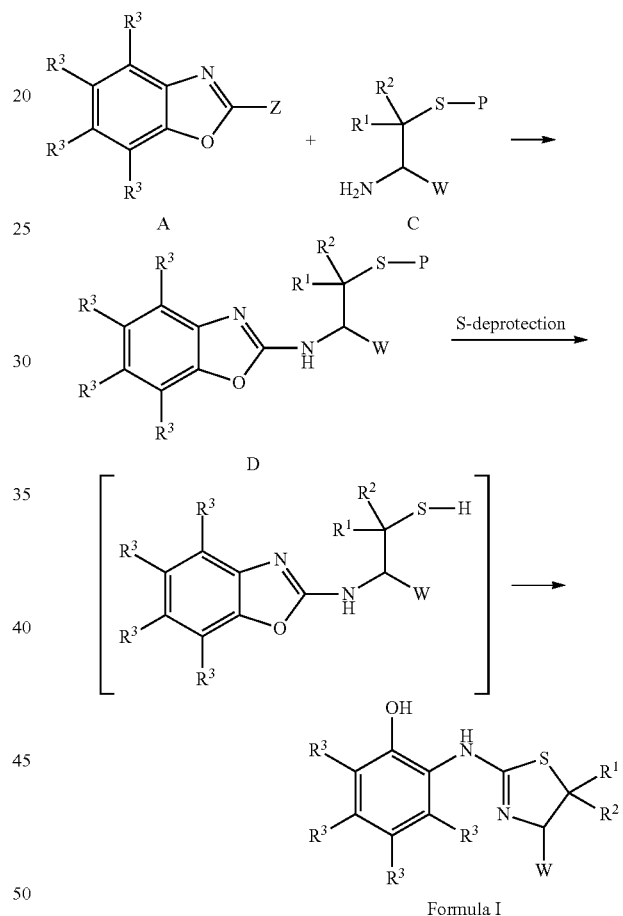

In certain embodiments, compounds according to formula A may be prepared beginning with a substituted phenol, according to formula E, as is shown in Scheme 3. Depending upon the nature of $R^3$, a compound according to formula E may be commercially available or easily prepared according to known methods in organic chemistry.

In Scheme 3, substituted phenol E can be nitrated to give the corresponding ortho-nitrophenol F. This material can then be reduced to provide the ortho-aminophenol G. The aminophenol G can subsequently be reacted with potassium ethyl xanthate (potassium (carbodithiolatooxy)ethane) to produce the cyclized 2-mercaptobenzoxazole H. Reaction of the 2-mercaptobenzoxazole H with a chlorinating agent, such as thionyl chloride, affords the desired 2-chlorobenzoxazole J.

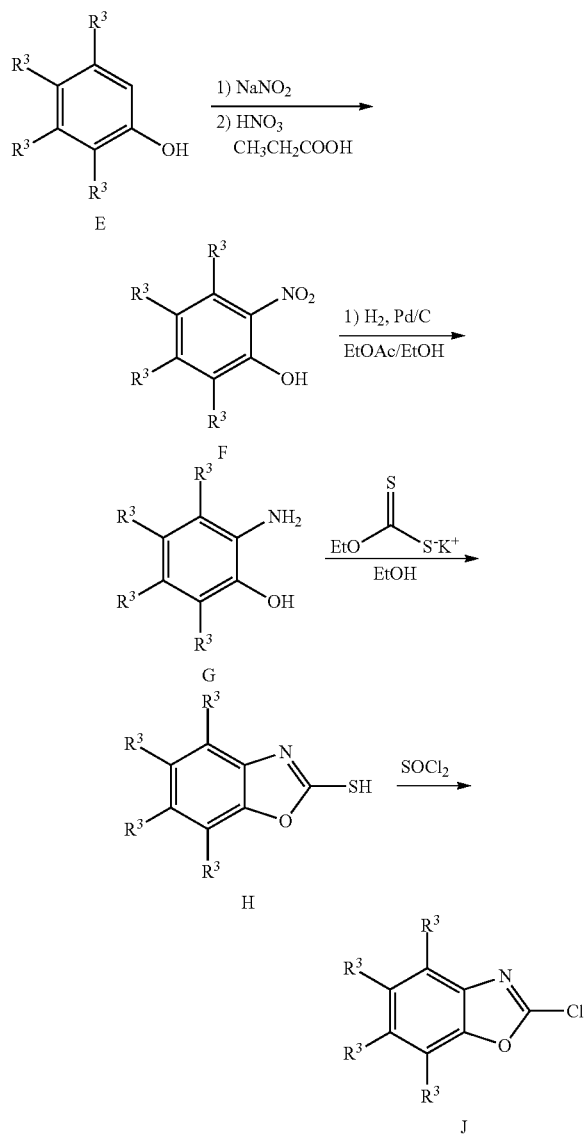

In certain embodiments, the nitration and/or reduction steps may be avoided by using a commercially available compound corresponding to advanced intermediate F or G.

Pharmaceutical Compositions and Therapies

The invention also encompasses pharmaceutical compositions ("compositions") and methods of their use. These pharmaceutical compositions may comprise an "active ingredient" (one or more compounds of the invention, or pharmaceutically acceptable salts thereof) in combination with one or more pharmaceutically acceptable agents. The compositions set forth herein can be used alone or in combination with additional compounds to produce additive, complementary, or synergistic effects.

In an embodiment, the pharmaceutical compositions useful for practicing the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

In certain embodiments, the compositions of the invention may include one or more pharmaceutically acceptable carriers. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as anti-oxidants, dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Pharmaceutical compositions that are useful in the methods of the invention may be administered, prepared, packaged, and/or sold in formulations suitable for intravenous, subcutaneous, sublingual, oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

The compositions of the invention may be administered via numerous routes, including, but not limited to, intravenous, subcutaneous, sublingual, oral, rectal, vaginal, parenteral, topical, pulmonary, intranasal, buccal, or ophthalmic administration routes. The route(s) of administration will be readily apparent to the skilled artisan and will depend upon any number of factors including the type and severity of the disorder being treated, the type and age of the veterinary or human patient being treated, and the like.

Pharmaceutical compositions that are useful in the methods of the invention may be administered systemically in intravenous and subcutaneous liquid formulations, oral and sublingual solid formulations, ophthalmic, suppository, aerosol, topical or other similar formulations. In addition to the compound such as heparin sulfate, or a biological equivalent thereof, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer compounds according to the methods of the invention.

Compounds which are identified using any of the methods described herein, and combinations of such compounds, may be formulated and administered to a subject for treatment of disordered control of breathing.

Such a pharmaceutical composition may consist of the active ingredient alone, in a form suitable for administration to a subject, or the pharmaceutical composition may comprise at least one active ingredient and one or more pharmaceutically acceptable carriers, one or more additional ingredients, or some combination of these. As described elsewhere, the active ingredient may be present in the pharmaceutical composition in the form of a physiologically or pharmaceutically acceptable salt, such as in combination with a physiologically or pharmaceutically acceptable cation or anion, as is well known in the art.

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to subjects of all sorts.

Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

Pharmaceutical compositions that are useful in the methods of the invention may be prepared, packaged, or sold in formulations suitable for intravenous, subcutaneous, sublingual, oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically based formulations.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Controlled- or sustained-release formulations of a pharmaceutical composition of the invention may be made using conventional technology. Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, polar lipids, or N-methyl-2-pyrrolidone.

One acceptable vehicle for topical delivery of some of the compositions of the invention may contain liposomes. The composition of the liposomes and their use are known in the art (for example, see Constanza, U.S. Pat. No. 6,323,219).

The source of active compound to be formulated will generally depend upon the particular form of the compound. Small organic molecules and peptidyl or oligo fragments can be chemically synthesized and provided in a pure form suitable for pharmaceutical usage. Products of natural extracts can be purified according to techniques known in the art. Recombinant sources of compounds are also available to those of ordinary skill in the art.

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

Liquid derivatives and natural extracts made directly from biological sources may be employed in the compositions of this invention in a concentration (w/v) from about 1 to about 99%. Fractions of natural extracts and protease inhibitors may have a different preferred range, from about 0.01% to about 20% and, more preferably, from about 1% to about 10% of the composition. Of course, mixtures of the active agents of this invention may be combined and used together in the same formulation, or in serial applications of different formulations.

The composition of the invention may comprise a preservative from about 0.005% to 2.0% by total weight of the composition. The preservative is used to prevent spoilage in the case of an aqueous gel because of repeated patient use when it is exposed to contaminants in the environment from, for example, exposure to air or the patient's skin, including contact with the fingers used for applying a composition of the invention such as a therapeutic gel or cream. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the compound for use in the invention in the aqueous gel formulation. Preferred antioxidants for some compounds are BHT, BHA, α-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g., disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art. Controlled-release preparations may also be used and the methods for the use of such preparations are known to those of skill in the art.

In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets that are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

As used herein, an "oily" liquid is one which comprises a carbon-containing liquid molecule and which exhibits a less polar character than water.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The terms oral rinse and mouthwash are used interchangeably herein.

A pharmaceutical composition of the invention may be prepared, packaged, or sold in a formulation suitable for oral or buccal administration. Such a formulation may comprise, but is not limited to, a gel, a liquid, a suspension, a paste, toothpaste, a mouthwash or oral rinse, and a coating. For example, an oral rinse of the invention may comprise a compound of the invention at about 1.4%, chlorhexidine gluconate (0.12%), ethanol (11.2%), sodium saccharin (0.15%), FD&C Blue No. 1 (0.001%), peppermint oil (0.5%), glycerine (10.0%), Tween 60 (0.3%), and water to 100%. In another embodiment, a toothpaste of the invention may comprise a compound of the invention at about 5.5%, sorbitol, 70% in water (25.0%), sodium saccharin (0.15%), sodium lauryl sulfate (1.75%), carbopol 934, 6% dispersion in (15%), oil of spearmint (1.0%), sodium hydroxide, 50% in water (0.76%), dibasic calcium phosphate dihydrate (45%), and water to 100%. The examples of formulations described herein are not exhaustive and it is understood that the invention includes additional modifications of these and other formulations not described herein, but which are known to those of skill in the art.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin. Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as antioxidants, dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for buccal administration. Such formulations may, for example, be in the form of tablets or lozenges made using conventional methods, and may, for example, contain about 0.1 to about 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Typically, dosages of the compound of the invention which may be administered to a subject, preferably a human, will vary depending upon any number of factors, including but not limited to, the type of animal and type of disease state being treated, the age of the subject and the route of administration. The compound can be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the subject, etc.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual and partial numbers within that range, for example, 1, 2, 3, 4, 5, 5.5 and 6. This applies regardless of the breadth of the range.

It is contemplated that any embodiment discussed in this specification can be implemented with respect to any method or composition of the invention, and vice versa. Furthermore, compositions of the invention can be used to achieve methods of the invention.

Experimental Examples

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The Materials and Methods are now described.

Exemplary compounds of the invention are set forth in Table 1. Table 1 also identifies benzoxazoles used to prepare the exemplary compounds of the invention, as well as the starting material used to prepare these benzoxazoles. Commercially available compounds do not include compound numbers under the structure.

TABLE 1

| Starting Material | Benzoxazole | Exemplary Compounds of The Invention | Compound Name |
|---|---|---|---|
| N/A | [benzoxazole-2-Cl structure] | [structure 1] | (S)-2-(2-hydroxyphenyl-amino)-thiazoline-5,5-dimethyl-4-carboxylic acid |
| N/A | [benzoxazole-2-Cl structure] | [structure 2] | (R)-2-(2-hydroxyphenyl-amino)-thiazoline-5,5-dimethyl-4-carboxylic acid |
| [MeO-phenyl-NO$_2$, OH structure] | [6-MeO-benzoxazole-2-Cl structure 3] | [structure 4] | (R)-2-(2-Hydroxy-4-methoxyphenyl amino)-thiazoline-4-carboxylic acid |
| [F-phenyl-NO$_2$, OH structure] | [6-F-benzoxazole-2-Cl structure 5] | [structure 6] | (R)-2-(4-Fluoro-2-hydroxyphenyl-amino)-thiazoline-4-carboxylic acid |

TABLE 1-continued

| Starting Material | Benzoxazole | Exemplary Compounds of The Invention | Compound Name |
|---|---|---|---|
| 7 | 7 | 8 | (R)-2-(3,5-Dichloro-2-hydroxy-4-methylphenylamino)-thiazoline-4-carboxylic acid |
| 9 | 9 | 10 | (R)-2-(5-tert-Butyl-2-hydroxyphenylamino)-thiazoline-4-carboxylic acid |
| 11 | 11 | 12 | (R)-2-(2-Hydroxy-4-methoxycarbonylphenylamino)-thiazoline-4-carboxylic acid |
| 13 | 13 | 14 | (R)-2-(5-Ethanesulfonyl-2-hydroxyphenylamino)-thiazoline-4-carboxylic acid |
| 15 | 15 | 16 | (R)-2-(4-Chloro-2-hydroxyphenylamino)-thiazoline-4-carboxylic acid |
| 17 | 17 | 18 | (R)-2-(2-Hydroxy-5-methoxyphenylamino)-thiazoline-4-carboxylic acid |

TABLE 1-continued

| Starting Material | Benzoxazole | Exemplary Compounds of The Invention | Compound Name |
|---|---|---|---|
| 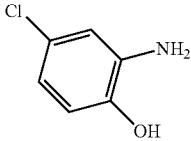 | 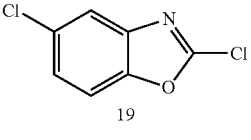 19 | 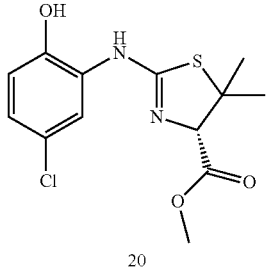 20 | (S)-2-(2-Hydroxy-5-chlorophenyl-amino)-thiazoline-5,5-dimethyl-4-carboxylic acid methyl ester |
| 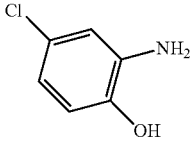 | 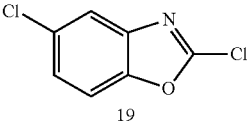 19 | 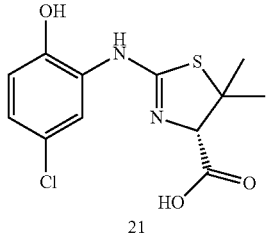 21 | (S)-2-(2-Hydroxy-5-chlorophenyl-amino)-thiazoline-5,5-dimethyl-4-carboxylic acid |
| 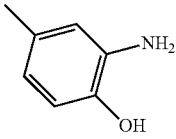 | 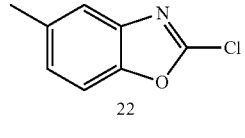 22 | 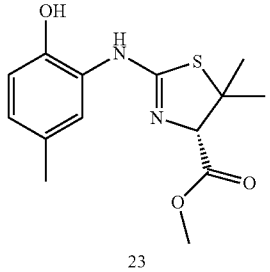 23 | (S)-2-(2-Hydroxy-5-methylphenyl-amino)-thiazoline-5,5-dimethyl-4-carboxylic acid methyl ester |
| 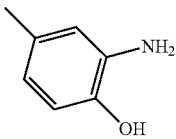 | 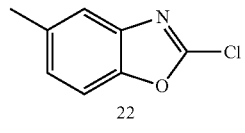 22 | 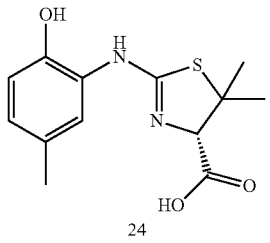 24 | (S)-2-(2-Hydroxy-5-methylphenyl-amino)-thiazoline-5,5-dimethyl-4-carboxylic acid |
| 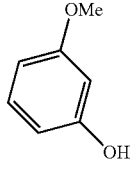 | 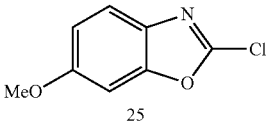 25 | 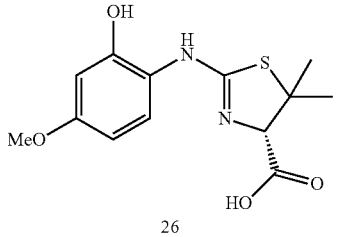 26 | (S)-2-(2-Hydroxy-4-methoxyphenyl amino)-thiazoline-5,5-dimethyl-4-carboxylic acid |
| 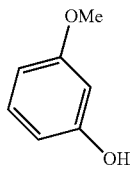 | 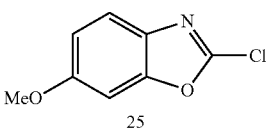 25 | 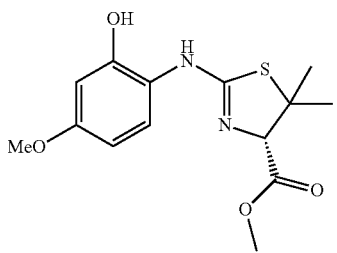 [SMILES: COC(=O)[C@@H]1N=C(Nc2ccc(OC)cc2O)SC1(C)C] 27 | (S)-2-(2-Hydroxy-4-methoxyphenyl amino)-thiazoline-5,5-dimethyl-4-carboxylic acid methyl ester |

TABLE 1-continued

| Starting Material | Benzoxazole | Exemplary Compounds of The Invention | Compound Name |
|---|---|---|---|
| 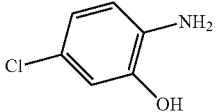 | 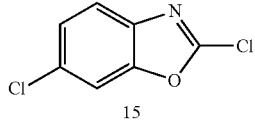 15 | 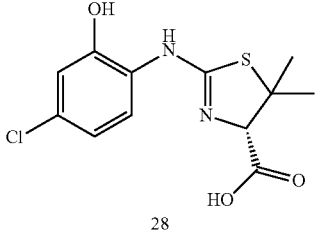 28 | (S)-2-(4-Chloro-2-hydroxyphenyl-amino)-thiazoline-5,5-dimethyl-4-carboxylic acid |
| 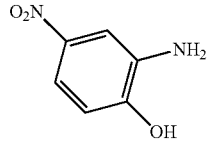 [SMILES: Nc1cc([N+](=O)[O-])ccc1O] | 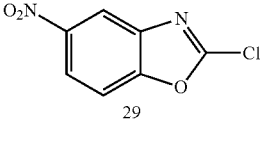 29 | 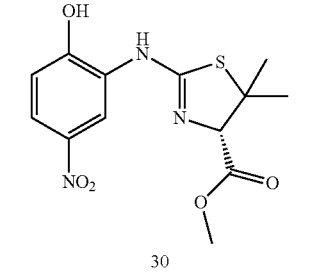 30 | (S)-2-(2-Hydroxy-5-nitrophenyl-amino)-thiazoline-5,5-dimethyl-4-carboxylic acid methyl ester |
| 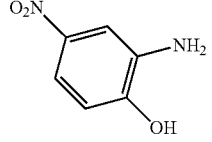 [SMILES: Nc1cc([N+](=O)[O-])ccc1O] | 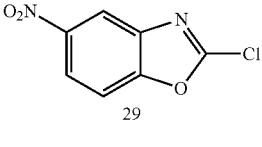 29 | 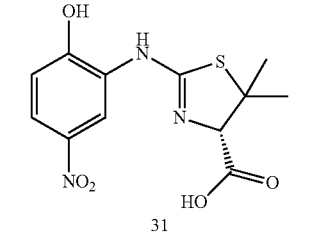 31 | (S)-2-(2-Hydroxy-5-nitrophenyl-amino)-thiazoline-5,5-dimethyl-4-carboxylic acid |
| 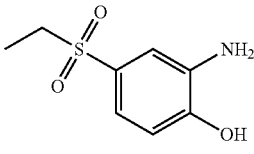 | 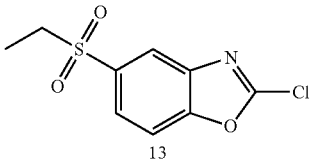 13 | 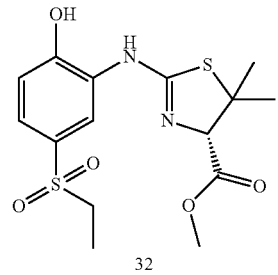 32 | (S)-2-(5-Ethanesulfonyl-2-hydroxyphenyl-amino)-thiazoline-5,5-dimethyl-4-carboxylic acid methyl ester |
| 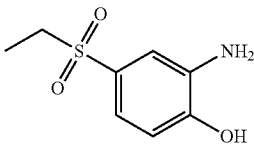 | 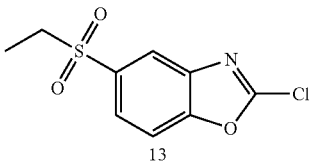 13 | 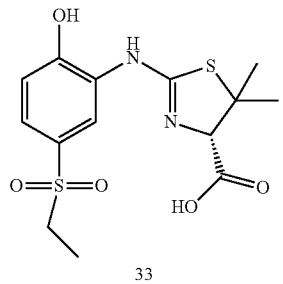 33 | (S)-2-(5-Ethanesulfonyl-2-hydroxyphenyl-amino)-thiazoline-5,5-dimethyl-4-carboxylic acid |

TABLE 1-continued

| Starting Material | Benzoxazole | Exemplary Compounds of The Invention | Compound Name |
|---|---|---|---|
| N/A | 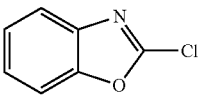 | 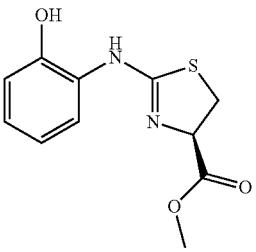 [SMILES: COC(=O)[C@@H]1CSC(Nc2ccccc2O)=N1] 34 | (R)-2-(2-hydroxyphenyl-amino)-thiazoline-4-carboxylic acid methyl ester |
| N/A | 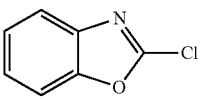 | 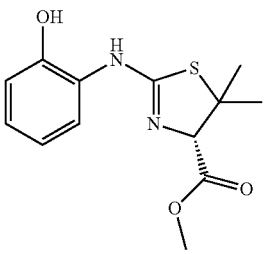 [SMILES: COC(=O)[C@@H]1N=C(Nc2ccccc2O)SC1(C)C] 35 | (S)-2-(2-hydroxyphenyl-amino)-thiazoline-5,5-dimethyl-4-carboxylic acid methyl ester |
| 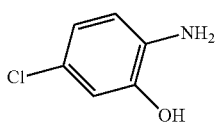 | 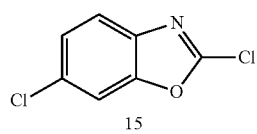 15 | 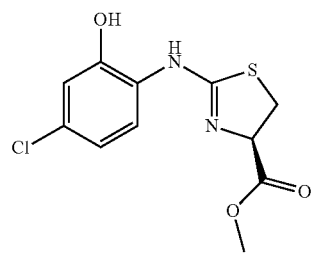 [SMILES: COC(=O)[C@@H]1CSC(Nc2ccc(Cl)cc2O)=N1] 36 | (R)-2-(4-chloro-2-hydroxyphenyl-amino)-thiazoline-4-carboxylic acid methyl ester |
| 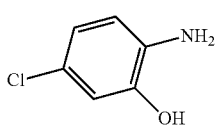 | 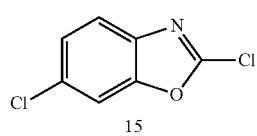 15 | 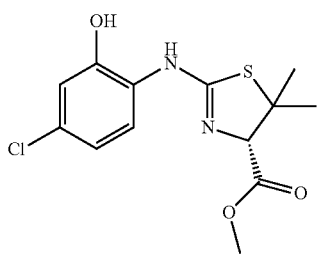 [SMILES: COC(=O)[C@@H]1N=C(Nc2ccc(Cl)cc2O)SC1(C)C] 37 | (S)-2-(4-chloro-2-hydroxyphenyl-amino)-thiazoline-5,5-dimethyl-4-carboxylic acid methyl ester |
| 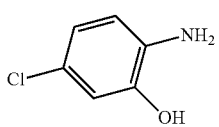 | 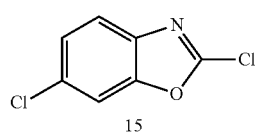 15 | 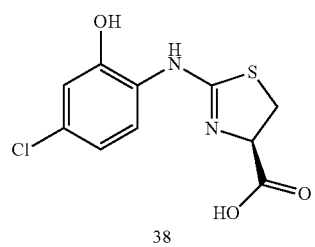 38 | (R)-2-(4-chloro-2-hydroxyphenyl-amino)-thiazoline-4-carboxylic acid |

TABLE 1-continued

| Starting Material | Benzoxazole | Exemplary Compounds of The Invention | Compound Name |
|---|---|---|---|
| N/A | 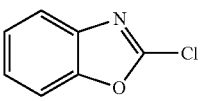 | 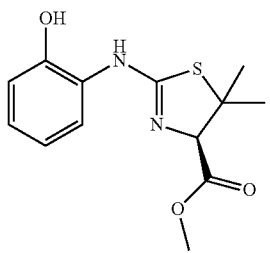 [SMILES: COC(=O)[C@H]1N=C(Nc2ccccc2O)SC1(C)C]<br>39 | (R)-2-(2-hydroxyphenyl-amino)-thiazoline-5,5-dimethyl-4-carboxylic acid methyl ester |

Benzoxazole Formation Procedures:

Compound 3:

A solution of 3-methoxyphenol (10 g, 80.55 mmol) in propionic acid (80 mL) was treated at −5° C. with a solution of NaNO$_2$ (5.61 g, 81.30 mmol) in water (13 mL). After stirring for 1 h at −5° C., nitric acid (6.7 mL, 161.10 mmol) was added. The slurry was stirred for 1 h at −5° C., and then at room temperature for 16 h. Water (80 mL) was then added in a dropwise fashion at room temperature. The resultant solid was filtered, washed with 50% aqueous propionic acid, and dried to give 7.47 g (55%) of 5-methoxy-2-nitro-phenol.

Subsequently, a mixture of 5-methoxy-2-nitrophenol (7.47 g) and 10% Pd/C (1.87 g) was prepared in an ethyl acetate/ethanol (100 mL, 1:1 v/v) mixture. The resulting slurry was stirred under an H$_2$ atmosphere for 3.5 h at room temperature. Hydrogen was subsequently purged from the reaction flask and the reaction mixture was filtered through Celite. After washing the celite pad with additional solvent, volatiles in the resultant filtrate were removed in vacuo to give 2-amino-5-methoxyphenol (6.03 g, 98%).

Next, a mixture of 2-amino-5-methoxyphenol (3c) (6.03 g, 43.33 mmol) and potassium ethyl xanthate (6.95 g, 73.33 mmol) in ethanol (80 mL) was heated at reflux for 18 h. The reaction was subsequently cooled and the solvent was removed in vacuo. The residue was taken up in ethyl acetate (150 mL), washed successively with 4N HCl, water, and brine. The organic solution was subsequently dried over Na$_2$SO$_4$. After filtration to remove the drying aid, the solvent was evaporated to give 6.23 g (79%) of 6-methoxybenzoxazole-2-thiol.

Finally, a mixture of 6-methoxybenzoxazole-2-thiol (5.16 g, 28.48 mmol), thionyl chloride (28 mL) and catalytic amount of DMF (60 µL) was stirred at room temperature for 4 h. Volatiles were removed in vacuo. Toluene (30 mL) was added to the residue and the mixture was evaporated. This procedure was repeated two more times to give crude compound 3, namely, 2-chloro-6-methoxybenzoxazole.

Compound 5:

Compound 5 was prepared in accordance with the general procedures set forth for compound 3, except that the starting material was 5-fluoro-2-nitrophenol and no nitration was performed.

Compound 7:

Compound 7 was prepared in accordance with the procedures set forth for compound 3, except that the starting material was 6-amino-2,4-chloro-3-methyl-phenol and no nitration or reduction were performed.

Compound 9:

Compound 9 was prepared in accordance with the procedure set forth for compound 3, except that the starting material was 2-amino-4-tert-butylphenol and no nitration or reduction were performed.

Compound 11:

Compound 11 was prepared in accordance with the procedure set forth for compound 3, except that the starting material was 4-amino-3-hydroxybenzoic acid methyl ester and no nitration or reduction were performed.

Compound 13:

Compound 13 was prepared in accordance with the procedures set forth for compound 3, except that the starting material was 2-amino-4-ethanesulfonylphenol and no nitration or reduction were performed.

Compound 15:

Compound 15 was prepared in accordance with the procedures set forth for compound 3, except that the starting material was 2-amino-5-chlorophenol and no nitration or reduction were performed.

Compound 17:

Compound 17 was prepared in accordance with the procedures set forth for compound 3, except that the starting material was 4-methoxy-2-nitrophenol and no nitration was performed.

Compound 19:

A mixture of potassium ethyl xanthate (13.4 g, 84.0 mmol) and 4-chloro-2-aminophenol (10 g, 69.6 mmol) was dissolved in absolute ethanol (200 mL). The mixture was stirred under reflux overnight. After cooling, the solvent was evaporated under reduced pressure, the residue was dissolved in water (200 mL) and treated with HOAc to adjust pH to 5. A solid formed, which was filtered and dried to afford 5-chloro-2-mercaptobenzoxazole (12.8 g, yield 99.1%).

Subsequently, 5-chloro-2-mercaptobenzoxazole (3.1 g, 16.7 mmol) was dissolved in thionyl chloride (30 mL, 413 mmol). DMF (1.5 mL) was added and the reaction mixture was heated at 65° C. for 45 min. The solvent was removed under reduced pressure and to the residue was added toluene (2×60 mL) followed by evaporation each time to remove the excess SOCl$_2$ (azetrope). The resultant crude product was dissolved in ethyl acetate (100 mL), washed with water (100 mL) and dried over Na$_2$SO$_4$. Evaporation of ethyl acetate gave 2,5-dichlorobenzoxazole, compound 19, as a red oil (3.2 g).

Compound 22:

A mixture of potassium ethyl xanthate (16.0 g, 0.1 mol) and 2-amino-4-methylphenol (12.3 g, 0.1 mol) was dissolved in absolute ethanol (150 mL). The mixture was stirred at reflux overnight. After cooling, the reaction solvent was evaporated under reduced pressure. The resultant residue was dissolved in water (200 mL) and treated with HOAc to pH to 5. The resultant solid was filtered and dried to afford 5-methyl-2-mercaptobenzoxazole (16.0 g, 96% yield).

Subsequently, the 5-methyl-2-mercaptobenzoxazole (6.2 g, 38 mmol) was dissolved in thionyl chloride (36.9 mL) and 2.79 mL of DMF was added. The reaction mixture was then stirred at r.t. for 30 min. The solvent was removed under reduced pressure and to the residue was added toluene (2×60 mL) followed by evaporation each time to remove excess $SOCl_2$ via an azetrope. The resultant crude product was dissolved in ethyl acetate (100 mL), washed with water (100 mL) and dried over $Na_2SO_4$. Evaporation of ethyl acetate gave crude 22 which was purified by silica-gel column chromatography (eluent: petroleum ether) to provide pure 2-chloro-5-methylbenzoxazole, compound 22, (3.5 g, 58%).

Compound 25:

To a solution of 3-methoxyphenol (11.1 g, 0.09 mmol) in propionic acid (90 mL) at 0° C., was added $NaNO_2$ (6.3 g, 0.09 mmol, in 5 mL water) dropwise. The mixture was stirred at 0° C. for 1 hour. Concentrated nitric acid (12 mL) was then added dropwise and the mixture was stirred for 1 hour at 0° C. and 2 hour at r.t. Water (30 mL) was subsequently added and the resulting precipitate was collected and washed with 50% propionic acid, giving 2-nitro-5-methoxyphenol as yellow solid (5.8 g, 40% yield).

Subsequently, a solution of the crude 2-nitro-5-methoxyphenol (5.0 g, 29.6 mmol) in MeOH (150 mL) was prepared to which Pd/C (1.0 g) was then added. The mixture was placed under an $H_2$ atmosphere for about 2-3 hours. After this time, the catalyst was removed via filtration and filtrate was concentrated to give 2-amino-5-methoxyphenol (4.0 g, 97% yield).

Next, a mixture of potassium ethyl xanthate (4.6 g, 28.8 mmol) and crude 2-amino-5-methoxyphenol (4.0 g, 28.8 mmol) was dissolved in ethanol (150 mL). The mixture was heated at 80° C. overnight. After cooling, the solvent was evaporated under reduced pressure. The resultant residue was dissolved in water and treated with 1N HCl to pH 5, resulting in a precipitate, which was collected. The solid thus collected was purified by chromatography with petroleum ether/ethyl acetate (3:1 v/v) to afford 2-mercapto-6-methoxybenzoxazole (4.0 g, yield 77%).

Finally, pure 2-mercapto-6-methoxybenzoxazole (4.0 g, 22.2 mmol) was dissolved in thionyl chloride (15 mL). DMF (1 mL) was added to the solution and the reaction mixture was stirred at r.t for 10 min. The solvent was removed under reduced pressure. The crude product was dissolved in ethyl acetate, washed with water, dried over $Na_2SO_4$, and concentrated to give crude 2-chloro-6-methoxybenzoxazole, which was purified by chromatography with petroleum ether/ethylacetate (3:1 v/v) to afford 2-chloro-6-methoxybenzoxazole, compound 25, (3.7 g, yield 92%).

Compound 29:

A mixture of 2-amino-4-nitrophenol (12.5 g, 71 mmol) and potassium ethyl xanthate (13 g, 81 mmol) were dissolved in ethanol (200 mL). The reaction was heated at reflux overnight. After cooling, solvent in the reaction mixture was evaporated under reduced pressure. The resultant residue was dissolved in water and adjusted to pH 2-3 with 2N HCl, resulting in the formation of a red solid. The red solid was filtered giving 2-mercapto-5-nitrobenzoxazole (10.6 g, 76%).

Subsequently, the crude 2-mercapto-5-nitrobenzoxazole (10 g, 51 mmol), previously prepared, was dissolved in thionyl chloride (100 mL). DMF (60 μL) was added and the reaction mixture was heated at 65° C. for 45 min. After cooling, the solvent was removed under reduced pressure and to the residue, toluene was added twice (2×20 mL) and each time subsequently evaporated in vacuo to remove volatiles via azeotrope. The resultant crude product was dissolved in ethyl acetate (400 mL), washed with brine (200 mL), dried over $Na_2SO_4$, filtered, and concentrated to give compound 29, 2-chloro-5-nitrobenzoxazole, as (8.2 g, crude).

Preparation of Compounds According to the Invention:
Purification Conditions:

Where specified, compounds of the invention were purified by reverse phase chromatography eluting with a water-acetonitrite gradient containing either 0.05% trifluoroacetic acid or 0.05% aqueous ammonia ($NH_4OH$). Accordingly compounds were obtained as either a trifluoroacetate salt or as a free base.

Where specified, esters were purified using normal phase HPLC using an ethyl acetate/petroleum ether gradient.

Where stated, compounds were isolated via dissolution in methanol followed by the addition of ethyl ether to induce precipitation/crystallization.

Compound 1:

To a solution of D-(-)-penicillamine (6.2 g, 41.5 mmol) and DIPEA (14 mL, 78.5 mmol) in 150 mL of MeOH/THF (1:2 v/v), was added 2-chlorobenzoxazole (7.4 g, 48.0 mmol) in a dropwise manner. The reaction was stirred overnight. The mixture was then concentrated in vacuo to afford a pale yellow oil, which was treated with 150 mL of concentrated HCl to produce a white solid. This product was filtered, washed with acetone (2×50 mL) and $Et_2O$ (3×50 mL) to yield (S)-2-(2-hydroxyphenylimino)-thiazolidine-5,5-dimethyl-4-carboxylic acid hydrochloride as a white solid (7.0 g, yield 56%).

Compound 2:

To a stirred solution of L-penicillamine (28.5 g, 0.19 mol) and 2-chlorobenzoxazole (35.4 g, 0.23 mol) in 400 mL of MeOH/THF (3:1 (v/v)) at r.t, was added N,N-diisopropylethylamine ("DIPEA") (66.1 mL, 0.38 mol) in a dropwise manner. The reaction was stirred overnight. The mixture was then concentrated at reduced pressure to afford pale yellow oil, which was formed white crystals when treated with concentrated HCl (300 mL). The white solid was filtered, washed with acetone (3×50 mL) and then with $Et_2O$ (5×50 mL). The resultant white solid was crystallized again from MeOH/DCM, washed with DCM (3×50 mL) and $Et_2O$ (2×50 mL) to yield compound 2 (as its HCl salt), (R)-2-(2-hydroxyphenylimino)-thiazolidine-5,5-dimethyl-4-carboxylic acid hydrochloride as a white solid (40.8 g, 71%). $^1$H NMR (DMSO-$d_6$, ppm): δ=13.2 (br s (ex), 0.3H), 12.1 (br s (ex), 0.6H), 10.5 (br s, 1.4H), 7.25 (m, 2H), 7.07 (d, 1H), 6.88 (t, 1H), 4.65 (br s, 1H), 1.72 (s, 3H), 1.51 (s, 3H). ESI-MS: 267.1 ($M^+$+H). HPLC purity: 95%.

Compound 4:

A solution of compound 3 (5.2 g, 28.32 mmol), (+)-S-trityl-L-cysteine (6) (9.34 g, 25.70 mmol) and DIPEA (6.4 mL, 38.68 mmol) in THF (25 mL) and methanol (40 mL) was stirred at room temperature for 3 h and then at 40° C. for 14 h. Volatiles were subsequently removed in vacuo. The resulting residue was suspended in water (60 mL) and acidified to pH 3 with 5% $KHSO_4$ solution. The resulting suspension was extracted with $CH_2Cl_2$ (60 mL). The organic phase was washed with water, dried over $Na_2SO_4$, filtered, and the solvent removed in vacuo. The residue was purified by flash column chromatography using gradient elution from $CH_2Cl_2$/MeOH (99:1) to $CH_2Cl_2$/EtOH (9:1) to give (R)-2-(6-methoxybenzoxazol-2-ylamino)-3-tritylsulfanyl-propionic acid (6.40 g, 49%). 400 MHz 1H-NMR (DMSO-$d_6$, ppm): 13.1-12.7 (1H, br s) 8.23 (1H, d, J=8.6 Hz) 7.38-7.19 (15H, m) 7.14 (1H, d, J=8.6 Hz) 7.08 (1H, d, J=2.1 Hz) 6.74 (1H, dd, J=8.6, 2.1 Hz) 4.13-4.06 (1H, m) 3.75 (3H, s) 2.75 (1H, dd, 9.5 Hz) 2.55-2.50 (1H, m). ESI-MS (m/z): 511 [M+H]+

Subsequently, a solution of (R)-2-(6-methoxybenzoxazol-2-ylamino)-3-tritylsulfanyl-propionic acid (4.0 g, 7.83 mmol) in $CH_2Cl_2$ (35 mL) was prepared. $Et_3SiH$ (4.2 mL, 25.8 mmol) was added to the solution, followed by TFA (6.0 mL, 78.3 mmol). The reaction mixture was stirred under argon at 0° C. for 30 min. The volatiles were removed in vacuo and the residue was purified by flash column chromatography using gradient elution from $CH_2Cl_2$/MeOH (99:1) to $CH_2Cl_2$/EtOH (1:2) to give compound compound 4 (1.2 g, 57%) as free amino acid.

The resulting free amino acid (680 mg, 2.53 mmol) was dissolved in THF (5.0 ml) and 1.1 equivalents of 2M HCl in $Et_2O$ (1.4 ml, 2.78 mmol) was added. The volatiles were removed in vacuo to give compound 4 as its HCl salt. 400 MHz 1H-NMR (DMSO-d6, ppm) 10.8-9.2 (2H, brs) 7.08 (1H, d, J=8.6 Hz) 6.39 (1H, d, J=2.7 Hz) 6.36 (1H, dd, J=8.6, 2.7 Hz) 4.82-4.76 (1H, m) 3.67 (3H, s) 3.63 (1H, dd, 9.0 Hz) 3.51 (1H, dd, J=11.0, 5.7 Hz). ESI-MS (m/z): 269 [M+H]+.

Compound 6:

A solution of compound 5 (4.24 g, 24.71 mmol), (+)—S-trityl-L-cysteine (8.16 g, 22.45 mmol) and DIPEA (5.6 mL, 33.67 mmol) in THF (20 mL) and methanol (35 mL) was stirred at room temperature for 24 h. Volatiles were removed in vacuo. The residue was suspended in water and acidified to pH 3 with 5% $KHSO_4$ solution. The resulting suspension was extracted with $CH_2Cl_2$ (2×100 mL). The organic phase was washed with water, dried over $Na_2SO_4$, filtered, and the solvent removed in vacuo. The residue was purified by flash column chromatography using gradient elution from $CH_2Cl_2$/MeOH (99:1) to $CH_2Cl_2$/EtOH (9:1) to give (R)-2-(6-fluorobenzoxazol-2-ylamino)-3-tritylsulfanyl-propionic acid (7.80 g, 70%). 400 MHz $^1$H-NMR (DMSO-$d_6$, ppm): 8.46 (1H, d, J=8.6 Hz) 7.40 (1H, dd, J=8.4, 2.4 Hz) 7.35-7.20 (16H, m) 6.99 (1H, ddd, J=10.2, 8.4, 2.4 Hz) 4.14-4.06 (1H, m) 2.76 (1H, dd, J=12.5, 9.6 Hz) 2.53 (1H, dd, J=12.5, 4.4 Hz). ESI-MS (m/z): 499 [M+H]+

Compound 6, as its HCl salt, was prepared in 83% yield from (R)-2-(6-fluorobenzoxazol-2-ylamino)-3-tritylsulfanyl-propionic acid according to the general procedures described for the preparation of compound 4. 400 MHz $^1$H-NMR (DMSO-$d_6$, ppm): 12.3-10.8 (3H, br s) 7.27 (1H, dd, J=8.7, 6.4 Hz) 6.87 (1H, dd, J=10.4, 2.0 Hz) 6.72 (1H, ddd, J=8.7, 8.7, 2.5 Hz) 4.98-4.90 (1H, m) 3.95-3.83 (1H, m) 3.68 (1H, dd, J=8.2, 3.5 Hz). ESI-MS (m/z): 257 [M+H]+. Melting point: 109-111° C.

Compound 8:

(R)-2-(5,7-Dichloro-6-methylbenzoxazol-2-ylamino)-3-tritylsulfanyl-propionic acid was prepared from compound 7 according to the general procedures specified for compounds 4 and 6. 400 MHz $^1$H-NMR (DMSO-$d_6$, ppm): 13.5-12.5 (1H, br s) 8.85 (1H, d, J=8.2 Hz) 7.36 (1H, s) 7.34-7.20 (15H, m) 4.11-4.03 (1H, m) 2.76 (1H, dd, J=12.6, 9.9 Hz) 2.54 (1H, dd, J=12.6 Hz). ESI-MS (m/z): 563, 565, 567 [M+H]+.

Compound 8, as its HCl salt, was prepared in 50% yield from (R)-2-(5,7-dichloro-6-methylbenzoxazol-2-ylamino)-3-tritylsulfanyl-propionic acid according to the general procedures described for compounds 4 and 6. 400 MHz 1H-NMR (DMSO-$d_6$, ppm): 11.4-9.7 (2H, br s) 7.36 (1H, s) 4.96 (1H, dd, J=8.5, 3.4 Hz) 3.93-3.83 (1H, m) 3.70 (1H, dd, J=11.4, 3.4 Hz) 2.40 (3H, s). ESI-MS (m/z): 321, 323, 325 [M+H]+. Melting point: 205-207° C.

Compound 10:

(R)-2-(5-tert-Butylbenzoxazol-2-ylamino)-3-tritylsulfanyl-propionic acid was prepared from compound 9 in accordance with the procedures specified for compounds 4 and 6. 400 MHz $^1$H-NMR (DMSO-$d_6$, ppm): 13.2-12.6 (1H, br s) 8.33 (1H, d, J=8.6 Hz) 7.36-7.21 (17H, m) 7.04 (1H, dd, J=8.4, 2.0 Hz) 4.15-4.08 (1H, m) 2.78 (1H, dd, J=9.8, 12.5 Hz) 2.54 (1H, dd, J=12.5, 4.6 Hz) 1.30 (9H, s). ESI-MS (m/z): 537 [M+H]+.

Compound 10, as its HCl salt, was prepared in 70% yield from (R)-2-(5-tert-butylbenzoxazol-2-ylamino)-3-tritylsulfanyl-propionic acid using the general procedure described for compounds 4 and 6. 400 MHz $^1$H-NMR (DMSO-$d_6$, ppm): 12.0-11.6 (1H, br s) 10.5-9.9 (2H, br s) 7.27 (1H, dd, J=8.6, 2.5 Hz) 7.22 (1H, d, J=2.5 Hz) 6.98 (1H, d, J=8.6 Hz) 5.08-4.84 (1H, m) 3.99-3.85 (1H, m) 3.75-3.65 (1H, m) 1.24 (9H, s). ESI-MS (m/z): 295 [M+H]+.

Compound 12:

(R)-2-(1-Carboxy-2-tritylsulfanyl-ethylamino)-benzoxazole-6-carboxylic acid methyl ester was prepared from compound 11 in accordance with the procedures set forth for compounds 4 and 6. 400 MHz $^1$H-NMR (DMSO-$d_6$, ppm): 13.3-12.8 (1H, br s) 8.89 (1H, d, J=8.4 Hz) 7.90 (1H, d, J=1.4 Hz) 7.83 (1H, dd, J=8.4, 1.4 Hz) 7.36-7.18 (16H, m) 4.19-4.11 (1H, m) 3.84 (3H, s) 2.79 (1H, dd, J=12.6, 9.8 Hz) 2.56 (1H, dd, J=12.6, 9.8 Hz). ESI-MS (m/z): 539 M+H]+.

Compound 12, as its HCl salt, was prepared in 75% yield from (R)-2-(1-carboxy-2-tritylsulfanyl-ethylamino)-benzoxazole-6-carboxylic acid methyl ester according to the procedures set forth for compounds 4 and 6. 400 MHz 1H-NMR (DMSO-$d_6$, ppm) 11.9-10.2 (3H, br s) 7.62-7.57 (1H, m) 7.49-7.42 (2H, m) 4.96 (1H, dd, J=8.8, 3.5 Hz) 3.92-3.83 (1H, m) 3.84 (3H, s) 3.68 (1H, dd, J=11.5, 3.5 Hz). ESI-MS (m/z): 297 [M+H]+. Melting point: 118-120° C.

Compound 14:

(R)-2-(6-Ethanesulfonylbenzoxazol-2-ylamino)-3-tritylsulfanyl-propionic acid was prepared from compound 13 according to the general procedures specified for the preparation of compounds 4 and 6. 400 MHz $^1$H-NMR (DMSO-$d_6$, ppm): 8.69-8.59 (1H, m) 7.67 (1H, d, J=1.8 Hz) 7.63 (1H, d, J=8.2 Hz) 7.55 (1H, dd, J=8.2, 1.8 Hz) 7.37-7.18 (15H, m) 4.13-4.05 (1H, m) 3.28 (2H, q, J=7.4 Hz, overlapped with water) 2.76 (1H, dd, J=12.2, 9.2 Hz) 2.59 (1H, dd, J=12.2, 4.2 Hz) 1.09 (3H, t, J=7.4 Hz). ESI-MS (m/z): 573 [M+H]+.

Compound 14, as its HCl salt, was prepared in 33% yield from (R)-2-(6-ethanesulfonyl-benzoxazol-2-ylamino)-3-tritylsulfanyl-propionic acid as set forth for compounds 4 and 6. 400 MHz 1H-NMR (DMSO-$d_6$, ppm): 12.4-11.5 (2H, br s) 7.81-7.71 (1H, m) 7.69-7.59 (1H, m) 7.15 (1H, d, J=8.4 Hz) 4.94-4.87 (1H, m) 3.87-3.76 (1H, m) 3.68-3.60 (1H, m) 3.17 (2H, q, J=7.2 Hz) 1.06 (3H, t, J=7.2 Hz). ESI-MS (m/z): 331 [M+H]+.

Compound 16:

(R)-2-(6-Chlorobenzoxazol-2-ylamino)-3-tritylsulfanyl-propionic acid was prepared from compound 15 in accordance with the general procedures specified for compounds 4 and 6. 400 MHz $^1$H-NMR (DMSO-$d_6$, ppm): 8.50 (1H, d, J=8.4 Hz) 7.39 (1H, d, J=8.4 Hz) 7.33-7.19 (16H, m) 7.03 (1H, dd, J=8.4, 2.1 Hz) 4.13-4.06 (1H, m) 2.74 (1H, dd, J=12.4, 9.3 Hz) 2.55 (1H, dd, J=12.4, 4.6 Hz). ESI-MS (m/z): 515, 517 [M+H]+.

Compound 16 was prepared in 42% yield from (R)-2-(6-chlorobenzoxazol-2-ylamino)-3-tritylsulfanyl-propionic acid according to the general procedures described for compounds 4 and 6. 400 MHz $^1$H-NMR (DMSO-$d_6$, ppm): 12.0-10.4 (3H, br s) 7.46-7.37 (1H, m) 7.26-7.17 (1H, m) 7.02 (1H, d, J=8.6 Hz) 4.94 (1H, dd, J=8.4, 3.5 Hz) 3.91-3.80 (1H, m) 3.66 (1H, dd, J=11.5, 3.5 Hz). ESI-MS (m/z): 273, 275 [M+H]+.

Compound 18:

(R)-2-(5-Methoxybenzoxazol-2-ylamino)-3-tritylsulfanyl-propionic acid was prepared from compound 17 in accordance with the general procedures specified for compounds 4 and 6. 200 MHz $^1$H-NMR (DMSO-$d_6$, ppm): 8.36 (1H, d, J=8.6 Hz) 7.38-7.18 (16H, m) 6.86 (1H, d, J=2.6 Hz) 6.57 (1H, dd, J=8.8, 2.6 Hz) 4.17-4.02 (1H, m) 3.73 (3H, s) 2.75 (1H, dd, J=12.2, 9.9 Hz) 2.57-2.50 (1H, m, overlapped with DMSO). ESI-MS (m/z): 511 [M+H]$^+$.

Compound 18, as its HCl salt, was prepared in 48% yield from (R)-2-(5-methoxybenzoxazol-2-ylamino)-3-tritylsulfanyl-propionic acid using the general procedures described for the preparation of compounds 4 and 6. 400 MHz 1H-NMR (DMSO-$d_6$, ppm): 12.2-9.5 (3H, m) 6.92 (1H, d, J=8.8 Hz) 6.90-6.86 (1H, m) 6.83-6.76 (1H, m) 4.96-4.89 (1H, m) 3.90-3.83 (1H, m) 3.67 (3H, s) 3.68-3.63 (1H, m). ESI-MS (m/z): 269 [M+H]$^+$.

Compound 20:

Compound 19 (1.5 g, 8.3 mmol) and (S)-methyl 2-amino-3-mercapto-3-methylbutanoate (1.7 g, 8.5 mmol) were dissolved in 15 mL of DMF. Subsequently, DIPEA (2.9 mL) was added. The reaction mixture was stirred at r.t. for 3 h. The reaction was diluted with ethyl acetate (200 mL) washed with water (100 mL), saturated NH$_4$Cl solution (100 mL) and brine solution (50 mL). The organic phase was dried over Na$_2$SO$_4$, filtered and concentrated to give a black oil, which was then purified by silica-gel column chromatography (eluent: i-PrOH/PE=1:20) to give a pale yellow solid. The solid was recrystallized from ethyl acetate and heptane, giving compound 20 (725 mg, yield 27%, purity: 99%). $^1$H NMR (CDCl$_3$, 500 MHz): δ 6.96 (d, J=8.4 Hz, 1H), 6.95 (s, 1H), 6.96 (d, J=7.5 Hz, 1H), 4.43 (s, 1H), 3.82 (s, 3H), 1.73 (s, 3H), 1.47 (s, 3H). $^{13}$C NMR (CDCl$_3$, 125 MHz): δ 167.3, 160.3, 146.1, 123.1, 122.1, 118.6, 50.6, 26.3, 23.7. ESI-MS (m/z): 315.0 [M+1]$^+$.

Compound 21:

Compound 19 (1.65 g, 8.8 mmol) and D-penicillamine (1.40 g, 9.4 mmol) were dissolved in 10 mL of DMF. Subsequently, DIPEA (2.5 mL) was added. The resulting mixture was stirred at r.t. for 2 hours. The reaction was then diluted with water (200 mL) and washed with ethyl acetate (2×150 mL). The aqueous phase was concentrated and the residue was purified by prep-HPLC eluting with an H$_2$O/CH$_3$CN gradient containing 0.05% TFA to give (S)-2-(2-hydroxy-5-chlorophenylamino)-thiazoline-5,5-dimethyl-4-carboxylic acid as a white solid TFA salt (1.2 g, yield 45%, purity: 100%). $^1$H NMR (DMSO-d6, 400 MHz): δ 7.37 (s, 1H), 7.21 (d, J=8.0 Hz, 1H), 6.97 (d, J=8.4 Hz, 1H), 4.61 (brs, 1H), 1.70 (s, 3H), 1.49 (s, 3H); $^{13}$C NMR (DMSO-d6, 100 MHz): δ 168.6, 150.5, 128.3, 125.3, 122.1, 115.5, 113.3, 72.2, 57.4, 28.5, 24.7; ESI-MS (m/z): 301.0 [M+1]$^+$ Compound 23:

Compound 22 (668 mg, 4.0 mmol) and (S)-methyl 2-amino-3-mercapto-3-methylbutanoate hydrochloride (960 mg, 4.8 mmol) were dissolved in 10 mL of DMF. Subsequently, DIPEA (8.0 mL) was added. The mixture was stirred at r.t. overnight. The reaction was diluted with ethyl acetate (200 mL) and washed with water (100 mL). The organic phase was dried over Na$_2$SO$_4$, filtered, and concentrated in vacuo. The residue was purified by silica-gel column chromatography (eluent: ethyl acetate/petroleum ether: 1:3-1:1) to obtain compound 23.

The crude product was further purified by prep-HPLC eluting with an H$_2$O/CH$_3$CN gradient containing 0.05% TFA to get (S)-2-(2-hydroxy-5-methylphenylamino)-thiazoline-5,5-dimethyl-4-carboxylic acid methyl ester TFA salt (600 mg, yield 51%). $^1$H NMR (CDCl$_3$, 500 MHz): δ 6.92 (d, J=7.5 Hz, 1H), 6.71 (s, 1H), 6.56 (d, J=7.0 Hz, 1H), 4.58 (s, 1H), 3.84 (s, 3H), 2.20 (s, 3H), 1.73 (s, 3H), 1.50 (s, 3H); $^{13}$C NMR (CDCl$_3$, 125 MHz): δ 174.3, 166.6, 151.4, 140.8, 125.3, 121.7, 120.6, 118.1, 71.4, 57.5, 53.1, 28.5, 25.2, 21.2; ESI-MS (m/z): 295.1 [M+1]$^+$.

Compound 24:

Compound 22 (1.0 g, 6.0 mmol) and (S)-penicillamine (983 mg, 6.6 mmol) were dissolved in 5 mL of DMF. Subsequently, DIPEA (1.55 mL, 12 mmol) was added. The reaction was stirred at r.t. overnight. The mixture was concentrated and the resultant residue was purified by prep-HPLC eluting with an H$_2$O/CH$_3$CN gradient containing 0.05% TFA. The resultant product was recrystallized from MeOH and diethyl ether to give compound 24 as a salt. $^1$H NMR (DMSO-d6, 500 MHz): δ 6.99 (d, J=6.0 Hz, 1H), 6.61 (s, 1H), 6.54 (d, J=7.5 Hz, 1H), 4.39 (s, 1H), 2.18 (s, 3H), 1.63 (s, 3H), 1.40 (s, 3H); $^{13}$C NMR (DMSO-d6, 125 MHz): δ 170.8, 160.5, 148.5, 134.2, 127.5, 121.9, 119.6, 118.1, 77.0, 58.7, 28.1, 25.5, 20.4; ESI-MS (m/z): 281.1 [M+1]$^+$.

Compound 26:

Compound 25 (870 mg, 4.7 mmol) and D-penicillamine (710 mg, 4.7 mmol) were dissolved in DMSO (20 mL), and NaOH (430 mg, 10.7 mmol) was added. The reaction was stirred at r.t. for 3 h. The mixture was then acidified with 6N HCl (1.5 mL) to pH 3-4, then purified by flash chromatography eluting with acetonitrile/distilled water (with 0.05% TFA) giving compound 26 as a salt (1.0 g, 74%, purity: 97%). $^1$H NMR (DMSO-d6, 500 MHz): δ 6.97 (d, J=8.0 Hz, 1H), 6.37 (s, 1H), 6.34 (d, J=8.5 Hz, 1H), 4.38 (s, 1H), 3.66 (s, 3H), 1.63 (s, 3H), 1.40 (s, 3H); $^{13}$C NMR (DMSO-d6, 125 MHz): δ 170.5, 157.8, 151.0, 124.1, 122.3, 104.5, 103.0, 76.2, 58.7, 55.1, 27.7, 25.5; ESI-MS (m/z): 297.1 [M+1]$^+$.

Compound 27:

A solution of compound 26 (800 mg, 2.7 mmol) in MeOH (30 mL) was prepared. SOCl$_2$ (0.8 mL) was then added in a dropwise manner. The mixture was stirred overnight at r.t. The resulting solution was concentrated under reduced pressure to obtain the title compound as white solid compound 27 as its HCl salt (930 mg, 99%, purity: 95%). $^1$H NMR (DMSO-d6, 500 MHz): δ 11.7 (brs, 1H), 10.5 (brs, 1H), 7.12 (d, J=8.0 Hz, 1H), 6.37 (brs, 1H), 6.46 (brs, 1H), 4.74 (brs, 1H), 3.77 (s, 3H), 3.72 (s, 3H), 1.70 (s, 3H), 1.43 (s, 3H); $^{13}$C NMR (DMSO-d6, 125 MHz): δ 167.6, 160.2, 153.3, 127.5, 104.8, 102.2, 70.7, 57.0, 55.2, 52.6, 24.2; ESI-MS (m/z): 311.1 [M+1]$^+$.

Compound 28:

Compound 15 (693 mg, 3.7 mmol) and D-penicillamine (550 mg, 3.7 mmol) were dissolved in 4 mL of DMF. Subsequently DIPEA (960 mg, 7.5 mmol) was added. The reaction was stirred at r.t. for 3 h. The resultant mixture was concentrated and the crude product was purified by preparative HPLC eluting with an H$_2$O/CH$_3$CN gradient containing 0.05% TFA, giving compound 28 as a pink solid (652 mg, yield 58%). $^1$H NMR (DMSO-d6, 500 MHz): δ 7.17 (brs, 1H), 6.81-6.75 (m, 2H), 4.37 (s, 1H), 1.62 (s, 3H), 1.39 (s, 3H); $^{13}$C NMR (DMSO-d6, 125 MHz): δ 170.7, 159.4, 149.4, 127.2, 122.4, 118.7, 116.5, 28.3, 25.5; ESI-MS (m/z): 301.1 [M+1]$^+$ Compound 30:

To a solution of compound 29 (1.0 g, 5.0 mmol) in DMF (30 mL) was added D-penicillamine methyl ester (1.6 g, 10.0 mmol) and Na$_2$CO$_3$ (2.5 g, 19.8 mmol). The reaction was stirred at r.t. for 30 min. The resultant mixture was diluted with ethyl acetate (150 mL) and the resulting organic phase was washed with NH$_4$Cl solution, brine, dried over Na$_2$SO$_4$, filtered and concentrated in vacuo. The resultant crude product was purified by preparative HPLC eluting with an H$_2$O/

CH$_3$CN gradient containing 0.05% TFA to obtain (R)-2-(2-hydroxy-5-nitrophenylamino)-thiazoline-5,5-dimethyl-4-carboxylic acid methyl ester (850 mg, 50%). $^1$H NMR (CDCl$_3$, 500 MHz): δ 8.06 (s, 1H), 7.98 (d, J=9.0 Hz, 1H), 7.01 (d, J=9.0 Hz, 1H), 4.64 (s, 1H), 3.93 (s, 3H), 1.81 (s, 3H), 1.50 (s, 3H); $^{13}$C NMR (MeOD, 125 MHz): δ 173.6, 168.7, 159.5, 141.6, 126.9, 125.2, 123.8, 117.7, 73.0, 59.6, 53.5, 29.3, 25.1; ESI-MS (m/z): 326.1 [M+1]$^+$.

Compound 31:

Compound 29 (1.84 g, 9.3 mmol) and D-penicillamine (1.4 g, 9.3 mmol) were dissolved in DMF (5 mL). Subsequently DIPEA (2 mL) was added. The reaction mixture was stirred at r.t. overnight. The reaction was diluted with ethyl acetate (200 mL) and the solid was filtered off. The resultant organic phase was washed with water and the resulting aqueous phases were combined and concentrated. The resulting residue was purified by preparative HPLC eluting with an H$_2$O/CH$_3$CN gradient containing 0.05% TFA. Compound 31 was obtained as white solid (1.28 g, yield 45%, purity: 100%). $^1$H NMR (DMSO-d6, 500 MHz): δ 8.24 (brs, 1H), 8.05 (d, J=9.0 Hz, 1H), 7.09 (d, J=9.0 Hz, 1H), 4.59 (s, 1H), 1.70 (s, 3H), 1.49 (s, 3H); $^{13}$C NMR (MeOD, 125 MHz): δ 169.3, 158.3, 139.8, 124.5, 121.7, 118.4, 116.9, 115.5, 72.7, 57.8, 28.9, 25.3; ESI-MS (m/z): 312.0 [M+1]$^+$.

Compound 32:

Compound 13 (800 mg, 3.2 mmol) and D-penicillamine methyl ester (1.0 g, 6.1 mmol) were dissolved in DMF (20 mL). Na$_2$CO$_3$ (500 mg, 4.7 mmol) was subsequently added. The reaction was stirred at 0° C. for 2 h. The mixture was then diluted with ethyl acetate (100 mL) and subsequently washed with aqueous NH$_4$Cl (100 mL) and then with brine (50 mL). The organic phase was dried (NaSO$_4$) and concentrated. The resultant crude product was purified by silica gel chromatography (eluent: ethyl acetate/petroleum ether: 1:1 (v/v)) and the final product was recrystallized from ethyl acetate/petroleum ether giving compound 32 as a white solid (550 mg, 40%, 99% purity). $^1$H NMR (CDCl$_3$, 500 MHz): δ 7.53-7.52 (m, 2H), 7.98 (d, J=8.5 Hz, 1H), 4.44 (s, 1H), 3.84 (s, 3H), 3.08 (q, J=7.5 Hz, 2H), 1.75 (s, 3H), 1.48 (s, 3H), 1.26 (t, J=7.5 Hz, 3H); $^{13}$C NMR (MeOD, 125 MHz): δ 171.6, 164.0, 155.4, 129.6, 126.0, 122.7, 117.3, 52.7, 51.6, 49.0, 29.3, 25.9, 7.8; ESI-MS (m/z): 373.0 [M+1]$^+$.

Compound 33:

Compound 13 (2.0 g, 8.1 mmol) and D-penicillamine (1.22 g, 8.1 mmol) were dissolved in DMF (20 mL) and DIPEA (3.3 g, 32.6 mmol) was added. The reaction was stirred at 0° C. for 15 min. The mixture was then concentrated and the resultant crude product was purified by preparative HPLC eluting with an H$_2$O/CH$_3$CN gradient containing 0.05% TFA, giving compound 33 as a white solid (380 mg, 30%). $^1$H NMR (D$_2$O, 500 MHz): δ 7.82 (s, 1H), 7.76 (d, J=9.0 Hz, 1H), 7.19 (d, J=9.0 Hz, 1H), 3.26 (q, J=7.5 Hz, 2H), 1.70 (s, 3H), 1.51 (s, 3H), 1.49 (t, J=7.5 Hz, 3H); $^{13}$C NMR (MeOD, 125 MHz): δ 158.4, 134.4, 128.3, 118.3, 73.6, 59.5, 51.4, 29.0, 26.3, 7.7; ESI-MS (m/z): 359.0 [M+1]$^+$.

Compound 34:

Compound 34 was prepared from 2-chlorobenzoxazole and L-cysteine methyl ester following the procedure used to prepare compound 2.

Compound 35:

Compound 35 was prepared from 2-chlorobenzoxazole and D-penicillamine methyl ester according to the procedure described for compound 20.

Compound 36:

Compound 36 was prepared from 2,6-dichlorobenzoxazole (compound 15) and L-cysteine methyl ester following the procedure described for compound 20.

Compound 37:

Compound 37 was prepared from 2,6-dichlorobenzoxazole (compound 15) and D-penicillamine methyl ester according to the procedure described for compound 20.

Compound 38:

Compound 38 was prepared from 2,6-dichlorobenzoxazole (compound 15) and L-cysteine according to the procedure set forth for compound 21.

Compound 39:

Compound 39 was prepared from compound 2 according to the procedure set forth for compound 27.

Crystal Structure Data For Compound 6
Fractional Atomic Coordinates & U(ISO)

| Atom  | x/a         | y/b         | z/c         | U(iso)     |
|-------|-------------|-------------|-------------|------------|
| S(1)  | 0.0619(5)   | 0.89329(18) | 0.62592(5)  | 0.0443(10) |
| F(14) | −0.0622(11) | 0.41666(4)  | 0.46571(10) | 0.070(3)   |
| O(16) | −0.3230(12) | 1.0220(5)   | 0.79075(13) | 0.055(3)   |
| O(17) | −0.4006(12) | 1.1860(5)   | 0.73194(14) | 0.056(3)   |
| O(13) | 0.1024(13)  | 0.3833(5)   | 0.63281(14) | 0.068(3)   |
| N(6)  | −0.2559(14) | 0.6449(5)   | 0.64916(13) | 0.037(3)   |
| C(5)  | 0.0061(17)  | 1.0476(7)   | 0.66746(17) | 0.043(4)   |
| N(3)  | −0.2344(14) | 0.8374(5)   | 0.70441(14) | 0.037(3)   |
| C(2)  | −0.1638(15) | 0.7796(7)   | 0.66208(17) | 0.033(3)   |
| C(15) | −0.2837(18) | 1.0732(7)   | 0.7486(2)   | 0.041(4)   |
| C(4)  | −0.0713(16) | 0.9757(6)   | 0.71660(18) | 0.035(4)   |
| C(12) | −0.3366(17) | 0.6534(7)   | 0.56100(19) | 0.050(4)   |
| C(10) | −0.113(2)   | 0.4730(8)   | 0.5110(2)   | 0.054(5)   |
| C(7)  | −0.2030(17) | 0.5848(7)   | 0.60091(18) | 0.040(4)   |
| C(11) | −0.2924(18) | 0.5958(8)   | 0.51475(19) | 0.048(5)   |
| C(8)  | −0.0280(18) | 0.4573(6)   | 0.5958(2)   | 0.043(4)   |
| C(9)  | 0.0169(17)  | 0.3990(7)   | 0.54902(19) | 0.051(5)   |
| H(5A) | 0.22988     | 1.100461    | 0.665826    | 0.056664   |
| H(5B) | −0.16939    | 1.129391    | 0.655266    | 0.056664   |
| H(6)  | −0.42047    | 0.595765    | 0.66908     | 0.061308   |
| H(9)  | 0.136361    | 0.311578    | 0.542664    | 0.084648   |
| H(11) | −0.384011   | 0.641693    | 0.486906    | 0.068208   |
| H(12) | −0.459431   | 0.740398    | 0.566439    | 0.078816   |
| H(13) | 0.153817    | 0.41732     | 0.666581    | 0.143532   |
| H(3)  | −0.337489   | 0.773729    | 0.731041    | 0.059208   |
| H(4)  | 0.131722    | 0.957573    | 0.738132    | 0.04524    |

Temperature factor of the form: exp[−2π$^{2U}$], U=U(iso) or ⅓ SUM(i)SUM(j){U(ij)*astar(i).astar(j).a(i).a(j). cos(ij)}
Anisotropic Thermal Parameters

| Atom  | U11        | U22        | U33        | U12        | U13       | U23        |
|-------|------------|------------|------------|------------|-----------|------------|
| S(1)  | 0.0558(13) | 0.0428(10) | 0.0342(8)  | −.0013(10) | 0.0127(8) | −.0013(8)  |
| F(14) | 0.104(4)   | 0.072(3)   | 0.0354(18) | −.006(3)   | 0.011(2)  | −.0258(18) |
| O(16) | 0.079(4)   | 0.059(3)   | 0.026(2)   | 0.017(3)   | 0.012(2)  | 0.005(2)   |
| O(17) | 0.078(4)   | 0.049(3)   | 0.041(3)   | 0.025(3)   | 0.014(3)  | 0.004(2)   |
| O(13) | 0.120(5)   | 0.044(3)   | 0.041(2)   | 0.027(3)   | −.016(3)  | −.001(2)   |
| N(6)  | 0.051(4)   | 0.034(3)   | 0.027(2)   | −.004(3)   | 0.009(2)  | −.002(2)   |
| C(5)  | 0.047(5)   | 0.044(4)   | 0.038(3)   | 0.008(4)   | 0.017(4)  | −.001(3)   |
| N(3)  | 0.049(4)   | 0.036(3)   | 0.027(3)   | 0.009(3)   | 0.006(3)  | −.001(2)   |
| C(2)  | 0.037(5)   | 0.040(4)   | 0.023(3)   | −.003(3)   | 0.006(3)  | 0.003(3)   |

-continued

| Atom | U11 | U22 | U33 | U12 | U13 | U23 |
|---|---|---|---|---|---|---|
| C(15) | 0.041(5) | 0.041(4) | 0.040(4) | -.011(4) | 0.004(3) | -.013(3) |
| C(4) | 0.038(5) | 0.037(4) | 0.031(3) | -.001(4) | 0.004(3) | -.003(3) |
| C(12) | 0.066(6) | 0.050(4) | 0.033(3) | 0.001(4) | 0.005(3) | -.001(3) |
| C(10) | 0.084(7) | 0.055(4) | 0.022(3) | -.010(5) | 0.003(4) | -.009(3) |
| C(7) | 0.055(5) | 0.034(4) | 0.030(3) | -.013(4) | -.001(3) | -.001(3) |
| C(11) | 0.057(5) | 0.048(4) | 0.038(3) | -.003(5) | 0.001(3) | -.003(3) |
| C(8) | 0.057(6) | 0.030(4) | 0.041(3) | -.005(4) | 0.002(4) | -.004(3) |
| C(9) | 0.071(6) | 0.037(4) | 0.044(3) | -.002(5) | 0.004(4) | -.020(3) |

T = exp[2π2(U11.h2.astar2 + U22.k2.bstar2 + U33.l2.cstar**2 + 2U12.h.k.astar.bstar + 2U13.h.l.astar.cstar + 2U23.k.l.bstar.cstar)]

Intramolecular Bond Lengths
Minimum bond length=0.80 A: Maximum bond length=1.80 A

| S(1)—C(2) | 1.735(6) | F(14)—C(10) | 1.369(7) |
|---|---|---|---|
| O(16)—C(15) | 1.264(7) | O(17)—C(15) | 1.226(8) |
| O(13)—C(8) | 1.346(7) | N(6)—C(2) | 1.327(8) |
| N(6)—C(7) | 1.458(6) | C(5)—C(4) | 1.542(7) |
| N(3)—C(2) | 1.317(7) | N(3)—C(4) | 1.473(8) |
| C(15)—C(4) | 1.551(9) | C(12)—C(7) | 1.391(8) |
| C(12)—C(11) | 1.393(8) | C(10)—C(11) | 1.356(11) |
| C(10)—C(9) | 1.367(9) | C(7)—C(8) | 1.384(7) |
| C(8)—C(9) | 1.410(8) | O(16)—H(6) | 1.70(4) |
| O(16)—H(13) | 1.68(4) | O(17)—H(3) | 1.72(5) |
| O(13)—H(13) | 1.00(4) | N(6)—H(6) | 1.00(5) |
| C(5)—H(5A) | 1.08(7) | C(5)—H(5B) | 1.11(7) |
| N(3)—H(3) | 1.03(5) | C(4)—H(4) | 1.07(6) |
| C(12)—H(12) | 0.96(7) | C(11)—H(11) | 0.95(6) |
| C(9)—H(9) | 0.97(7) | | |

Intramolecular Bond Angles (H Omitted)
Minimum bond length=0.80 A: Maximum bond length=1.80 A

| C(2)—N(6)—C(7) | 122.6(5) | C(2)—N(3)—C(4) | 115.3(5) |
|---|---|---|---|
| S(1)—C(2)—N(6) | 123.8(4) | S(1)—C(2)—N(3) | 114.1(5) |
| N(6)—C(2)—N(3) | 122.1(5) | O(16)—C(15)—O(17) | 126.5(6) |
| O(16)—C(15)—C(4) | 113.5(5) | O(17)—C(15)—C(4) | 120.0(5) |
| C(5)—C(4)—N(3) | 105.0(4) | C(5)—C(4)—C(15) | 113.2(5) |
| N(3)—C(4)—C(15) | 109.0(5) | C(7)—C(12)—C(11) | 120.3(6) |
| F(14)—C(10)—C(11) | 117.8(5) | F(14)—C(10)—C(9) | 117.1(6) |
| C(11)—C(10)—C(9) | 125.2(6) | N(6)—C(7)—C(12) | 119.6(6) |
| N(6)—C(7)—C(8) | 119.2(5) | C(12)—C(7)—C(8) | 121.1(5) |
| C(12)—C(11)—C(10) | 117.0(6) | O(13)—C(8)—C(7) | 124.4(5) |
| O(13)—C(8)—C(9) | 117.0(5) | C(7)—C(8)—C(9) | 118.6(5) |
| C(10)—C(9)—C(8) | 117.8(6) | | |

Intramolecular Torsion Angles (H Omitted)
Minimum bond length=0.80 A: Maximum bond length=1.80 A

| Bonds | Angles |
|---|---|
| C(7)—N(6)—C(2)—S(1) | -6.6(4) |
| C(2)—N(6)—C(7)—C(12) | -62.8(7) |
| C(4)—N(3)—C(2)—S(1) | -9.3(4) |
| C(2)—N(3)—C(4)—C(5) | 27.2(5) |
| S(1)—C(2)—N(6)—C(7) | -6.6(4) |
| N(6)—C(2)—N(3)—C(4) | 169.8(8) |
| O(16)—C(15)—C(4)—C(5) | -173.3(8) |
| O(17)—C(15)—C(4)—C(5) | 8.3(6) |
| C(5)—C(4)—N(3)—C(2) | 27.2(5) |
| C(5)—C(4)—C(15)—O(17) | 8.3(6) |
| N(3)—C(4)—C(15)—O(17) | -108.1(7) |
| C(11)—C(12)—C(7)—N(6) | -178.9(9) |
| C(11)—C(12)—C(7)—C(8) | -0.9(6) |
| F(14)—C(10)—C(9)—C(8) | 178.7(9) |

| Bonds | Angles |
|---|---|
| C(11)—C(10)—C(9)—C(8) | -2.5(7) |
| N(6)—C(7)—C(12)—C(11) | -178.9(9) |
| C(8)—C(7)—N(6)—C(2) | 119.2(8) |
| C(12)—C(7)—C(8)—O(13) | -178.5(10) |
| C(12)—C(7)—C(8)—C(9) | 1.0(6) |
| C(10)—C(11)—C(12)—C(7) | -0.7(6) |
| O(13)—C(8)—C(7)—N(6) | -0.5(5) |
| O(13)—C(8)—C(9)—C(10) | -179.8(9) |
| C(9)—C(8)—C(7)—C(12) | 1.0(6) |
| C(8)—C(9)—C(10)—F(14) | 178.7(9) |
| C(10)—C(9)—C(8)—C(7) | 0.7(6) |
| C(7)—N(6)—C(2)—N(3) | 174.4(9) |
| C(2)—N(6)—C(7)—C(8) | 119.2(8) |
| C(4)—N(3)—C(2)—N(6) | 169.8(8) |
| C(2)—N(3)—C(4)—C(15) | 148.7(7) |
| S(1)—C(2)—N(3)—C(4) | -9.3(4) |
| N(3)—C(2)—N(6)—C(7) | 174.4(9) |
| O(16)—C(15)—C(4)—N(3) | 70.2(6) |
| O(17)—C(15)—C(4)—N(3) | -108.1(7) |
| C(5)—C(4)—C(15)—O(16) | -173.3(8) |
| N(3)—C(4)—C(15)—O(16) | 70.2(6) |
| C(15)—C(4)—N(3)—C(2) | 148.7(7) |
| C(7)—C(12)—C(11)—C(10) | -0.7(6) |
| F(14)—C(10)—C(11)—C(12) | -178.7(10) |
| C(9)—C(10)—C(11)—C(12) | 2.5(7) |
| C(12)—C(7)—N(6)—C(2) | -62.8(7) |
| N(6)—C(7)—C(8)—O(13) | -0.5(5) |
| N(6)—C(7)—C(8)—C(9) | 178.9(9) |
| C(8)—C(7)—C(12)—C(11) | -0.9(6) |
| C(12)—C(11)—C(10)—F(14) | -178.7(10) |
| C(12)—C(11)—C(10)—C(9) | 2.5(7) |
| O(13)—C(8)—C(7)—C(12) | -178.5(10) |
| C(9)—C(8)—C(7)—N(6) | 178.9(9) |
| C(7)—C(8)—C(9)—C(10) | 0.7(6) |
| C(10)—C(9)—C(8)—O(13) | -179.8(9) |
| C(8)—C(9)—C(10)—C(11) | -2.5(7) |

Intermolecular Non-Bonded Distances (H Omitted)
Minimum distance=1.95 A: Maximum distance=3.50 A

| Atom(1)-Atom(2) | Distance | ns | np | Ta | Tb | Tc | x(2) | y(2) | z(2) |
|---|---|---|---|---|---|---|---|---|---|
| S(1)—F(14) | 3.466(4) | 3 | 1 | 0 | 1 | 1 | 0.43782 | 1.08343 | 0.53429 |
| F(14)—C(9) | 3.406(8) | 3 | 1 | −1 | 0 | 1 | −0.48312 | 0.10096 | 0.45098 |
| O(16)—O(17) | 3.319(6) | 4 | 1 | −1 | −1 | 1 | −0.59944 | 0.68598 | 0.76806 |
| O(16)—O(13) | 2.635(6) | 4 | 1 | 0 | 0 | 1 | −0.10236 | 0.8833 | 0.86719 |
| O(16)—N(6) | 2.706(7) | 4 | 1 | −1 | 0 | 1 | −0.74411 | 1.14494 | 0.85084 |
| O(16)—N(6) | 3.207(7) | 4 | 1 | 0 | 0 | 1 | 0.25589 | 1.14494 | 0.85084 |
| O(16)—N(3) | 3.434(7) | 4 | 1 | −1 | 0 | 1 | −0.76558 | 1.33737 | 0.79559 |
| O(16)—C(2) | 3.471(8) | 4 | 1 | −1 | 0 | 1 | −0.83615 | 1.27955 | 0.83792 |
| O(16)—C(2) | 3.399(8) | 4 | 1 | 0 | 0 | 1 | 0.16385 | 1.27955 | 0.83792 |
| O(17)—C(5) | 3.370(8) | 1 | 1 | −1 | 0 | 0 | −0.99394 | 1.04756 | 0.66746 |
| O(17)—N(3) | 2.732(7) | 4 | 1 | −1 | 0 | 1 | −0.76558 | 1.33737 | 0.79559 |
| O(17)—C(4) | 3.498(8) | 1 | 1 | −1 | 0 | 0 | −1.07126 | 0.97567 | 0.7166 |
| O(13)—C(5) | 3.203(8) | 1 | 1 | 0 | −1 | 0 | 0.00606 | 0.04756 | 0.66746 |
| N(3)—C(15) | 3.424(8) | 4 | 1 | −1 | −1 | 1 | −0.7163 | 0.57321 | 0.75135 |
| S(1)—F(14) | 3.466(4) | 3 | 1 | 0 | 1 | 1 | 0.43782 | 1.08343 | 0.53429 |
| F(14)—C(9) | 3.406(8) | 3 | 1 | −1 | 0 | 1 | −0.48312 | 0.10096 | 0.45098 |
| O(16)—O(17) | 3.319(6) | 4 | 1 | −1 | −1 | 1 | −0.59944 | 0.68598 | 0.76806 |
| O(16)—O(13) | 2.635(6) | 4 | 1 | 0 | 0 | 1 | −0.10236 | 0.8833 | 0.86719 |
| O(16)—N(6) | 2.706(7) | 4 | 1 | −1 | 0 | 1 | −0.74411 | 1.14494 | 0.85084 |
| O(16)—N(6) | 3.207(7) | 4 | 1 | 0 | 0 | 1 | 0.25589 | 1.14494 | 0.85084 |
| O(16)—N(3) | 3.434(7) | 4 | 1 | −1 | 0 | 1 | −0.76558 | 1.33737 | 0.79559 |
| O(16)—C(2) | 3.471(8) | 4 | 1 | −1 | 0 | 1 | −0.83615 | 1.27955 | 0.83792 |
| O(16)—C(2) | 3.399(8) | 4 | 1 | 0 | 0 | 1 | 0.16385 | 1.27955 | 0.83792 |
| O(17)—C(5) | 3.370(8) | 1 | 1 | −1 | 0 | 0 | −0.99394 | 1.04756 | 0.66746 |
| O(17)—N(3) | 2.732(7) | 4 | 1 | −1 | 0 | 1 | −0.76558 | 1.33737 | 0.79559 |
| O(17)—C(4) | 3.498(8) | 1 | 1 | −1 | 0 | 0 | −1.07126 | 0.97567 | 0.7166 |
| O(13)—C(5) | 3.203(8) | 1 | 1 | 0 | −1 | 0 | 0.00606 | 0.04756 | 0.66746 |
| N(3)—C(15) | 3.424(8) | 4 | 1 | −1 | −1 | 1 | −0.7163 | 0.57321 | 0.75135 | ns is the symmetry operator number–(* denotes inversion indicator)
np is the lattice point number
Ta, Tb, & Tc are unit cell translations. The symmetry operations are:

$+X, +Y, +Z$      1

$½−X, −Y, ½+Z$      2

$½+X, ½−Y, −Z$      3

$−X, ½+Y, ½−Z$      4

Biological Examples

Animals: Experiments were performed on adult male Sprague-Dawley rats (Harlan, Indianapolis, Ind., USA) with implanted jugular vein catheter (JVC), weighing 250-300 grams, housed individually per cage with a 12 hour light: 12 hour dark cycle at constant room temperature 21±2° C. Animals had access to food and water ad libitum.

Compounds: Fentanyl citrate (Hospira, Lake Forest, Ill., USA) was administered intravenously. The compounds of the invention were administered intravenously.

Nociceptive testing/Thermal sensitivity: Antinociception was assayed using the tail flick assay (Model IITC 33(T), IITC Life Science, Woodland Hills, Calif., USA), in which a beam of light was focused on the dorsal surface of the rat tail, approximately 5 cm from the tip of the tail. The intensity of the light was adjusted so the baseline latency was 2-4 seconds. Cutoff time was set to 12 seconds in order to prevent any tissue damage. All testing was conducted by an experimenter who was unaware of the treatment of an individual rat.

Experimental paradigm A: This study was designed to evaluate the effect of the compounds of the invention on augmentation of fentanyl response. Prior to the beginning of the experiment, base line latency values were established to withdrawal time between 2-3 seconds. Animals received a treatment compound of the invention or the vehicle fifteen minutes before the first fentanyl (25 µg/kg, IV) administration, via pre-implanted jugular vein catheter (JVC). Tail flick latency values were recorded at 60, 120 and 180 minutes post first fentanyl administration. Second fentanyl administration was administered 210 minutes post first fentanyl administration, via JVC route. Tail flick latency's were recorded at 30, 60, 90, 120 and 150 minutes post second fentanyl administration.

Experimental paradigm B: This study was design to evaluate the effect of the compounds of the invention on augmentation of fentanyl response, mimicking a clinical setting. Prior to the beginning of the experiment, base line latency's were established to withdrawal time between 2-3 seconds. Animals received a treatment compound of the invention or the vehicle fifteen minutes prior to the first fentanyl (25 µg/kg, IV) administration, via pre-implanted jugular vein catheter (JVC). Multiple doses of fentanyl (10 µg/kg, IV) were administrated respectively to both groups at 75, 135, 195 minutes post first fentanyl administration. Last fentanyl (25 µg/kg, IV) administration was given right after 240 min post first fentanyl (25 µg/kg, IV) administration, Tail flick latency's were recorded at 30, 60, 90, 120, 150, 180, 210, and 240 min post first fentanyl administration.

Data analysis: Data analysis was preformed using Graph-Pad Prism software, where latency of withdraw from heat stimuli was compared between the vehicle and treated groups. The data was graphed and analyzed as percent of Possible Maximum Effect (% MPE=[(postinjection TFL−baseline TFL)/(12−baseline TFL)×100). Animals whose baseline latency (baseline: latency of withdraw prior to administration of drug or vehicle) withdraw was more than 6 seconds were excluded from the study. Two way analysis of variance (ANOVA), with Benferroni correction for multiple comparisons was used to determine statistical significance ($p<0.05$) at the different time points.

Analysis of compound activity: Two different methods were utilized to assess activity of the compounds of the invention, and generate SAR values.

1. Response Area Analysis: Analysis was based on deriving the value representing the % of the maximum possible response for the time periods under question. For example, the maximum possible value for 5% MPE time-points=5×100=500. For a rat with maximal possible effect (% MPE) scores of 100, 75, 50, 25 and 10 for the time-points, T30, T60, T90, T120 and T150, the total score or SUM=260. This value was (260/500)×100=52% of maximum=% MAX. This value was calculated for every single subject in the group. Mean and standard error was calculated for the groups, and one way analysis of variance (ANOVA), with Benferroni correction for multiple comparisons were used to determine statistical significance.

2. Regression analyses to evaluate time to half maximal response: To generate time to half maximal response, the data was converted to % change from the baseline, and time points were converted to log ten values. Regression analysis was performed on each subject in the group and time to half maximal response was generated. The differences between mean values of the groups was determined by running a one-way analysis of variance (ANOVA) and using the Error Mean Square term from the ANOVA, with the Bonferroni correction for multiple comparisons between means.

Experimental Example 1

Inhibition of Peroxynitrite Oxidation By Compounds of the Invention

Luminol like compound "L-012" is a chemilumescent probe that is activated by the presence of a ROS and/or RNS such as peroxynitrite. In this assay L-012 was oxidized by the addition of 3-Morpholino-sydnonimine ("SIN-1"), a known peroxynitrite generator. The emitted fluorescence was directly proportional to the concentration of SIN-1. The compounds of the invention were then assessed for their ability to scavenge peroxynitrite by blocking the increase of peroxynitrite induced fluorescence. Concentrations of compound producing 50% inhibition of the fluorescence signal ($IC_{50}$ values) were calculated by testing the compounds of the invention at various concentrations and averaging the $IC_{50}$ of three plates.

L-012 Assay Protocol

The following solutions were added to white polystyrene, non-sterile 96-well plate (Costar #3912): 196 μL of 50 μM L-012; 2 μL of the test compound; and 24 μL of 500 mM SIN-1. Fresh stock of 50 μM L-012 in PBS pH 7.4 was made for each 96 well plate that was analyzed. The plates were read in a FlexStation3 (Molecular Devices) using the luminescent mode at 37° C. for 30 min, with a measurement every 30 seconds and an integration time of 100 msec.

L-012 Data Collection and Analysis

Luminescence signal was recorded by the FlexStation3 kinetically at 37° C. for 30 minutes, with a measurement every 30 seconds and an integration time of 100 msec. The data in rows A and H were dropped from each plate to exclude the possibility of an 'edge effect'. Thus, each test compound had 3 replicates per plate. The 15 minute data time point was plotted to determine % control value or IC50 for follow-up concentration-response curves (Table 2).

TABLE 2

In vitro Inhibition of SIN-1 Generated Peroxynitrite Induced Fluorescence of L-012 by Compounds of the Invention.

| Compound | Average $IC_{50}$ (uM) | standard dev | n |
|---|---|---|---|
| 2 | 0.13 | 0.02 | 3 |
| 26 | 0.14 | 0.01 | 3 |
| 21 | 0.26 | 0.02 | 3 |
| 1 | 0.27 | 0.01 | 3 |
| 27 | 0.30 | 0.03 | 3 |
| 24 | 0.54 | 0.12 | 3 |
| 20 | 0.55 | 0.08 | 3 |

Experimental Example 2

Inhibition of Peroxynitrite Mediated Cytotoxicity

ATPlite is an Adenosine TriPhosphate monitoring system based on firefly luciferase. ATP monitoring was used as a measure of PC12 cell viability, as it is present in all metabolically active cells and its concentration very rapidly declines as cells undergo necrosis and apoptosis. ATPlite is based upon the production of light given off during the reaction of ATP & D-Luciferin in the presence of Luciferase. The emitted light is proportional to the ATP concentration. Compounds of the invention were assessed for their ability to inhibit SIN-1 induced cell toxicity. Inhibitory concentrations, $IC_{50}$ values, were calculated by testing compounds of the invention at various concentrations and averaging the $IC_{50}$ of two plates.

Cell Preparation

All cell work was carried out under the cell culture hood in a sterile environment. On Day 1, rat pheochromocytoma cells (PC12) cells were dissociated from T75 flasks with 0.25% trypsin/EDTA for approximately 2 minutes. Cells were harvested by adding 10 mL of F12K media to each flask and collecting cells into a sterile 15 mL conical tube. From this, 10 μL of cells were placed into 90 μL of trypan blue in a 1.5 mL microfuge tube. This was equal to a dilution factor of 10. The microfuge tube was mixed via vortex briefly and 10 μL was added into one side of a hemacytometer. The cells were counted in the 4 large corner quadrants of the hemacytometer under the inverted microscope at 10× and the average of the 4 quadrants was calculated. Blue cells were not counted as these cells represented non-viable cells. The number of cells present in 1 mL of media was determined using the following equation: cells/mL=(# cells counted/# squares counted)×$10^4$×dilution factor. (For example: $2.5 \times 10^6$ cells/mL=(100 cells/4 squares)×10000×10). Harvested cells were diluted in F12K media containing high serum (10% horse serum, 5% fetal bovine serum, 1% penicillin streptomycin) so that there were 300,000 cells in 1 mL. From this, 100 μL of cells/media were added to a sterile, clear-bottom collagen-coated 96-well plate (30,000 cells/well). The cells were allowed to attach overnight at 37° C., 5% $CO_2$.

Inhibition of Peroxynitrite Mediated Cytotoxicity—Protocol

All cell work is carried out under the cell culture hood in a sterile environment. On Day 2, media was removed from each plate and replaced with 100 μl of F12K containing low serum (1% horse serum, 1% penicillin streptomycin). To test the concentration-response of compounds of the invention, serial dilutions of these compounds of 5 mM down to 0.02 mM were prepared in PBS. Each dilution (2 μl volume) was added to the appropriate wells in quadruplicate. Test compounds were incubated on the cells at 37° C. before adding 2 μl of 50 mM SIN-1. The cells were then incubated overnight at 37° C.

On Day 3, 10.25 ml of ATPlite buffer was added to 1 vial of lyophilized substrate solution (ATPlite 1 step luminescence ATP detection Assay system (Perkin Elmer, #6016731)). To each plate, 100 µl/well of lyophilized solution was added and mixed on an orbital plate shaker for 2 min at 250 rpm. The plate was read within 5 min the FlexStation3 in luminescence mode.

Cell Based Data Analysis:

Luminescence signal was recorded by the FlexStation3 and percent of control was calculated. The wells containing only cells were used to calculate 100% of control, wells containing only SIN-1 was used to calculate 0%. The remaining data was plotted as % of control by subtracting the average of the SIN-1 controls and dividing by the 100% control value (Table 3).

TABLE 3

Inhibition of SIN-1 Cytotoxicity

| Compound | Average IC50(uM) | Standard dev | n |
|---|---|---|---|
| 2 | 3.7 | 0.80 | 2 |

Experimental Example #3:

Preservation of Fentanyl Analgesia in Rat Tail Flick Assay

A rat tail flick assay was conducted to assess the effect of compound 2 on analgesia induced by fentanyl. The first group of rats was injected intravenously with a compound and then 15 minutes later was injected with fentanyl (25 µg/kg). The second group of rats was injected intravenously with fentanyl (25 µg/kg) only. At 60, 120 and 180 minutes post-fentanyl administration, tail-flick latency values were obtained for both groups and recorded. After a period of 30 minutes (210 total minutes from the first administration of fentanyl), a second dose of fentanyl was given to both groups and at 30, 60, 90, 120 and 180 minutes following the fentanyl injection, tail-flick latency (TFL) was measured. The percentage of the maximal possible effect (% MPE), calculated as [(post-injection TFL−baseline TFL)/(12-baseline TFL)×100] was obtained FIG. 1.

Experimental Example #4

Preservation of Fentanyl Analgesia in Hargreaves Thermal Plantar Model

Figure 2:
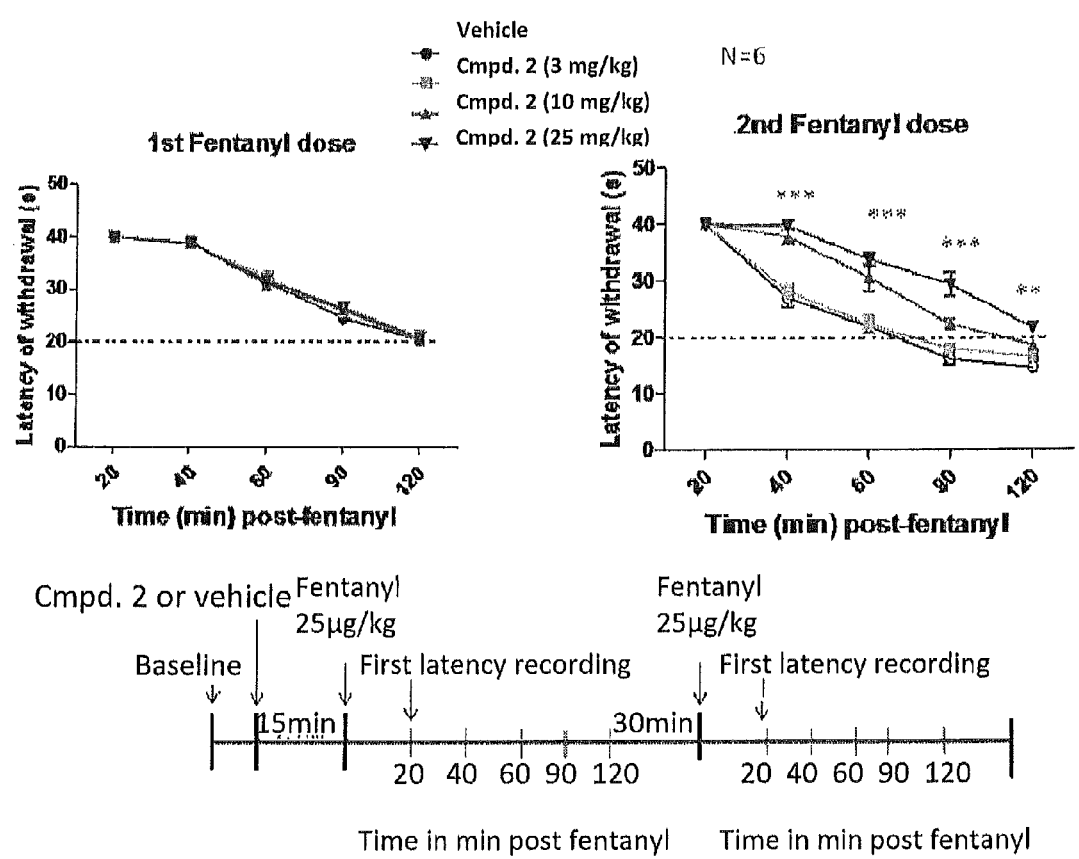
FIG. 2 depicts the results of an example experiment demonstrating that compound 2 dose-dependently preserves fentanyl analgesia in Hargreaves thermal hyperalgesia model.

A plantar assay measuring paw withdrawal to a high-intensity thermal light beam, the so-called Hargreaves endpoint (see Hargreaves et al., 1988, Pain 32:77-88), was conducted to assess the effect of compound 2 on analgesia induced by fentanyl. The first group of rats was injected intravenously with compound 2 and then 15 minutes later was injected with fentanyl (25 µg/kg). The second group of rats was injected intravenously with fentanyl (25 µg/kg) only. At 20, 40, 60, 90 and 120 minutes post-fentanyl administration, paw withdrawal latency (PWL) values were obtained for both groups and recorded. After a period of 30 minutes (150 total minutes from the first administration of fentanyl), a second dose of fentanyl (25 µg/kg) was given to both groups and PWL values were obtained at 20, 40, 60, 90 and 120 minutes post-fentanyl administration. This data is represented graphically in FIG. 2.

Experimental Example #5

Opioid Dose-Sparing

Figure 3:
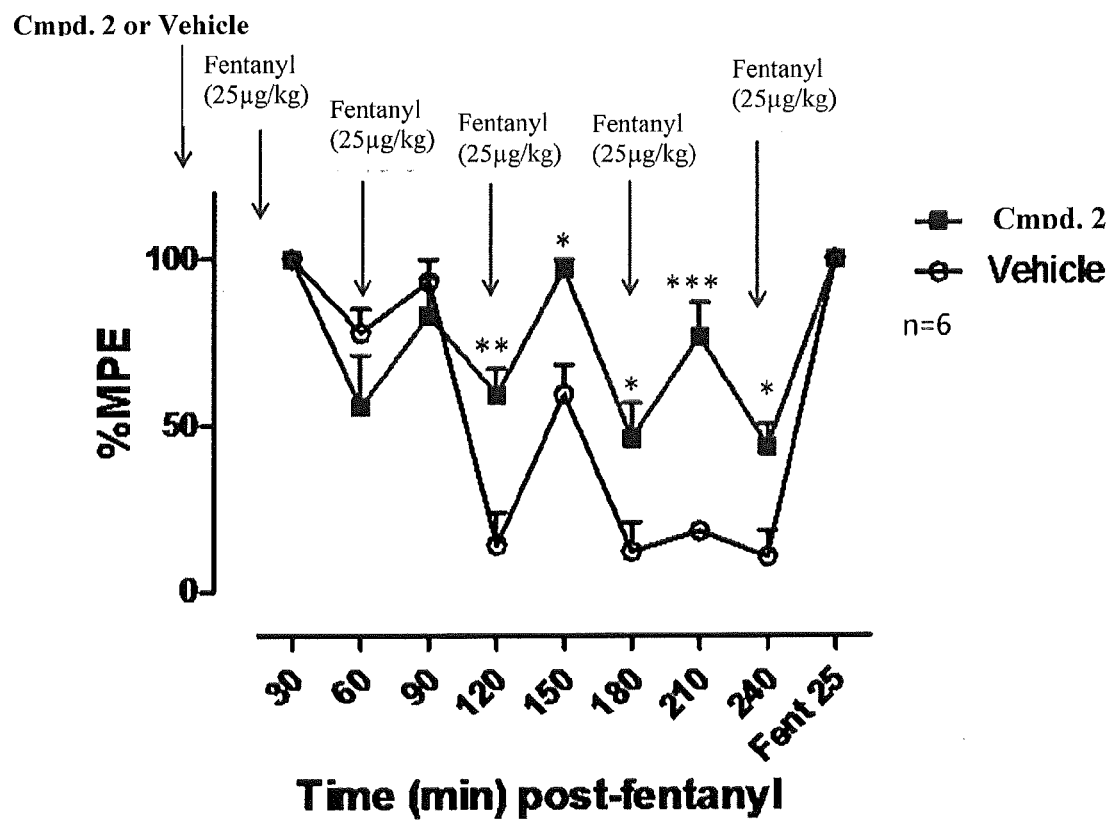
FIG. 3 depicts the results of an example experiment demonstrating that compound 2 preserves fentanyl analgesia, allowing smaller doses of fentanyl to elicit full or significant analgesia in rat as measured by Hargreaves thermal endpoints. Vehicle or Compound 2 (25 mg/kg, IV) were given 15 min before fentanyl. Multiples doses of fentanyl given to both groups at times indicated.

Compound 2 was administered in conjunction with an opioid dosing regimen designed to simulate patient controlled analgesia wherein small doses of analgesic are administered on-demand by patients follow a loading dose. In this experiment, vehicle or compound 2 were given to rats prior to five doses of fentanyl given hourly as depicted in FIG. 3, and paw withdrawal latencies values were obtained and used to calculate % MPE. Significant levels of analgesia were maintained in the drug treated group indicating that lower doses were required to maintain analgesia.

Experimental Example #6

Duration of Action of Compound 2

Figure 4:
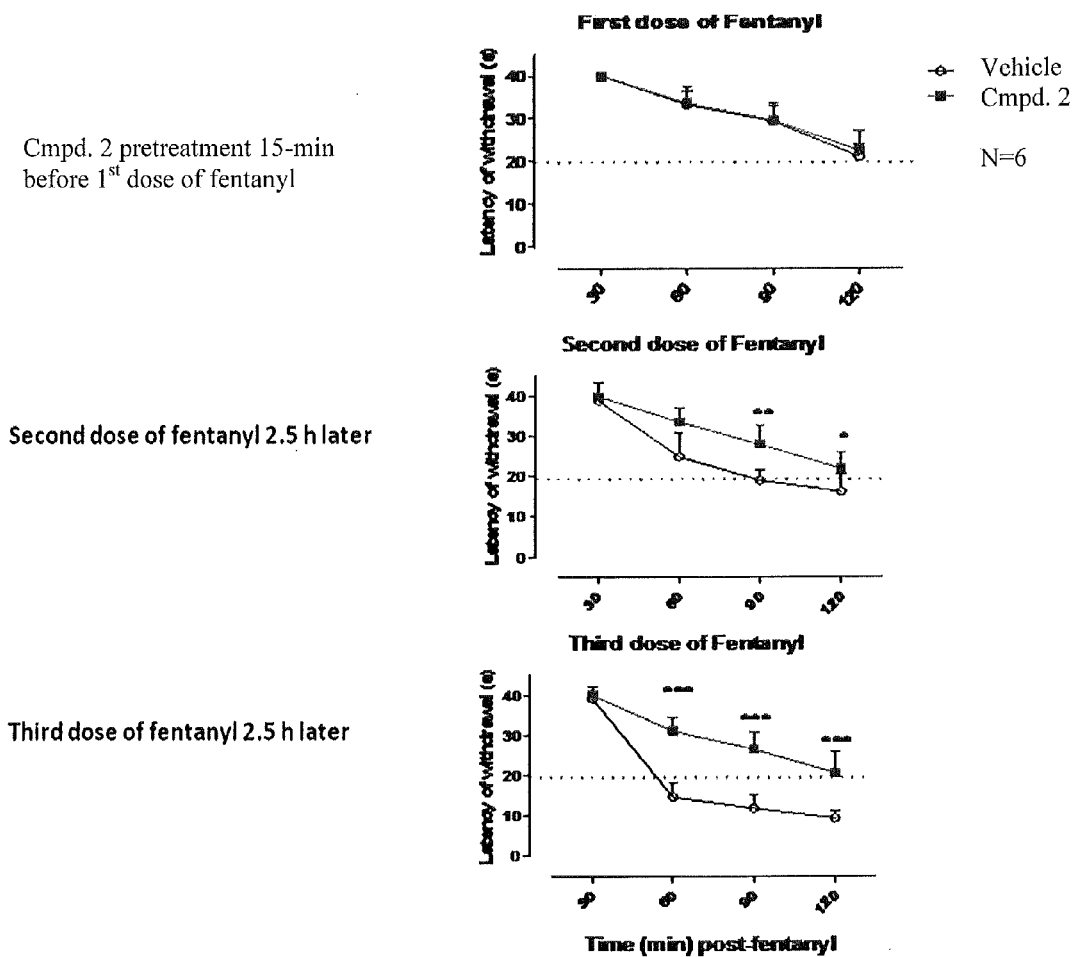
FIG. 4 depicts the results of an example experiment demonstrating that a single dose of compound 2 preserves fentanyl analgesia and blocks hyperalgesia even after three doses of fentanyl.

After a single IV dose of compound 2 in a rat, latency values were obtained at 30, 60, 90, and 120 minutes after each of three doses of fentanyl (25 µg/kg) separated by 2.5 hours (FIG. 4).

Experimental Example #7

Duration of Action of Compound 2

Figure 5:
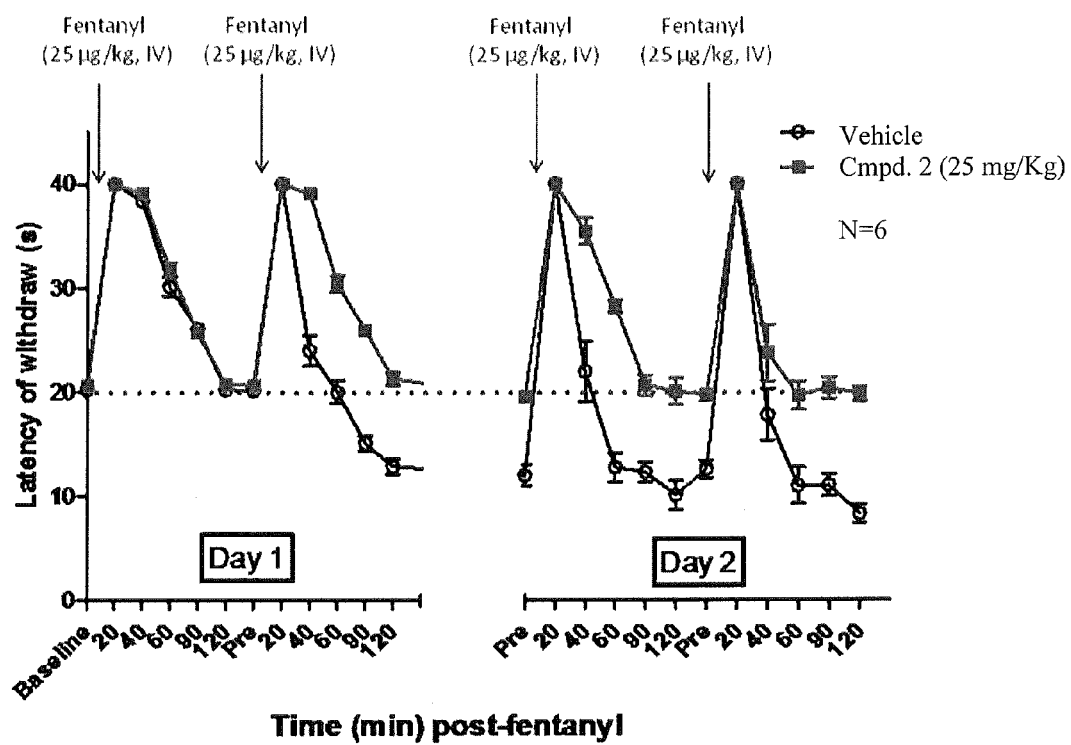
FIG. 5 depicts the results of an example experiment demonstrating that a single dose of compound 2 preserves fentanyl analgesia and inhibits development of hyperalgesia even after four doses of fentanyl.

After a single IV dose of compound 2 in a rat, latency values were obtained at 30, 60, 90, and 120 minutes after each of two daily doses of fentanyl (25 µg/kg). On the second day, two subsequent daily doses of fentanyl were given in an identical fashion as on day 1, but no additional compound 2 was administered (FIG. 5).

Experimental Example #8

Duration of Action of Compound 2

Figure 6:
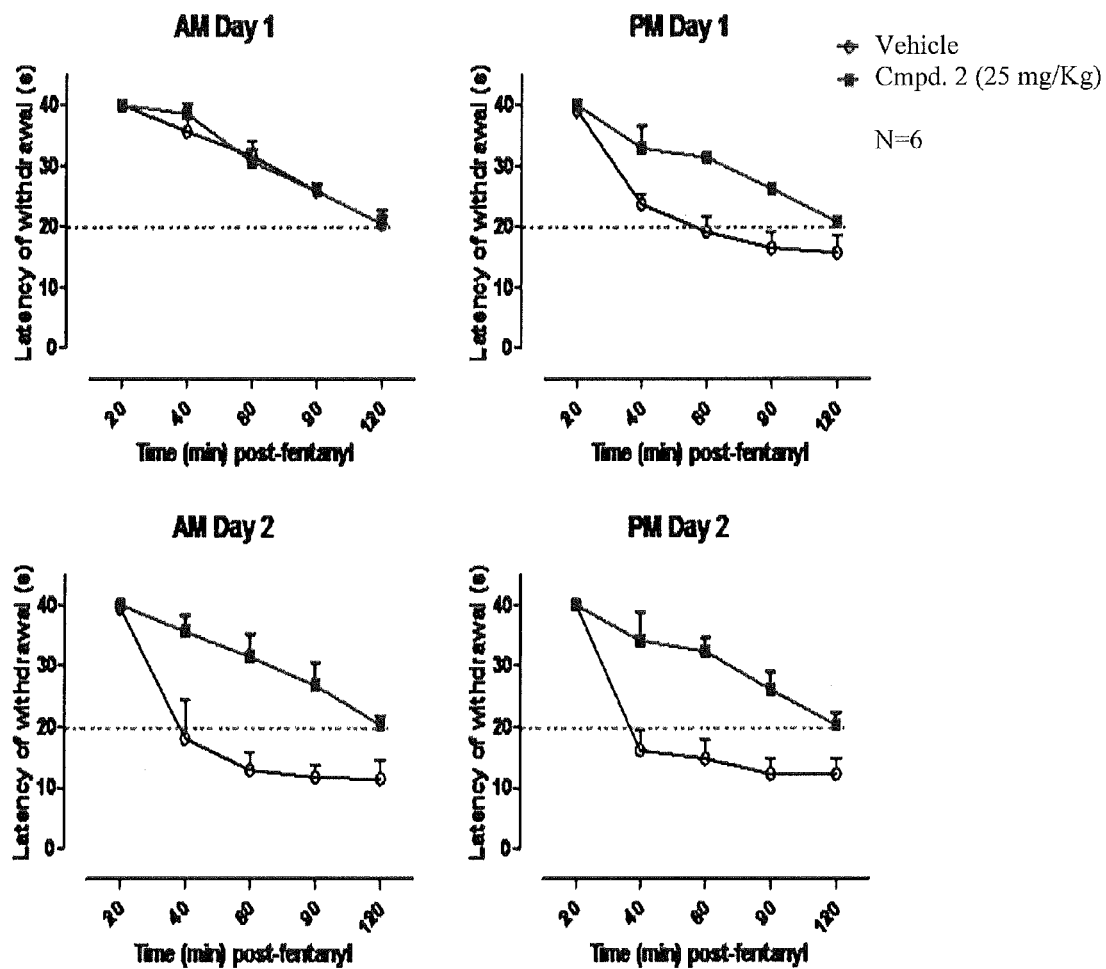
FIG. 6 depicts the results of an example experiment demonstrating that compound 2 preserves fentanyl analgesia by reducing tolerance and inhibiting hyperalgesia.

After a single IV dose of compound 2 in a rat, latency values were obtained at 20, 40, 60, 90, and 120 minutes after doses of fentanyl (25 µg/kg) given daily for four days (FIG. 6).

Experimental Example #9

Effects of Compound 2 on Existing Opioid Tolerance/Hyperalgesia

Figure 7:
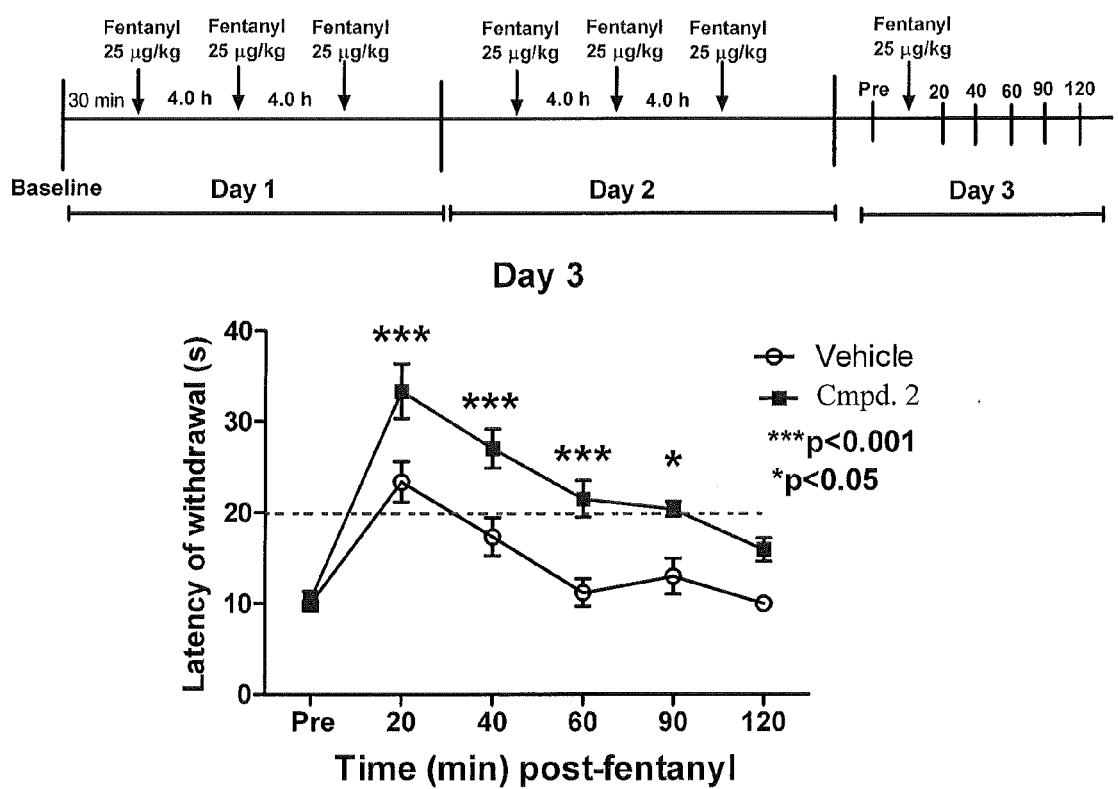
FIG. 7 depicts the results of an example experiment demonstrating that compound 2 attenuates established opioid-induced tolerance/hyperalgesia.

Rats were treated with three doses of fentanyl for two days as depicted in FIG. 7. On day 3, vehicle or a single IV dose of compound 2 was given to a rat after fentanyl challenge and latency values were obtained at 20, 40, 60, 90, and 120 minutes. This data shows that compounds of the invention can reverse pre-established opioid tolerance/hyperalgesia.

Experimental Example #10

Effect of Compound 2 on Capsaicin-Induced Hyperlagesia

Figure 8:
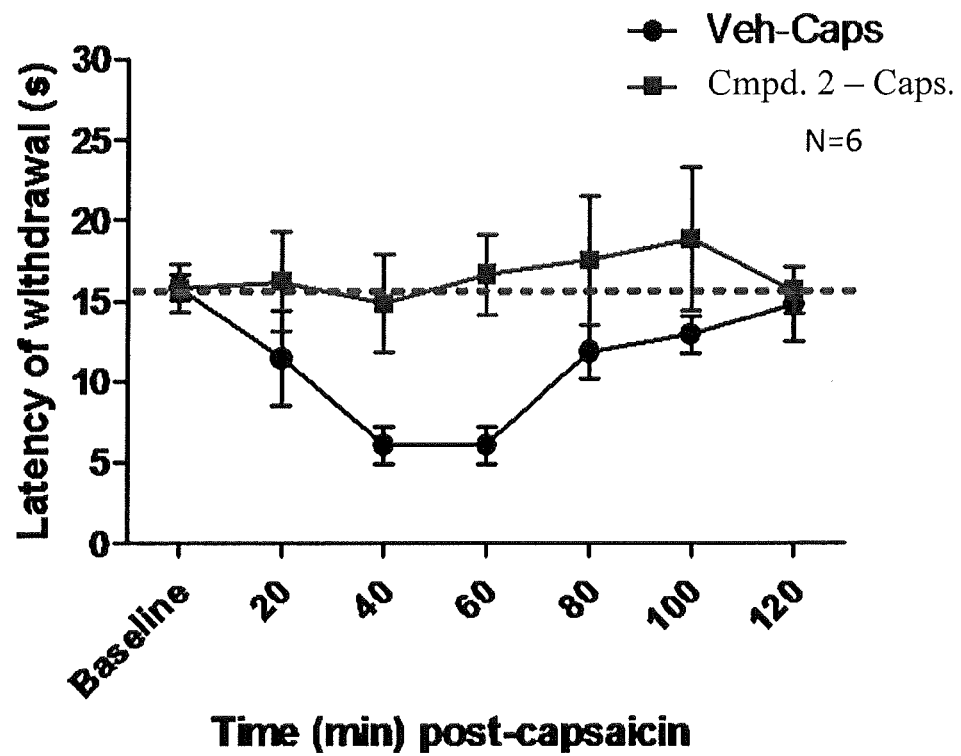
FIG. 8 depicts the results of an example experiment demonstrating that compound 2 inhibits capsaicin-mediated hyperalgesia.

Rats were given compound 2 IV prior to an intra-plantar administration of capsaicin, and withdrawal latencies were measured. This data, depicted graphically in FIG. 8, shows that compounds of the invention can prevent the development of hyperalgesic pain states produced by activation of primary afferent sensory neurons that express the TRPV1 receptor/channel.

Experimental Example #11

Effect of Compound 2 on Incisional Hyperlagesia

Figure 9:
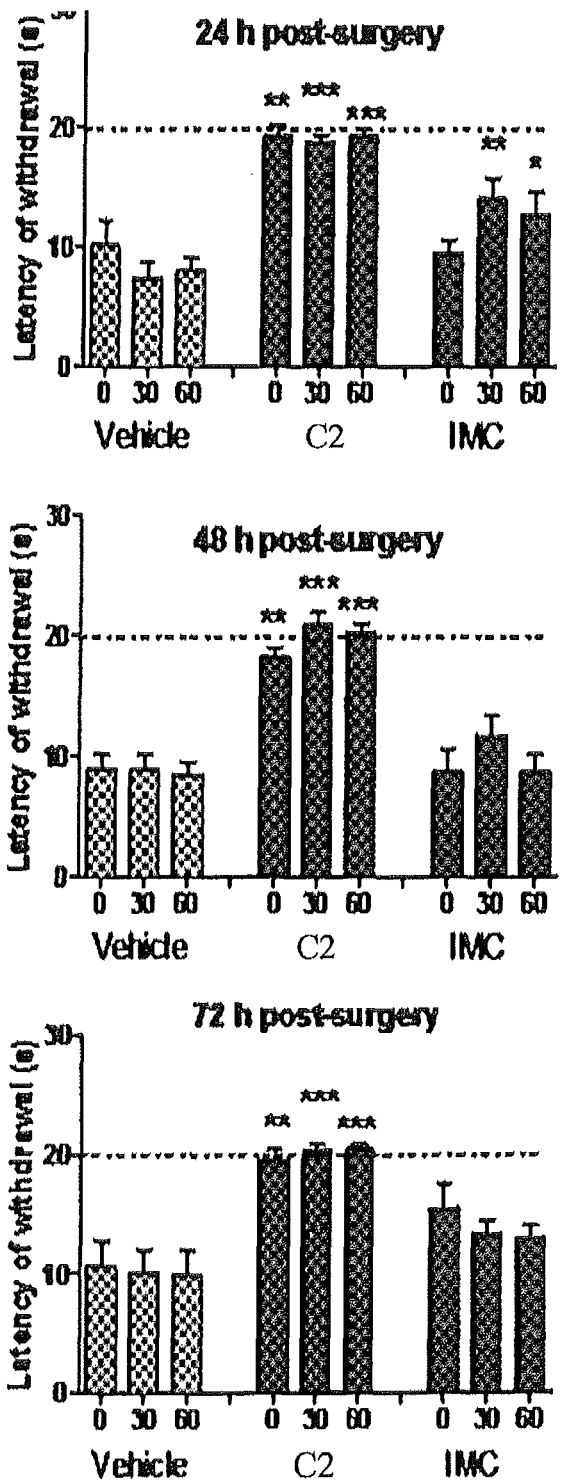
FIG. 9, comprising
Figure 9:
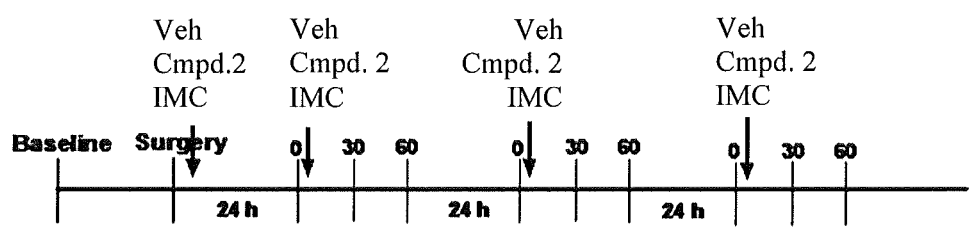

Vehicle, a reference compound (indomethacin), or compound 2 was given IV at the conclusion of a surgical incision and latency values were measured 24 hours later (0 timepoint) and 30 and 60 minutes thereafter. Determination of latencies was subsequently conducted 48 hours and 72 hours in the same manner (FIG. 9).

Experimental Example #12

Effect of Compound 2 on Established Incisional Hyperlagesia

Figure 10:
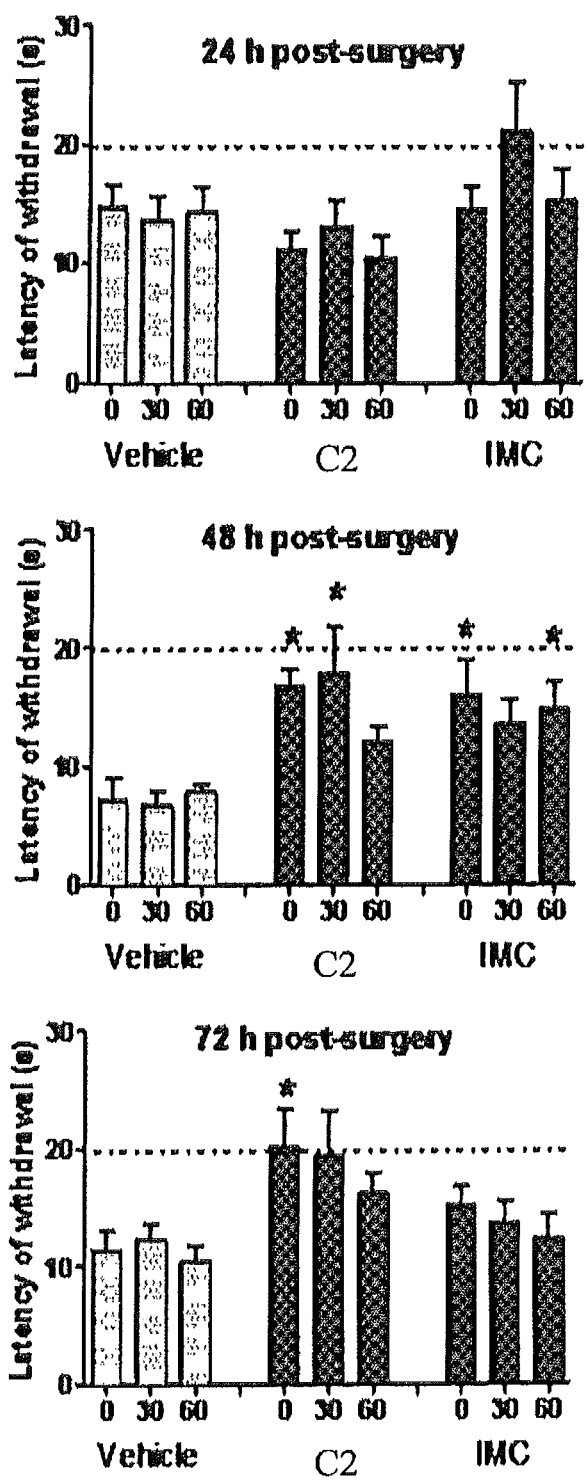
FIG. 10, comprising
Figure 10:
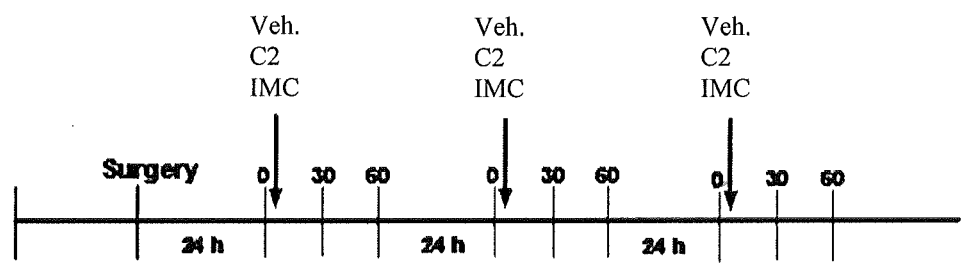

Vehicle, a reference compound (indomethacin), or compound 2 was given 24 hours after the conclusion of a surgical incision; latency values were measured 24 and 48 hours later (0 timepoint) and 30 and 60 minutes thereafter (FIG. 10). This data demonstrates that compounds of the invention can rereverse hyperalgeisa due to post-surgical pain.

Experimental Example #13

Compound 2 Inhibits Hyperalgesia Caused by SIN-1

Figure 11:
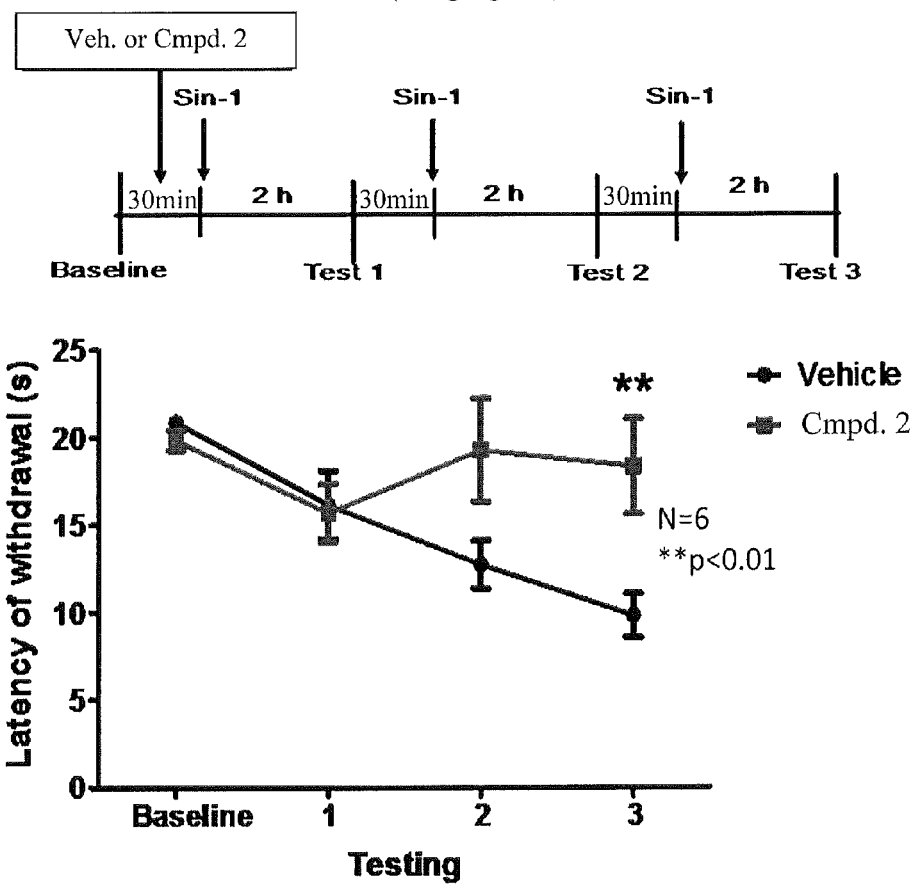
FIG. 11 depicts the results of an example experiment demonstrating that compound 2 inhibits hyperalgesia caused by SIN-1, a known producer of peroxynitrite.
Figure 12:
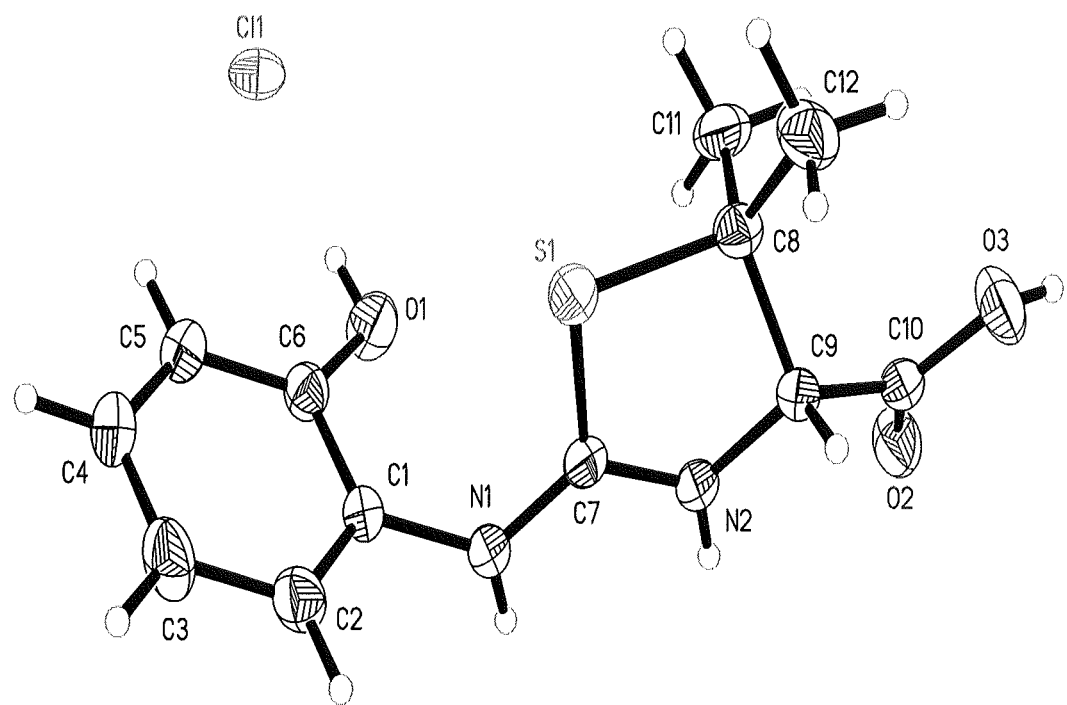
FIG. 12 is an illustration of the structure of (S)-2-(2-hydroxyphenylamino)-thiazoline-5,5-dimethyl-4-carboxylic acid hydrochloride (compound 1) as determined by crystallographic X-ray diffraction pattern analysis.
Figure 13:
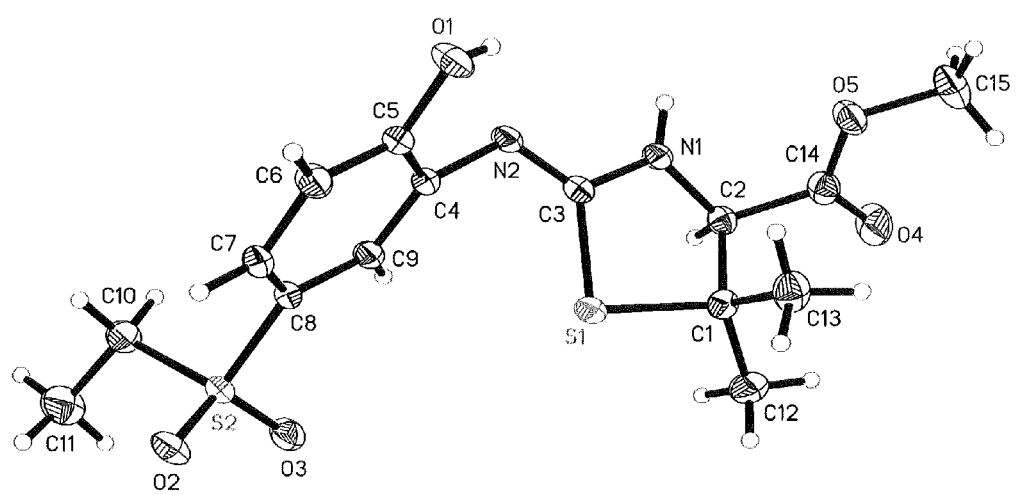
FIG. 13 is an illustration of the structure of (S)-2-(5-ethanesulfonyl-2-hydroxyphenylamino)-thiazoline-5,5-dimethyl-4-carboxylic acid methyl ester (compound 32) as determined by crystallographic X-ray diffraction pattern analysis.
Figure 14:
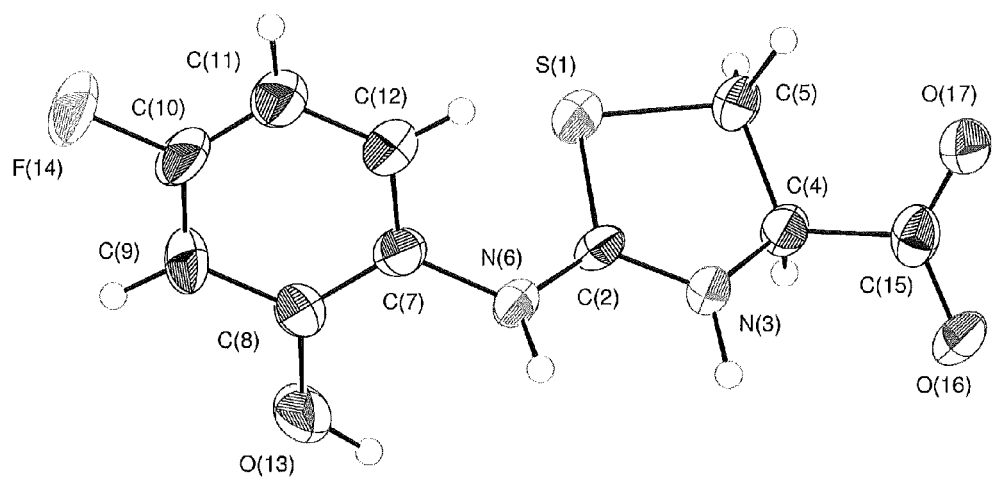
FIG. 14 is an illustration of the structure of (R)-2-(4-fluoro-2-hydroxyphenylamino)-thiazoline-4-carboxylic acid (compound 6) as determined by crystallographic X-ray diffraction pattern analysis.
Figure 15:
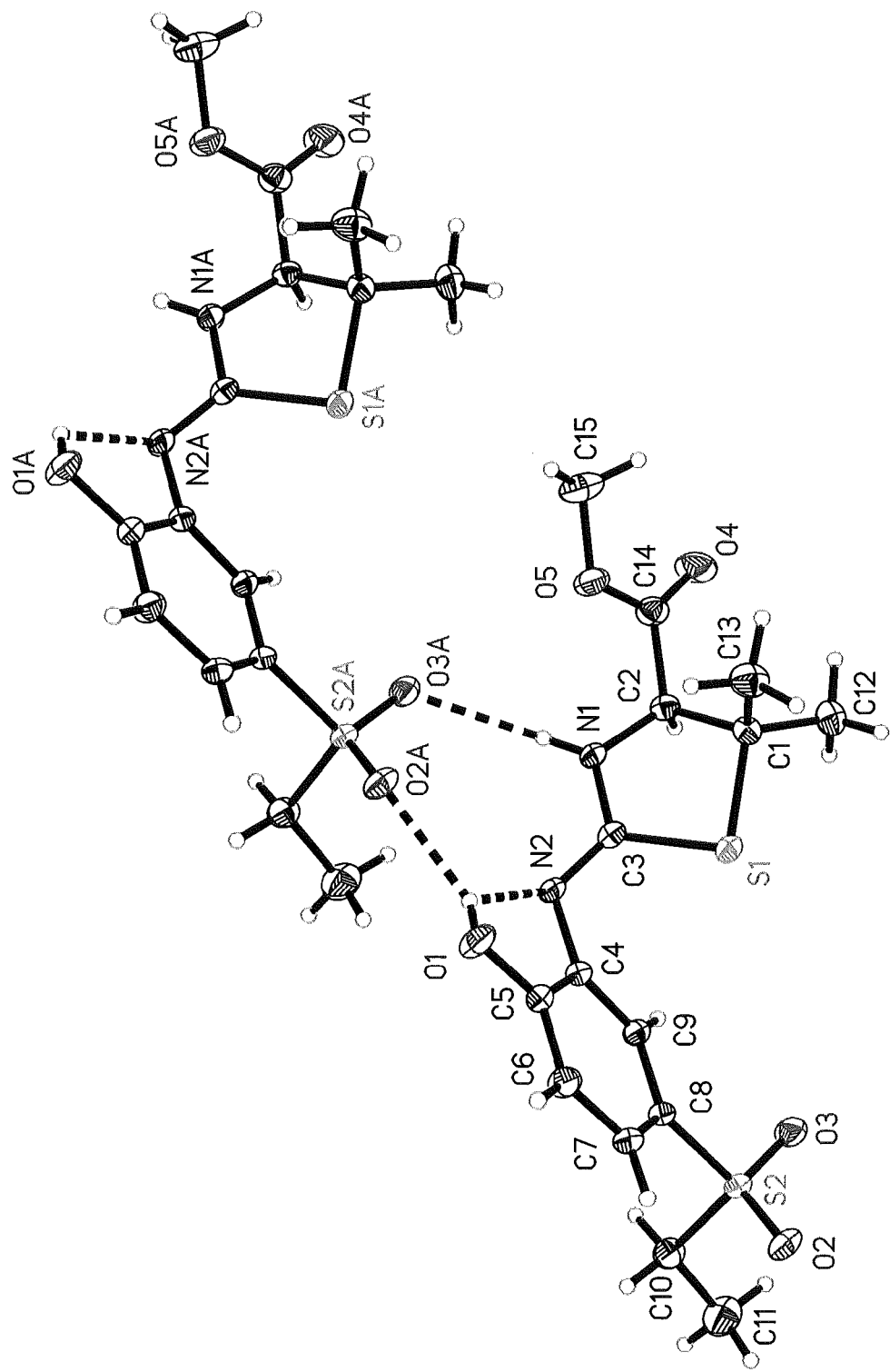
FIG. 15 is an illustration of the crystal packing structure of (S)-2-(5-ethanesulfonyl-2-hydroxyphenylamino)-thiazoline-5,5-dimethyl-4-carboxylic acid methyl ester (compound 32) as determined by crystallographic X-ray diffraction pattern analysis.

Vehicle or compound 2 was given IV 15 minutes before the first administration of SIN-1 (1 mg/kg). Latency was measured for the first time 2 hours later (Testing 1). SIN-1 (1 mg/kg) was again administered 30 minutes after Testing 1 and latency was again measured 2 hours later (Testing 2). SIN-1 (1 mg/kg) was again administered 30 minutes after Testing 2 and latency was again measured 2 hours later (Testing 3). The results, depicted in FIG. 11, demonstrate that compounds of the invention can block the development of hyperalgesia caused by SIN-1.

Experimental Example #14

Effect of Compound 2 on Opioid-Induced Toxicity

In this study, the effect of a single dose of Compound 2, administered preemptively, on fentanyl induced toxicity (death) and analgesia was evaluated. The negative control was vehicle (0.5% methyl cellulose in phosphate buffered saline). Male Sprague-Dawley Rats (Harlan, Ill.) 250-300 g at time of dosing were used.

Paw withdrawal latency to a thermal stimulus was assessed using a radiant heat source (Ugo Basile, Italy) aimed at the plantar surface of the left hind paw (Hargreaves test; Hargreaves et al., 1988, Pain 32:77-88). A cut-off latency of 40 seconds was set to avoid tissue damage. Baseline latencies were taken prior to drug administrations, and Compound 2 (25 mg/kg, i.v.) or vehicle was administered. Fifteen minutes later, the first dose of fentanyl was administered (25 µg/kg, i.v.), behavior was subsequently assessed 15 and 45 minutes post-fentanyl. Five additional fentanyl doses were administered at 60 minute intervals with behavioral assessment 15 and 45 minutes after each dose.

Statistical significance was determined on untransformed data using a two-way analysis of variance (Graphpad Prism, NC). Significant main effects were analyzed further by subsequent Bonferronni post-hoc test. The level of significance was set at $p<0.05$. Data are shown as mean±S.E.M. (with an asterisk to denote significance as compared to vehicle treated controls). The percent survival was calculated according to the following equation;

$$\% \text{ survival} = [(\text{initial } n - \text{expired } n)/(\text{initial } n)] \times 100$$

Table 3 summarizes in vivo pharmacology data. Table 4 summarizes paw withdrawal latency data, illustrated in FIG. 17. Table 5 summarizes survival (%), illustrated in FIG. 16.

TABLE 3

| Test System | Species/Strain | Method and Time of Administration | Doses (units) | Gender and No. per Group | Noteworthy Findings |
|---|---|---|---|---|---|
| Fentanyl induced toxicity (Survival) | Rat/SD | i.v. | Compound 2 single 25 mg/kg (preemptively) Fentanyl 25 µg/kg (hourly for 6 h) | M, n = 6 (initial) | Compound 2 significantly reduced death attributable to fentanyl |
| Fentanyl induced toxicity (Hargreaves) | Rat/SD | i.v. | Compound 2 single 25 mg/kg (preemptively) Fentanyl 25 µg/kg (hourly for 6 h) | M, n = 6 (initial) | Compound 2 significantly preserved analgesic efficacy of fentanyl |

TABLE 4

Paw withdrawal latency.

| | vehicle | vehicle | vehicle | vehicle | vehicle | vehicle | Cpd 2 | Cpd 2 | Cpd 2 | Cpd 2 | Cpd 2 | Cpd 2 |
|---|---|---|---|---|---|---|---|---|---|---|---|---|
| baseline | 20.12 | 16.64 | 21.7 | 19 | 20.1 | 17.98 | 19.3 | 17.01 | 21.3 | 20.3 | 17.6 | 19.03 |
| 15 | 40 | 40 | 40 | 40 | 40 | 40 | 40 | 40 | 40 | 40 | 40 | 40 |
| 45 | 37.8 | 40 | 40 | 38.9 | 37.2 | 40 | 40 | 39.2 | 40 | 37.8 | 39 | 40 |
| 75 | 40 | 40 | 40 | 40 | 40 | 40 | 40 | 40 | 40 | 40 | 40 | 40 |

TABLE 4-continued

Paw withdrawal latency.

| | vehicle | vehicle | vehicle | vehicle | vehicle | vehicle | Cpd 2 | Cpd 2 | Cpd 2 | Cpd 2 | Cpd 2 | Cpd 2 |
|---|---|---|---|---|---|---|---|---|---|---|---|---|
| 105 | 25.34 | 21.78 | 24 | 23.61 | 19.67 | 21.23 | 40 | 40 | 37.52 | 38 | | 35.96 |
| 135 | 40 | 40 | | 40 | 40 | 40 | 40 | 40 | 40 | 40 | 40 | 40 |
| 165 | 18.26 | | | | 15.33 | 22.22 | | 40 | 35.63 | 34.68 | 40 | 35.33 |
| 195 | 40 | | | | 40 | 40 | | 40 | 40 | 40 | 40 | 40 |
| 225 | 16.89 | | | | 11.3 | | | 33.54 | 36.45 | 33.98 | 40 | 25.34 |
| 255 | 40 | | | | 40 | | | 40 | 40 | 40 | 40 | 40 |
| 285 | 6.78 | | | | 15.55 | | | 22.81 | 26.14 | 38.02 | 18.61 | 25.59 |
| 315 | 33.65 | | | | 40 | | | 40 | 40 | 40 | 40 | 40 |
| 345 | 7.22 | | | | | | | 25.33 | 24.78 | 36.99 | 20.78 | 25.88 |

TABLE 5

Survival (%).

| | vehicle | cpd |
|---|---|---|
| 0 h | 100 | 100 |
| 1 h | 100 | 100 |
| 2 h | 100 | 100 |
| 3 h | 50 | 83.33 |
| 4 h | 33.3 | 83.33 |
| 5 h | 33.3 | 83.33 |
| 6 h | 16.66 | 83.33 |

Over the time course of the experiment animals died due to respiratory depression or other acute toxicities associated with repeated administration of high doses of fentanyl. Compound 2 reduced the extent of death such that a significant increase in % survival was noted (FIG. 16): 1/6 animals died in the "Compound 2" group and 5/6 animals died in the vehicle treated group (the remaining animal was sacrificed moribund). This suggests Compound 2 reduces opioid induced toxicity and improves safety.

Figure 17:
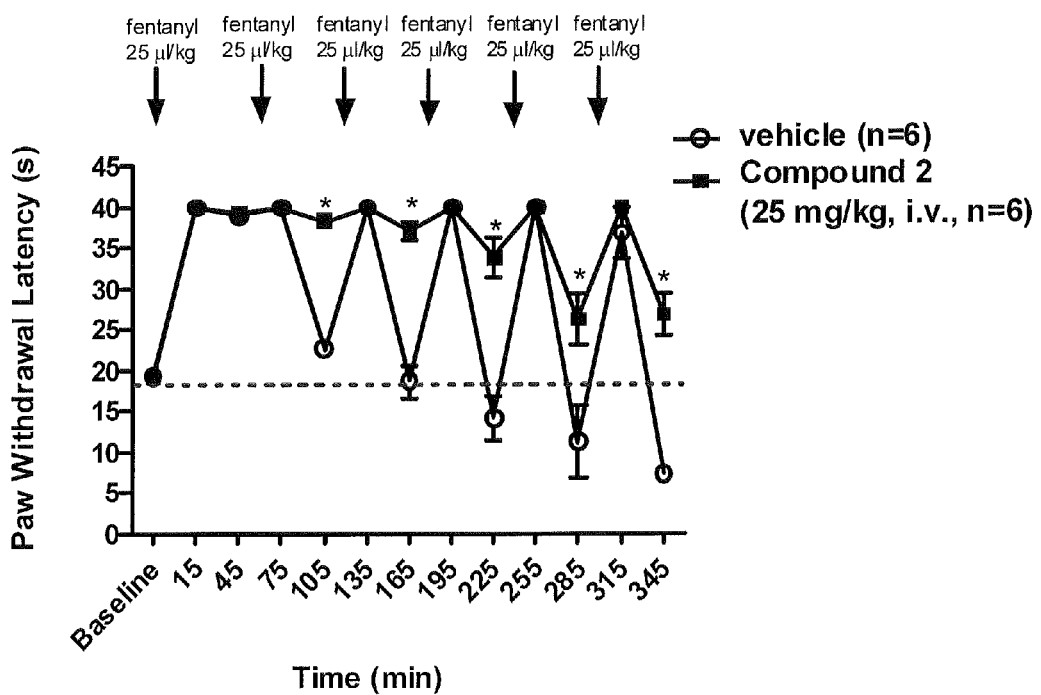
FIG. 17 is a graph illustrating the effect of preemptively dosed Compound 2, 25 mg/kg i.v., on fentanyl analgesia (6 hourly doses of 25 μg/kg i.v. fentanyl).

For the analgesia measurements, animals were baselined and Compound 2 (25 mg/kg, i.v.) was administered as a single dose 15 min prior to fentanyl (25 µg/kg, i.v.). Additional fentanyl doses were administered at 60 min intervals and behavior assessed 15 and 45 minutes after each fentanyl administration (FIG. 17).

In vehicle treated animals, fentanyl produced robust analgesia 15 minutes after each dose, but paw withdrawal latencies returned to near baseline levels by 45 minutes post-dose. Paw withdrawal latencies fell beneath baseline levels 45 minutes after the $4^{th}$, $5^{th}$ and $6^{th}$ doses of fentanyl, consistent with opioid induced hyperalgesia.

Figure 16:
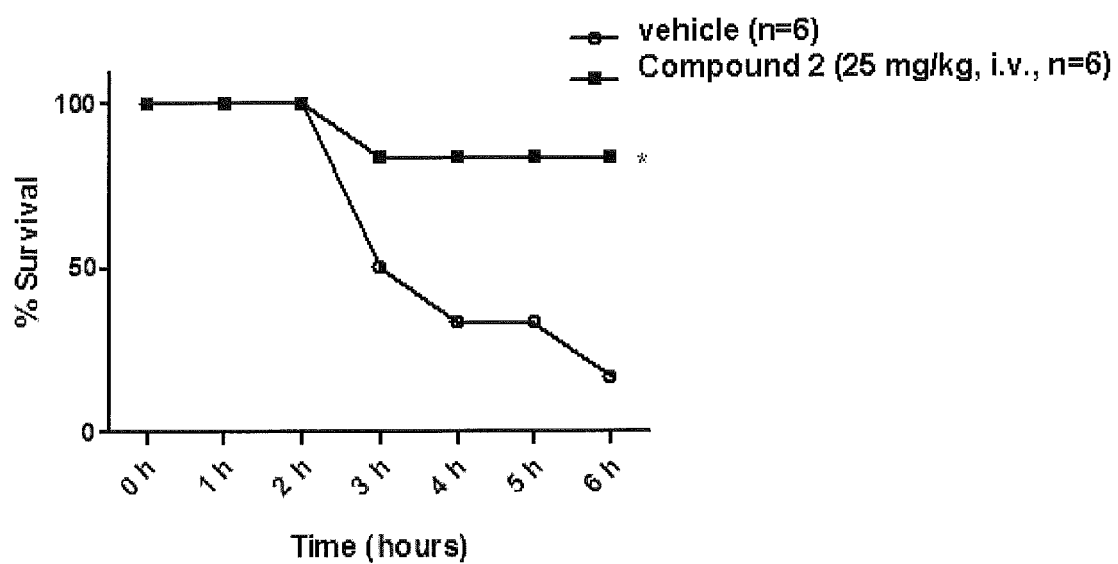
FIG. 16 is a graph illustrating the effect of a single preemptive dose of Compound 2, 25 mg/kg i.v., on fentanyl induced toxicity (6 hourly doses of 25 μg/kg i.v. fentanyl).

Compound 2 produced a statistically significant preservation of analgesic efficacy 45 minutes after dosing with fentanyl. Paw withdrawal latencies did not fall beneath baseline levels 45 minutes after the $4^{th}$, $5^{th}$ and $6^{th}$ doses of fentanyl. This suggests pretreatment with Compound 2 prevented development of opioid induced hyperalgesia (FIG. 16).

Preemptively administered Compound 2 significantly reduced deaths attributable to fentanyl. Additionally, Compound 2 (25 mg/kg, i.v.) preserved the analgesic efficacy of fentanyl and prevented the occurrence of opioid induced hyperalgesia. This data suggests that Compound 2 reduces opioid toxicity, sustains opioid analgesic efficacy and prevents opioid induced hyperalgesia. In clinical settings, Compound 2 may improve the safety profile of opioids, while simultaneously augmenting analgesia.

Experimental Example #15

Effect of Compound 2 on Thermal Hyperalgesia, Tactile Allodynia and Edema Induced by Intraplantar Freund's Complete Adjuvant Compound 2 was evaluated in the rat Freund's complete adjuvant (FCA) model of inflammatory pain. The rat Freund's complete adjuvant (FCA) intraplantar model of inflammatory pain produces behaviors similar to those observed in patients and has been widely used to assess novel pharmacological treatments (Lam et al., 2008, J Ethnopharmacol. 120: 44-50).

The positive control was celecoxib (TRC, Montreal), and the negative control was vehicle (0.5% methyl cellulose, in phosphate buffered saline). Male Sprague-Dawley Rats (Harlan, ID 250-300 g at time of dosing were used. The Hargreaves apparatus was obtained from Ugo Basile, Italy. The Freund's complete adjuvant was obtained from Sigma, St. Louis, and the electronic von frey was obtained from Stoelting, Ill.

For this assay, paw withdrawal latency to a thermal stimulus was assessed using a radiant heat source (Ugo Basile, Italy) aimed at the plantar surface of the left hind paw (Hargreaves test; Hargreaves et al., 1988, Pain 32:77-88). A cutoff latency of 40 seconds was set to avoid tissue damage. Paw withdrawal thresholds to a non-noxious tactile stimulus was assessed using an electronic von Frey apparatus that presented an increasing mechanical force to the plantar surface of the hind paw. Paw volume was measured by displacement of water and assuming a tissue density equal to that of water. Baseline latencies, thresholds and volume were taken prior to FCA injection and re-assessed 24-72 hours later. Compound 2 or vehicle was administered (25 mg/kg, i.v.; or 3-100 mg/kg, p.o.) either once immediately prior to FCA (preemptive) or 24-72 hours post-FCA (curative). When Compound 2 was administered preemptively, behavior or paw volume was assessed 24-72 hours post-dosing. When Compound 2 was administered curatively, behavior or paw volume was assessed 30-180 min post-dosing. Celecoxib (30 mg/kg p.o.) served as the positive control.

Intraplantar injection was performed under 2.5-4% isoflurane/$O_2$ anesthesia, delivered via nose cone. After induction of anesthesia, the injection site was prepared in a sterile manner and 100 µl of a 50% suspension of FCA injected. After injection, animals were weighed and allowed to recover before being returned to their home cages.

Statistical significance was determined on untransformed data using a two-way analysis of variance (Graphpad Prism, NC). Significant main effects were analyzed further by subsequent Bonferronni post-hoc test. The level of significance was set at p<0.05. Data are shown as mean±S.E.M. (with an asterisk to denote significance as compared to vehicle treated controls).

Figure 18:
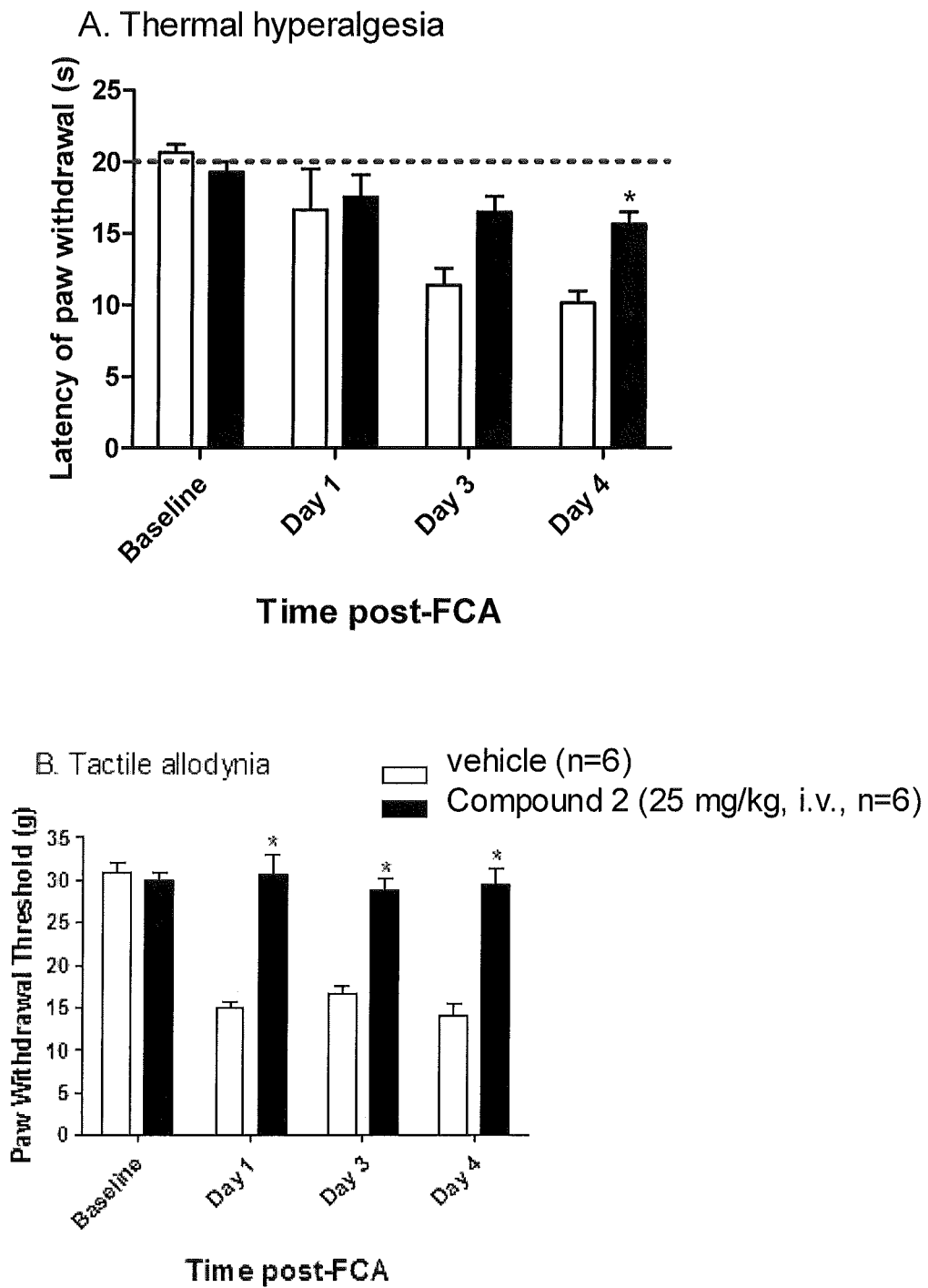
FIG. 18, comprising
Figure 19:
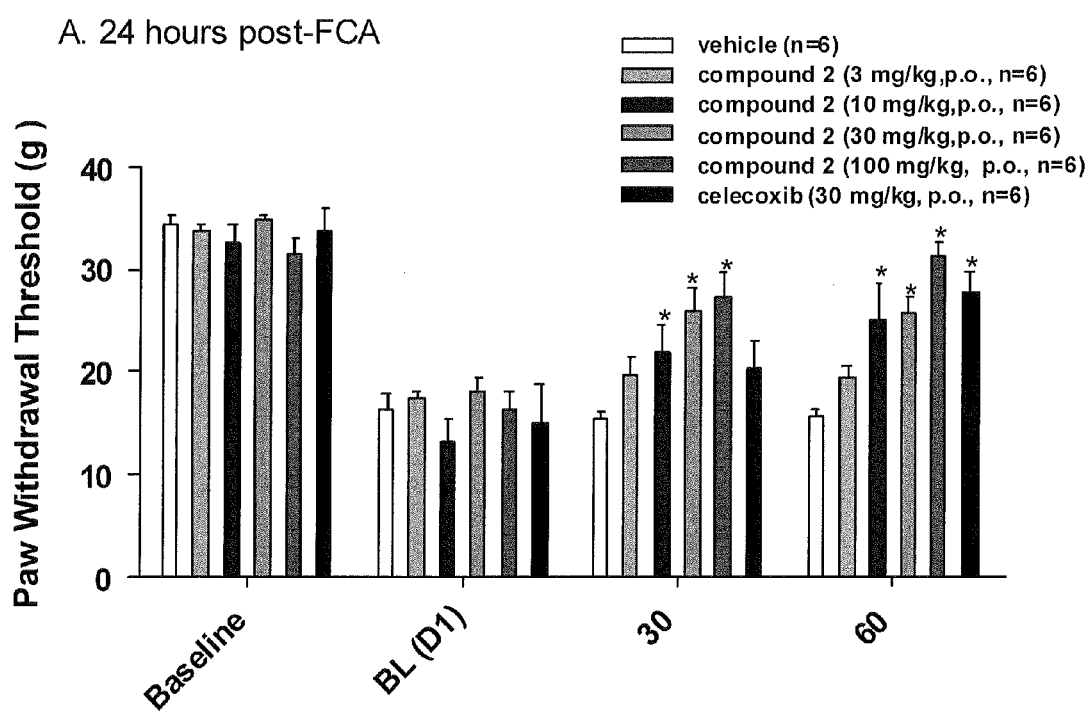
FIG. 19, comprising
Figure 19:
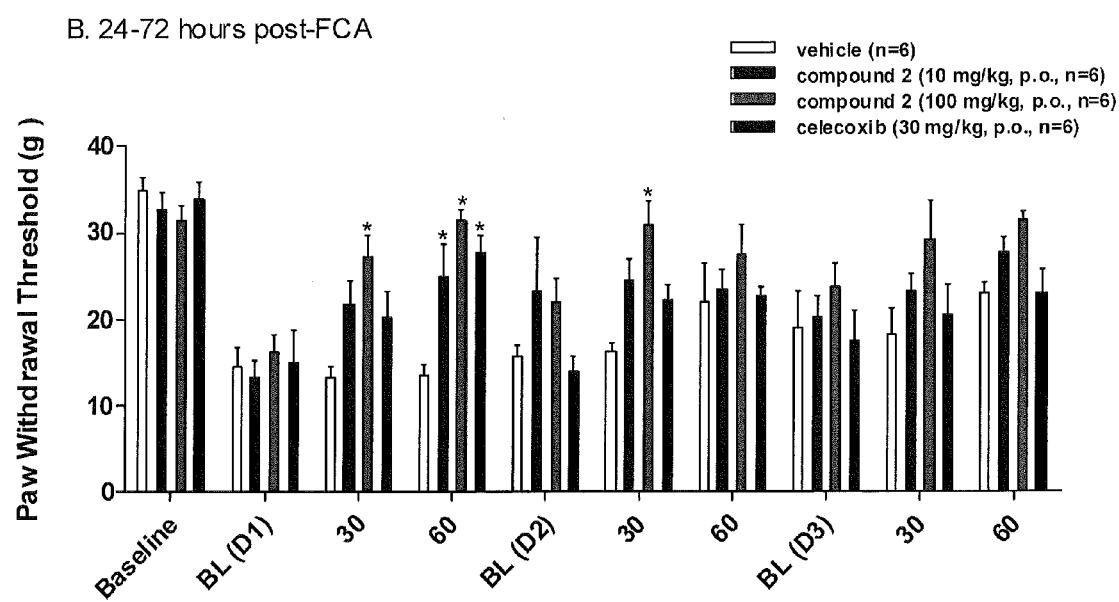
Figure 20:
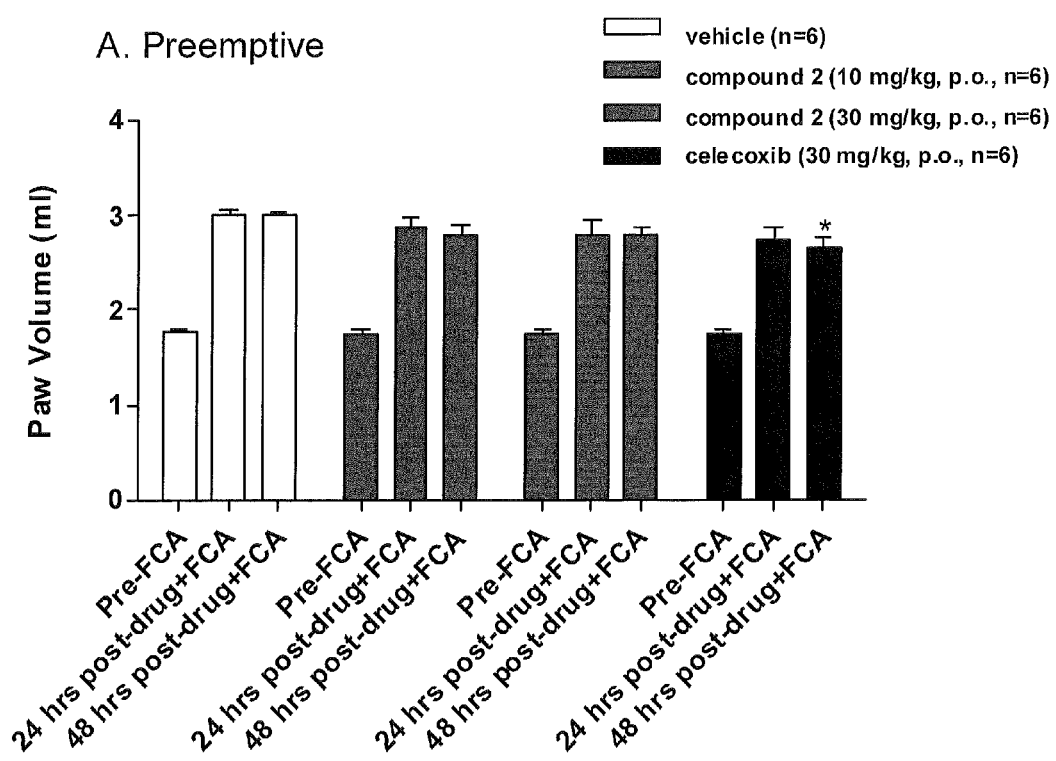
FIG. 20A and FIG. 20B, illustrates the effect of 10 and 30 mg/kg Compound 2 p.o. on FCA induced edema when dosed either preemptively or 24 hours post-FCA.
Figure 20:
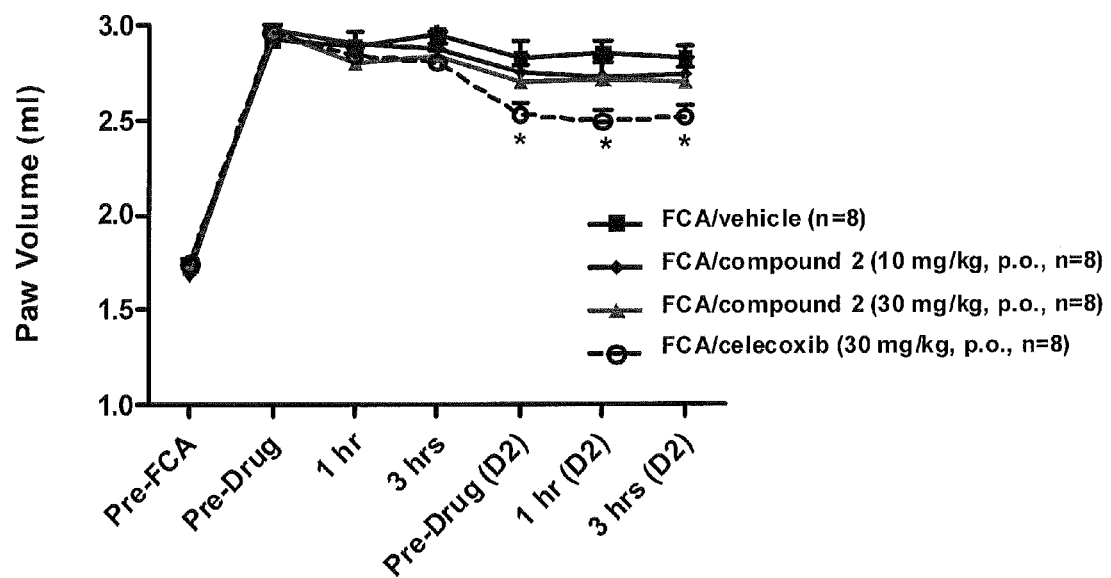

Intraplantar injection of 100 μl of FCA into the hind paw resulted in the development of thermal hyperalgesia, tactile allodynia (as assessed by electronic von Frey) and edema as indicated by a decreased latency to a noxious thermal stimulus, decreased threshold to a non-noxious tactile stimulus and increase in paw volume (FIGS. 18-20). Compound 2 (25 mg/kg, i.v.) administered preemptively prevented the development of thermal hyperalgesia (FIG. 18A) and tactile allodynia (FIG. 18B). Statistical significance, as compared to vehicle treated controls, was reached 72 hours post-FCA for thermal hyperalgesia (FIG. 18A) and 24, 48 and 72 hours post-FCA for tactile allodynia (FIG. 18B).

Table 6 summarizes the in vivo pharmacology data. Table 7 summarizes paw withdrawal latency (s), illustrated in FIG. 18A. Table 8 summarizes paw withdrawal latency (s), illustrated in FIG. 18B. Table 9 summarizes paw withdrawal threshold (g), illustrated in FIG. 19A. Table 10 summarizes paw volume (mL), illustrated in FIG. 20A. Table 11 summarizes paw volume (mL), illustrated in FIG. 20B.

TABLE 6

In vivo pharmacology data.

| Test System | Species/Strain | Method and Time of Admin. | Doses (units) | Gender and No. per Group | Noteworthy Findings |
|---|---|---|---|---|---|
| FCA induced thermal hyperalgesia and tactile allodynia | Rat/SD | i.v. | Single dose 25 mg/kg (preemptive) | M, n = 6 | Compound 2 significantly prevented FCA-thermal hyperalgesia and tactile allodynia |
| FCA induced tactile allodynia | Rat/SD | p.o. | Single dose 25 mg/kg (preemptive) | M, n = 6 | Compound 2 significantly prevented FCA-induced tactile allodynia; effect lasted for 3 days and was not reproduced by celecoxib |
| FCA induced thermal tactile allodynia | Rat/SD | p.o. | 3, 10, 30 and 100 mg/kg (curative) | M, n = 6 | Compound 2 significantly reversed FCA-induced tactile allodynia |
| FCA induced edema | Rat/SD | p.o. | 10 and 30 mg/kg (preemptive and curative) | M, n = 6 | Compound 2 did not significantly reverse FCA-induced edema |

TABLE 7

Paw withdrawal latency (s), illustrated in FIG. 18A.

|  | baseline | day 1 | day 3 | day 4 |
|---|---|---|---|---|
| vehicle | 18.72 | 16 | 12.7 | 10.66 |
| vehicle | 22.5 | 12.65 | 9.76 | 9.28 |
| vehicle | 21.2 | 12.2 | 9.16 | 9.85 |
| vehicle | 21.55 | 8.72 | 8.84 | 9.5 |
| vehicle | 19.45 | 26.63 | 11.3 | 7.73 |
| vehicle | 20.52 | 23.6 | 16.5 | 13.85 |
| compound 2 | 16.6 | 14.4 | 12.5 | 14 |
| compound 2 | 17.55 | 156.3 | 19.12 | 16.25 |
| compound 2 | 20.74 | 15.1 | 19.5 | 16.51 |
| compound 2 | 20.9 | 15.1 | 19.5 | 16.51 |
| compound 2 | 20.6 | 15.7 | 15.7 | 16.6 |
| compound 2 | 19.33 | 22.7 | 17.7 | 18.2 |

TABLE 8

Paw withdrawal latency (s), illustrated in FIG. 18B.

|  | baseline | day 1 | day 3 | day 4 |
|---|---|---|---|---|
| vehicle | 33.2 | 15.5 | 13.8 | 13.65 |
| vehicle | 32.8 | 14 | 17.5 | 9.8 |
| vehicle | 29.6 | 17.6 | 15.9 | 18.2 |
| vehicle | 31.3 | 15.1 | 20.2 | 12.8 |
| vehicle | 32.2 | 29.4 | 28.5 | 24.7 |
| vehicle | 28.1 | 12.4 | 15.4 | 15.65 |
| compound 2 | 29.6 | 36.7 | 29.8 | 25 |
| compound 2 | 32.5 | 26.7 | 28 | 27.23 |
| compound 2 | 29.8 | 38.9 | 30 | 36.5 |
| compound 2 | 27.5 | 25 | 27.7 | 31.3 |
| compound 2 | 31.4 | 27 | 23.5 | 31.9 |
| compound 2 | 29.6 | 29 | 33.8 | 24.3 |

TABLE 9

Paw withdrawl threshold (g), illustrated in FIG. 19.

|  | baseline | BL(D1) | 30 | 60 |
|---|---|---|---|---|
| vehicle | 38.27 | 17.2 | 13.1 | 15.2 |
| vehicle | 31.8 | 15.9 | 16.3 | 15.7 |
| vehicle | 37 | 20.1 | 11.3 | 13.4 |
| vehicle | 38.13 | 6.4 | 9.6 | 8.9 |
| vehicle | 31.1 | 10.1 | 13.8 | 11.2 |
| vehicle | 36.1 | 18.3 | 16.7 | 17.5 |
| vehicle | 35.4 | 22.5 | 19 | 20.1 |
| vehicle | 30.9 | 17.6 | 16.8 | 17 |
| vehicle | 33.4 | 21.4 | 20 | 19.5 |
| vehicle | 37.3 | 19.2 | 15 | 16.4 |
| vehicle | 30.4 | 10.6 | 16.8 | 15.6 |
| Compound 2 (3 mg/kg) | 36.1 | 20.5 | 22.1 | 22 |
| Compound 2 (3 mg/kg) | 32.4 | 15.3 | 16.9 | 16.5 |
| Compound 2 (3 mg/kg) | 35.8 | 18.5 | 21 | 21.4 |

TABLE 9-continued

Paw withdrawl threshold (g), illustrated in FIG. 19.

|  | baseline | BL(D1) | 30 | 60 |
|---|---|---|---|---|
| Compound 2 (3 mg/kg) | 33.4 | 16.5 | 12.6 | 15.7 |
| Compound 2 (3 mg/kg) | 34.4 | 17.3 | 27.2 | 22.3 |
| Compound 2 (3 mg/kg) | 30.9 | 15.8 | 17.5 | 18 |
| Compound 2 (10 mg/kg) | 28.6 | 8.9 | 17 | 28.2 |
| Compound 2 (10 mg/kg) | 26.67 | 12.3 | 22.2 | 25.5 |
| Compound 2 (10 mg/kg) | 37.9 | 12.3 | 22.2 | 25.5 |
| Compound 2 (10 mg/kg) | 31.3 | 8.1 | 12.6 | 12.6 |
| Compound 2 (10 mg/kg) | 39 | 22.5 | 31.6 | 36.3 |
| Compound 2 (10 mg/kg) | 31.8 | 15.1 | 25 | 30.9 |
| Compound 2 (30 mg/kg) | 33.2 | 15 | 19.3 | 24 |
| Compound 2 (30 mg/kg) | 34.9 | 19.2 | 32.6 | 24.2 |
| Compound 2 (30 mg/kg) | 36.6 | 18.2 | 27.3 | 26.5 |
| Compound 2 (30 mg/kg) | 35.6 | 22.5 | 30.2 | 21.6 |
| Compound 2 (30 mg/kg) | 34.9 | 17.8 | 26.3 | 27.4 |
| Compound 2 (30 mg/kg) | 33.4 | 16.5 | 19.5 | 31.1 |
| Compound 2 (100 mg/kg) | 31.8 | 12.8 | 28.6 | 31.2 |
| Compound 2 (100 mg/kg) | 26.6 | 13.9 | 27.9 | 27.5 |
| Compound 2 (100 mg/kg) | 27.6 | 16 | 19.3 | 35.3 |
| Compound 2 (100 mg/kg) | 33.33 | 19.3 | 34.6 | 29.1 |
| Compound 2 (100 mg/kg) | 37.8 | 23.51 | 31.6 | 30.3 |
| Compound 2 (100 mg/kg) | 31.9 | 12.6 | 21 | 34.6 |
| celecoxib (30 mg/kg) | 31.8 | 9.6 | 19.5 | 29.9 |
| celecoxib (30 mg/kg) | 39.4 | 33.6 | 24 | 32.4 |
| celecoxib (30 mg/kg) | 31.8 | 11.6 | 11.3 | 19.8 |
| celecoxib (30 mg/kg) | 25.93 | 7.4 | 18.3 | 23.2 |
| celecoxib (30 mg/kg) | 36.6 | 13.6 | 16.3 | 30.9 |
| celecoxib (30 mg/kg) | 37.73 | 13.6 | 32.1 | 29.9 |

TABLE 10

Paw volume (mL) illustrated in FIG. 20A.

|  | FCA/Vehicle | FCA/Vehicle | FCA/Vehicle | FCA/Vehicle | FCA/Vehicle | FCA/Vehicle |
|---|---|---|---|---|---|---|
| Pre-FCA | 1.8 | 1.7 | 1.8 | 1.7 | 1.7 | 1.9 |
| 24 hrs pos | 2.8 | 3 | 3.1 | 3 | 3.1 | 3.1 |
| 48 hrs pos | 2.9 | 2.9 | 3 | 3 | 3.1 | 3.1 |
| compound 2 (10 mg/kg) | | | | | | |
| | 1.7 | 1.6 | 1.8 | 1.9 | 1.8 | 1.7 |
| | 2.7 | 2.6 | 3.1 | 3.1 | 3.1 | 2.7 |
| | 2.6 | 2.5 | 2.9 | 2.9 | 3.2 | 2.6 |
| compound 2 (30 mg/kg) | | | | | | |
| | 1.6 | 1.7 | 1.9 | 1.8 | 1.7 | 1.8 |
| | 2.1 | 2.9 | 3 | 3 | 2.9 | 2.9 |
| | 2.5 | 2.8 | 3.1 | 2.8 | 2.7 | 2.9 |
| | Celecoxib | Celecoxib | Celecoxib | Celecoxib | Celecoxib | Celecoxib |
| | 1.8 | 1.9 | 1.9 | 1.7 | 1.5 | 1.7 |
| | 2.8 | 3.1 | 2.7 | 3 | 2.2 | 2.7 |
| | 2.7 | 2.7 | 2.8 | 2.8 | 2.2 | 2.8 |

TABLE 11

Paw volume (mL) illustrated in FIG. 20B.

| | FCA/Vehicle | | | | | | | |
|---|---|---|---|---|---|---|---|---|
| | FCA/Vehicle | FCA/Vehicle | FCA/Vehicle | FCA/Vehicle | FCA/Vehicle | FCA/Vehicle | FCA/Vehicle | FCA/Vehicle |
| Pre-FCA | 1.8 | 1.8 | 1.6 | 1.6 | 1.9 | 1.7 | 1.7 | 1.8 |
| Pre-Drug | 3.1 | 2.9 | 2.8 | 2.6 | 3.1 | 2.9 | 2.8 | 3.2 |
| 1 hr | 3.1 | 2.8 | 2.8 | 2.6 | 3 | 2.9 | 2.7 | 3.2 |
| 3 hrs | 3 | 3 | 2.9 | 2.6 | 3 | 3 | 2.8 | 3.3 |
| Pre-Drug (D2) | 2.9 | 3.1 | 2.9 | 2.4 | 3 | 2.5 | 2.8 | 3 |
| 1 hr (D2) | 2.9 | 3.1 | 2.9 | 2.5 | 2.9 | 2.7 | 2.8 | 3 |
| 3 hrs (D2) | 2.8 | 3.1 | 2.8 | 2.6 | 3 | 2.6 | 2.8 | 2.9 |
| | FCA/Compound 2, 10 mg/kg | | | | | | | |
| | FCA/GAL- | FCA/GAL- | FCA/GAL- | FCA/GAL- | FCA/GAL- | FCA/GAL- | FCA/GAL- | FCA/GAL- |
| Pre-FCA | 1.7 | 1.6 | 1.8 | 1.6 | 1.8 | 1.8 | 1.5 | 1.7 |
| Pre-Drug | 3.1 | 2.8 | 3.1 | 2.8 | 2.9 | 3 | 2.7 | 3.4 |
| 1 hr | 2.9 | 2.9 | 3.1 | 2.7 | 2.8 | 3 | 2.7 | 3.1 |
| 3 hrs | 2.9 | 2.9 | 3.1 | 2.7 | 2.9 | 2.9 | 2.4 | 3.2 |
| Pre-Drug (D2) | 2.7 | 2.7 | 3 | 2.6 | 2.6 | 2.8 | 2.4 | 3.2 |
| 1 hr (D2) | 2.7 | 2.7 | 2.9 | 2.7 | 2.5 | 2.8 | 2.3 | 3.2 |
| 3 hrs (D2) | 2.7 | 2.7 | 3 | 2.6 | 2.5 | 2.8 | 2.4 | 3.2 |

TABLE 11-continued

Paw volume (mL) illustrated in FIG. 20B.

| FCA/Compound 2, 30 mg/kg | | | | | | | | |
|---|---|---|---|---|---|---|---|---|
| | FCA/GAL- | FCA/GAL- | FCA/GAL- | FCA/GAL- | FCA/GAL- | FCA/GAL- | FCA/GAL- | FCA/GAL- |
| Pre-FCA | 1.7 | 1.8 | 1.5 | 1.8 | 1.7 | 1.7 | 1.9 | 1.7 |
| Pre-Drug | 2.8 | 3 | 2.9 | 3.2 | 3 | 2.6 | 3.4 | 2.8 |
| 1 hr | 2.6 | 3 | 2.8 | 2.8 | 2.9 | 2.5 | 3.1 | 2.7 |
| 3 hrs | 2.8 | 2.9 | 2.7 | 3 | 2.8 | 2.6 | 3.2 | 2.7 |
| Pre-Drug (D2) | 2.4 | 2.7 | 2.6 | 2.8 | 2.9 | 2.4 | 3.1 | 2.7 |
| 1 hr (D2) | 2.5 | 2.7 | 2.6 | 2.9 | 2.7 | 2.4 | 3.2 | 2.7 |
| 3 hrs (D2) | 2.5 | 2.7 | 2.6 | 2.8 | 2.9 | 2.4 | 3 | 2.7 |

| FCA/celecoxib, 30 mg/kg | | | | | | | | |
|---|---|---|---|---|---|---|---|---|
| | FCA/ Celecoxib | FCA/ Celecoxib | FCA/ Celecoxib | FCA/ Celecoxib | FCA/ Celecoxib | FCA/ Celecoxib | FCA/ Celecoxib | FCA/ Celecoxib |
| Pre-FCA | 1.7 | 1.7 | 1.7 | 1.8 | 1.7 | 1.9 | 1.7 | 1.7 |
| Pre-Drug | 2.8 | 3.1 | 2.8 | 2.9 | 3.1 | 3 | 3.2 | 2.8 |
| 1 hr | 2.7 | 2.9 | 2.6 | 2.7 | 3.1 | 3 | 3 | 2.7 |
| 3 hrs | 2.7 | 2.9 | 2.7 | 2.8 | 3.1 | 2.7 | 2.9 | 2.6 |
| Pre-Drug (D2) | 2.4 | 2.6 | 2.3 | 2.5 | 2.6 | 2.7 | 2.8 | 2.3 |
| 1 hr (D2) | 2.3 | 2.6 | 2.3 | 2.4 | 2.7 | 2.5 | 2.7 | 2.4 |
| 3 hrs (D2) | 2.4 | 2.5 | 2.3 | 2.5 | 2.7 | 2.6 | 2.8 | 2.3 |

When Compound 2 (3-100 mg/kg, p.o.) was administered 24 hours post-FCA, a significant reversal of FCA induced tactile allodynia was noted 30 and 60 minutes post-administration of 10, 30 and 100 mg/kg (FIG. 19). The positive control, celecoxib (30 mg/kg, p.o.) also produced a statistically significant reversal 60 minutes post-administration (FIG. 19).

Compound 2 (10 or 30 mg/kg, p.o.) did not have a statistically significant effect on FCA induced edema as measured by increase in paw volume, regardless of whether administered preemptively (FIG. 20A) or 24 hours post-FCA (FIG. 20B). In contrast, the positive control, celecoxib (30 mg/kg, p.o.), produced a statistically significant block of edema 24 and 48 hours post-administration (FIG. 20A and FIG. 20B).

These results suggest that Compound 2, by the i.v. or p.o. route of administration, may fully or partially prevent development of FCA induced tactile allodynia and thermal hyperalgesia. Importantly, in the case of tactile allodynia, this effect was maintained for at least 3 days. This effect was not seen with the same p.o. dose of celecoxib. Furthermore, Compound 2 was also able to reverse established inflammatory tactile allodynia when administered p.o., in this case producing an effect comparable to celecoxib. Finally Compound 2 did not affect edema in this model indicating that the effect on pain behavior is not secondary to an anti-inflammatory effect. The action of the celecoxib control was associated with reductions in edema. Taken together, these data suggest a clear differentiation between GAL-044 and celecoxib with respect to mechanism of action and therapeutic utility.

Experimental Example #16

Effect of Compound 2 on Thermal Hyperalgesia and Edema Induced by Intraplantar Carrageenen The effect of Compound 2 in the rat carrageenan model of acute inflammatory pain was evaluated. The intraplantar carrageenan model of acute inflammatory pain in the rat results in behaviors similar to that observed in patients and has been widely used to assess novel pharmacological treatments (Whiteside et al., 2005, J. Pharmacol. Exp. Ther. 314:1234-1240). The objective of this study was to evaluate the ability of Compound 2 to reverse or prevent development of thermal hyperalgesia and edema in the rat carrageenan model of acute inflammatory pain.

The positive control was indomethacin (Sigma, St. Louis), and the negative control was vehicle (0.5% methyl cellulose). Male Sprague-Dawley Rats (Harlan, Il) were 250-300 g at time of dosing. The Hargreaves apparatus was obtained from Ugo Basile, Italy, and the lamba-carrageenan was obtained from Sigma, St. Louis.

For this assay, paw withdrawal latency to a thermal stimulus was assessed using a radiant heat source (Ugo Basile, Italy) aimed at the plantar surface of the left hind paw (Hargreaves test). A cut-off latency of 40 seconds is set to avoid tissue damage. Paw volume was measured by displacement of water and assuming a tissue density equal to that of water. Baseline latencies were taken prior to carrageenan administration and re-assessed 4 h later. Compound 2 or vehicle was administered (10 and 30 mg/kg, p.o.) 3 hrs after carrageenan (curative) and behavior assessed 1 hr later. Additionally, Compound 2 was administered 15 minutes prior to carrageenan (preemptive) and behavior assessed 4 hours post carrageenan. Indomethacin (positive control, 30 mg/kg p.o.) was administered prior to carrageenan and behavior assessed 4 hrs post-carrageenan.

Intraplantar injection was performed under 2.5-4% isoflurane/$O_2$ anesthesia, delivered via nose cone. After induction of anesthesia, the injection site was prepared in a sterile manner and 50 µl of a 2% Jamba-carrageenan was injected. After injection, animals were weighed and allowed to recover before being returned to their home cages.

Statistical significance was determined on untransformed data using a two-way analysis of variance (Graphpad Prism, NC). Significant main effects were analyzed further by subsequent Bonferronni post-hoc test. The level of significance was set at p<0.05. Data are shown as mean±S.E.M. (with an asterisk to denote significance as compared to vehicle treated controls).

Table 12 summarizes in vivo pharmacology data. Table 13 summarizes paw withdrawal latency (s) for FIG. 21A. Table 14 summarizes paw volume (mL) for FIG. 21B. Table 15 summarizes paw withdrawal latency (s) for FIG. 22A. Table 16 summarizes paw volume (mL) for FIG. 22B.

TABLE 12

In vivo pharmacology.

| Test System | Species/Strain | Method and Time of Administration | Doses (units) | Gender and No. per Group | Noteworthy Findings |
|---|---|---|---|---|---|
| Carrageenan-induced edema | Rat/SD | p.o. | 30 mg/kg (curative) | M, n = 7-8 | Compound 2 significantly reversed carrageenan-induced edema |
| Carrageenan-induced thermal hyperalgesia/edema | Rat/SD | p.o. | 10 and 30 mg/kg (curative) | M, n = 6-7 | Compound 2 significantly reversed carrageenan-induced edema but not thermal hyperalgesia |
| Carrageenan-induced thermal hyperalgesia/edema | Rat/SD | p.o. | 10 and 30 mg/kg (preemptive) | M, n = 6 | Compound 2 did not significantly reverse carrageenan-induced thermal hyperalgesia or edema |

TABLE 13

Paw withdrawal latency (s) illustrated in FIG. 21A.

| Cg/Vehicle | Cg/Vehicle | Cg/Vehicle | Cg/Vehicle | Cg/Vehicle | Cg/Vehicle | Cg/Vehicle |
|---|---|---|---|---|---|---|
| Pre-Cg | | | | | | |
| 18.77 | 17.98 | 20.25 | 34.15 | 14.14 | 13.02 | 28.61 |
| 1 hr post-drug | | | | | | |
| 8.34 | 6.27 | 4.78 | 6.84 | 5.82 | 3.48 | 4.07 |
| compound 2 (10 mg/kg) | | | | | | |
| 19.8 | 15.34 | 22.07 | 17.39 | 31.03 | 14.07 | |
| 11.14 | 3.17 | 5.54 | 5.86 | 8.02 | 5.73 | |
| compound 2 (30 mg/kg) | | | | | | |
| 23.87 | 12.41 | 16.08 | 28.86 | 18.1 | 22.77 | 17.58 |
| 7.9 | 5.16 | 6.78 | 10.22 | 16.05 | 7.56 | 7.34 |

TABLE 14

Paw volume (mL) illustrated in FIG. 21B.

| Cg/Vehicle | Cg/Vehicle | Cg/Vehicle | Cg/Vehicle | Cg/Vehicle | Cg/Vehicle | Cg/Vehicle |
|---|---|---|---|---|---|---|
| Pre-Cg | | | | | | |
| 1.7 | 1.7 | 1.8 | 1.7 | 1.8 | 1.7 | 1.7 |
| 1 hr post-drug | | | | | | |
| 2.5 | 3 | 3.2 | 2.6 | 2.8 | 2.8 | 3.1 |
| compound 2 (10 mg/kg) | | | | | | |
| 1.7 | 1.8 | 1.8 | 1.7 | 1.6 | 1.8 | |
| 2.6 | 2.6 | 2.9 | 2.5 | 2.7 | 2.7 | |
| compound 2 (30 mg/kg) | | | | | | |
| 1.6 | 1.7 | 1.6 | 1.7 | 1.8 | 1.5 | 1.6 |
| 2.4 | 2.6 | 2.6 | 2.6 | 2.5 | 2.9 | 2.3 |

TABLE 15

Paw withdrawal latency (s) illustrated in FIG. 22A.

| Cg/Vehicle | Cg/Vehicle | Cg/Vehicle | Cg/Vehicle | Cg/Vehicle | Cg/Vehicle |
|---|---|---|---|---|---|
| 25.8 | 40 | 31.89 | 18.4 | 15.8 | 22.79 |
| 7.55 | 13.11 | 7.25 | 5.75 | 5.29 | 12.85 |
| compound 2 (10 mg/kg) | | | | | |
| 20.94 | 40 | 25.09 | 26.96 | 13.66 | 23.25 |
| 8.1 | 5.07 | 20.71 | 12.18 | 11.94 | 9.38 |
| compound 2 (30 mg/kg) | | | | | |
| 27.75 | 15.78 | 35.57 | 23.26 | 18.37 | 25.78 |
| 11.57 | 16.63 | 6.81 | 11 | 32.38 | 11.6 |
| Indo | Indo | Indo | Indo | Indo | Indo |
| 20 | 40 | 17 | 32 | 23 | 24 |
| 17 | 35 | 26 | 28 | 40 | 40 |

TABLE 16

Paw volume (mL) illustrated in FIG. 22B.

| Cg/Vehicle | Cg/Vehicle | Cg/Vehicle | Cg/Vehicle | Cg/Vehicle | Cg/Vehicle |
|---|---|---|---|---|---|
| Pre-Cg | | | | | |
| 1.8 | 1.6 | 1.8 | 1.8 | 1.7 | 1.7 |
| 4 hr post-drug | | | | | |
| 2.8 | 3.1 | 2.8 | 2.8 | 3.2 | 2.7 |
| compound 2 (10 mg/kg) | | | | | |
| 1.7 | 1.6 | 1.5 | 1.6 | 1.7 | 1.6 |
| 3.3 | 2.8 | 2.8 | 3.2 | 3.1 | 2.9 |
| compound 2 (30 mg/kg) | | | | | |
| 1.7 | 1.7 | 1.6 | 1.8 | 1.6 | 1.7 |
| 2.9 | 2.7 | 2.7 | 2.7 | 2.8 | 2.7 |
| Indo | Indo | Indo | Indo | Indo | Indo |
| 1.7 | 1.5 | 1.7 | 1.8 | 1.5 | 1.4 |
| 2.5 | 2.4 | 2.3 | 2.2 | 2.3 | 1.8 |

Figure 21:
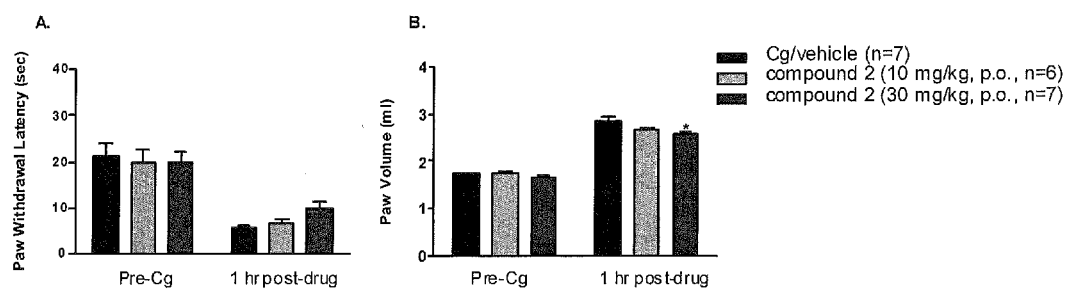
FIG. 21, comprising
Figure 22:
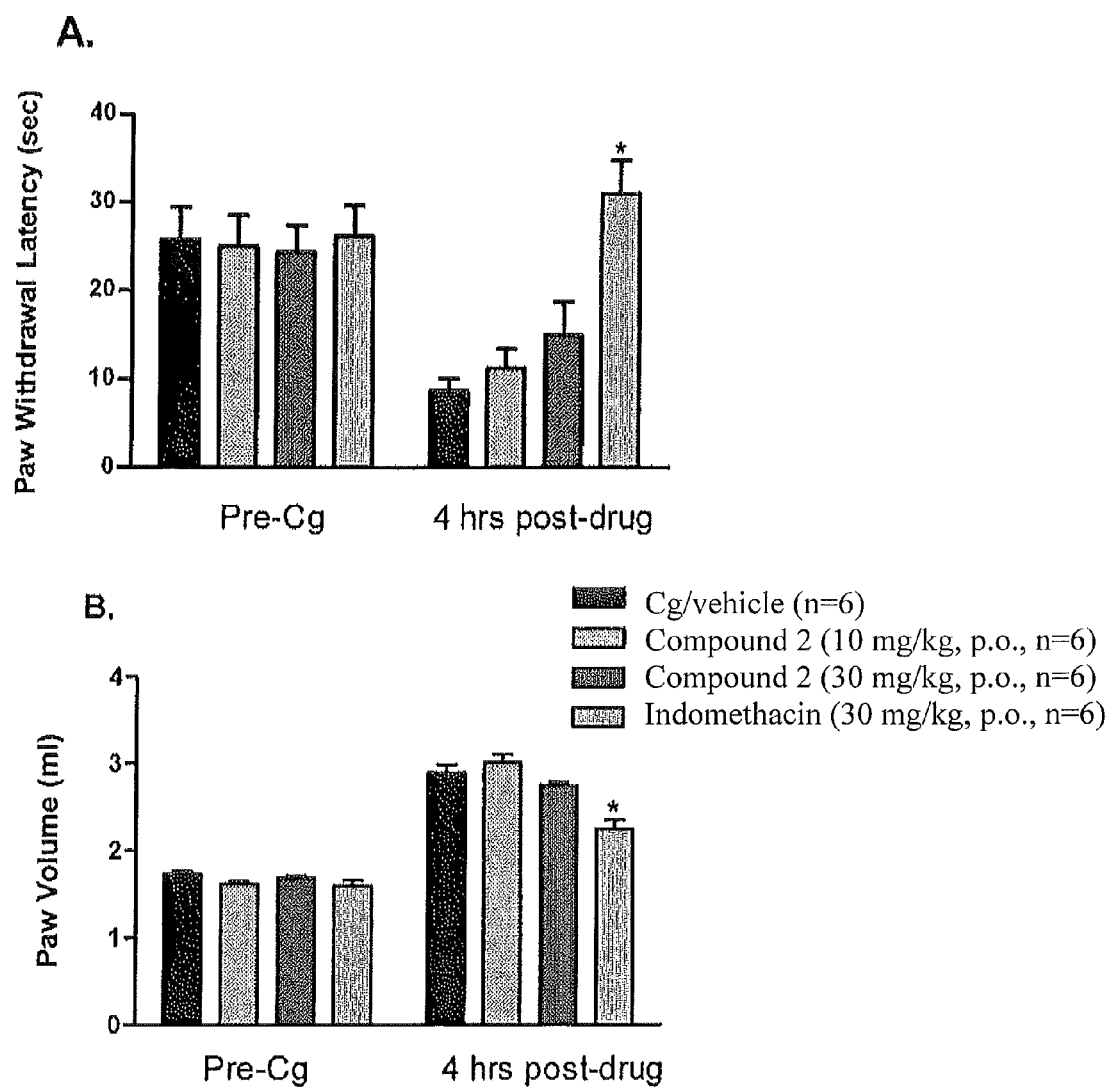
FIG. 22, comprising

Intraplantar injection of 50 μl of carrageenan into the hind paw resulted in the development of thermal hyperalgesia and edema as indicated by a decreased latency to a noxious thermal stimulus and increase in paw volume. Compound 2 (30 mg/kg, p.o.) significantly reversed edema when given as a single administration 3 hours post-carrageenan without significantly reversing thermal hyperalgesia (FIG. 21). When administered preemptively Compound 2 (10 and 30 mg/kg, p.o.) did not significantly prevent either carrageenan-induced edema or thermal hyperalgesia (FIG. 22). When dosed preemptively indomethacin (30 mg/kg p.o.), the positive control, produced a statistically significant prevention of both thermal hyperalgesia and edema (FIG. 22).

Compound 2 (30 mg/kg, p.o.) significantly reversed edema when given as a single administration 3 hours post-carrageenan but did not significantly reverse thermal hyperalgesia. When administered preemptively, a single dose of Compound 2 (10 and 30 mg/kg, p.o.) did not significantly prevent development of either carrageenan-induced edema or thermal hyperalgesia. These data suggested that preemptive Compound 2 does not prevent thermal hyperalgesia or edema caused by acute inflammation. However, when administered curatively reduces edema without significantly reducing thermal hyperalgesia.

Experimental Example #17

Effect of Compound 2 on Tactile Allodynia Induced by Spinal Nerve Ligation

Compound 2 was evaluated in the rat spinal nerve ligation (SNL) model (Chung model) of neuropathic pain. The spinal nerve ligation (SNL) model of neuropathic pain in the rat results in behaviors similar to that observed in patients (Kim and Chung, 1992, Pain 50(3):355-63) and has been widely used to assess novel pharmacological treatments (Sindrup and Jensen, 1999, Pain 83(3):389-400). Compound 2 was evaluated for its ability to reverse or prevent development of tactile allodynia in a rat model of neuropathic pain.

The positive control was gabapentin (Toronto Research Chemicals, Canada). The negative control was vehicle (0.5% methyl cellulose; 2-hydroxy-propyl-beta-cyclodextrin). Male Sprague-Dawley Rats (Harlan, Il) were 250-300 g at time of dosing. Von Frey filaments were obtained from Stoelting, Ill., and 7-0 silk, 4-0 vicryl sutures were obtained from Ethicon, NJ The surgical procedure was performed under 2.5-4% isoflurane/$O_2$ anesthesia, delivered via nose cone, and anesthesia was maintained for the duration of the surgery. After induction of anesthesia, the incision site was shaved and prepared in a sterile manner. A midline incision was performed, the L5 transverse process removed and the L5 spinal nerves tightly ligated with 7-0 silk suture material. The wound was closed in layers with 4-0 vicryl. Sham-operated control rats underwent identical procedures, however, the spinal nerve was not manipulated or ligated. After surgery, animals were weighed and allowed to recover before being returned to their home cages.

The effect of Compound 2 on nerve injury induced tactile allodynia was investigated using von Frey filaments 1-3 weeks after tight ligation of the L5 spinal nerve. Tactile thresholds were assessed using a series of calibrated von Frey monofilaments (Stoelting, Wood Dale, Ill.). Assessment of tactile allodynia was measured as the hind paw-withdrawal threshold that produced a 50% likelihood of a withdrawal using the up-down method. Thresholds were evaluated before surgery, and they were reassessed 1-3 weeks after SNL surgery. Rats were administered either a single acute dose of Compound 2 (30 mg/kg) on the day of surgery, QD (10 and 50 mg/kg) on days 1-5 post-surgery or QD (30 mg/kg) on days 1-5 post-surgery. Tactile thresholds were again assessed either 1 and 3 hrs, 3 and 5 hrs or once weekly after administration. Vehicle treated animals were included and gabapentin (100 mg/kg, i.p.) was used as the positive control. The number of animals per group was 8.

Statistical significance was determined on untransformed data using a two-way analysis of variance (Graphpad Prism, NC). Significant main effects were analyzed further by subsequent Bonferronni post-hoc test. The level of significance was set at $p<0.05$. Data are shown as mean±S.E.M.

Table 17 summarizes in vivo pharmacology data. Table 18 summarizes paw withdrawal threshold (g) illustrated in FIG. 23. Table 19 summarizes paw withdrawal threshold (g) illustrated in FIG. 24. Table 20 summarizes paw threshold (g) illustrated in FIG. 25. Table 21 summarizes paw threshold (g) illustrated in FIG. 26.

TABLE 17

In vivo pharmacology data.

| Test System | Species/ Strain | Method and Time of Administration | Doses (units) | Gender and No. per Group | Noteworthy Findings |
|---|---|---|---|---|---|
| SNL-induced tactile allodynia | Rat/SD | p.o. | 10 and 50 mg/kg | M, n = 8 | Compound 2 did not significantly reverse SNL-induced tactile allodynia |
| SNL-induced tactile allodynia | Rat/SD (fasted) | p.o. | 50 mg/kg | M, n = 8 | Compound 2 marginally (but significantly) reversed SNL-induced tactile allodynia on first day of dosing: gabapentin produced a significant reversal |
| SNL-induced tactile allodynia | Rat/SD | p.o. | 30 mg/kg | M, n = 8 | Compound 2 did not significantly affect development of SNL-induced tactile allodynia when administered once on the day of surgery |

TABLE 17-continued

In vivo pharmacology data.

| Test System | Species/Strain | Method and Time of Administration | Doses (units) | Gender and No. per Group | Noteworthy Findings |
|---|---|---|---|---|---|
| SNL-induced tactile allodynia | Rat/SD | p.o. | 30 mg/kg | M, n = 8 | On week 1 after surgery, Compound 2 significantly reduced the development of SNL-induced tactile allodynia when administered qd on days 1-5 post-surgery |

TABLE 18

Figure 23:
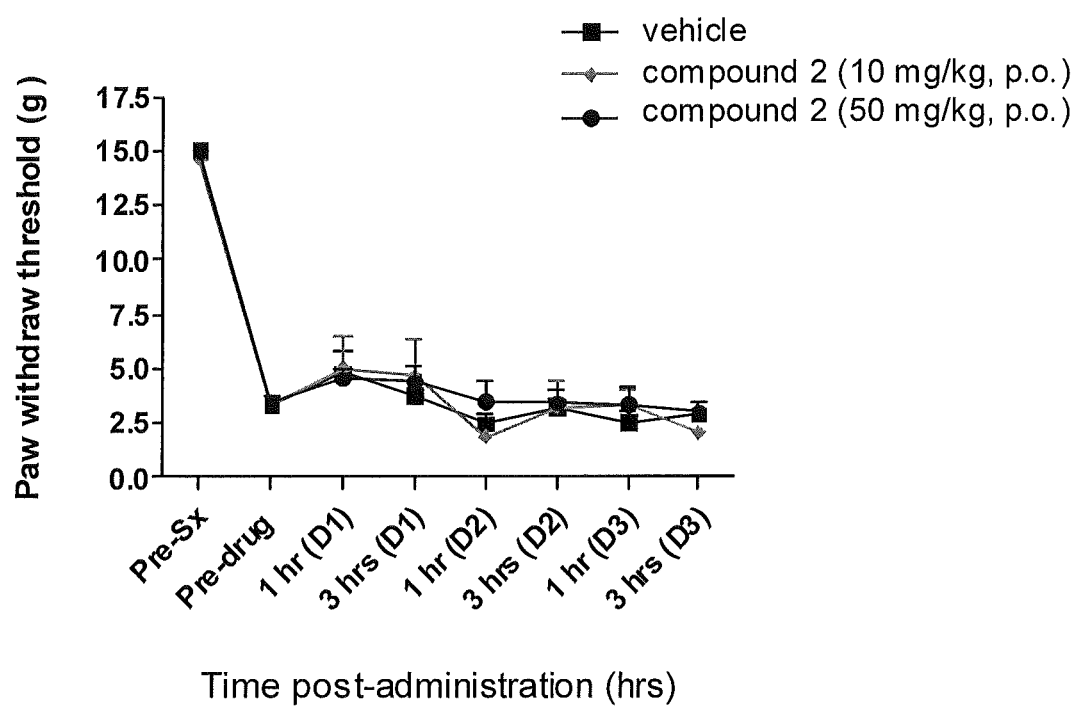
FIG. 23 is a graph illustrating the effect of 10 or 50 mg/kg Compound 2 p.o. on spinal nerve ligation induced tactile allodynia.

Paw withdrawal threshold (g) illustrated in FIG. 23.

| | Vehicle | Vehicle | Vehicle | Vehicle | Vehicle | Vehicle | Vehicle | Vehicle |
|---|---|---|---|---|---|---|---|---|
| Pre-Sx | 15 | 15 | 15 | 15 | 15 | 15 | 15 | 15 |
| Pre-Drug | 3.13 | 2.81 | 3.13 | 1.56 | 4.25 | 3.73 | 5.04 | 3.67 |
| 1 hr (D1) | 2 | 5.04 | 10.04 | 2.38 | 7.94 | 4.25 | 4.25 | 2.81 |
| 3 hrs (D1) | 1.56 | 3.67 | 10.04 | 2 | 3.58 | 3.73 | 2.81 | 2.81 |
| 1 hr (D2) | 1.4 | 1.12 | 5.04 | 3.55 | 2.37 | 2.2 | 2.81 | 1.56 |
| 3 hrs (D2) | 1.85 | 5.54 | 3.13 | 2.81 | 3.33 | 3.13 | 4.25 | 1.65 |
| 1 hr (D3) | 1.4 | 2.64 | 4.25 | 1.19 | 4.25 | 1.58 | 3.58 | 1.85 |
| 3 hrs (D3) | 1.85 | 6.66 | 3.58 | 2.2 | 2.37 | 2.2 | 2.37 | 2 |

TABLE 18-continued

Paw withdrawal threshold (g) illustrated in FIG. 23.

| compound 2 (10 mg/kg) | | | | | | | |
|---|---|---|---|---|---|---|---|
| 11.69 | 15 | 15 | 15 | 15 | 15 | 15 | 15 |
| 2.2 | 3.13 | 4.25 | 3.58 | 3.73 | 4.4 | 2.64 | 3.13 |
| 1.56 | 4.98 | 4.25 | 15 | 4.25 | 3.13 | 2.81 | 4.4 |
| 2 | 7.94 | 1.4 | 15 | 2.81 | 2.64 | 1.85 | 3.57 |
| 1.31 | 1.85 | 1.85 | 2.38 | 1.85 | 2.64 | 1.65 | 1.4 |
| 0.4 | 1.56 | 1.56 | 11.69 | 2.81 | 2.37 | 2 | 3.71 |
| 0.44 | 3.67 | 1.85 | 7.94 | 3.33 | 2 | 2.81 | 4.4 |
| 0.99 | 2.37 | 1.56 | 2.38 | 2.81 | 0.65 | 3.33 | 2.81 |

| compound 2 (50 mg/kg) | | | | | | | |
|---|---|---|---|---|---|---|---|
| 15 | 15 | 15 | 15 | 15 | 15 | 15 | 15 |
| 2.81 | 3.33 | 3.73 | 2.81 | 2.2 | 5.04 | 4.25 | 3.58 |
| 2.81 | 6.64 | 2.81 | 5.56 | 3.67 | 5.56 | 4.23 | 4.98 |
| 1.18 | 3.13 | 3.33 | 6.66 | 6.64 | 6.66 | 3.13 | 4.7 |
| 1.19 | 2.81 | 3.12 | 7.94 | 2.81 | 6.66 | 1.18 | 2.37 |
| 1.65 | 4.47 | 2.81 | 3.58 | 2.65 | 6.58 | 2.81 | 3.33 |
| 0.78 | 6.58 | 3.67 | 4.72 | 2.81 | 5.57 | 1.85 | 1.19 |
| 1.18 | 1.85 | 5.57 | 2.81 | 1.85 | 4.72 | 3.13 | 3.13 |

TABLE 19

Figure 24:
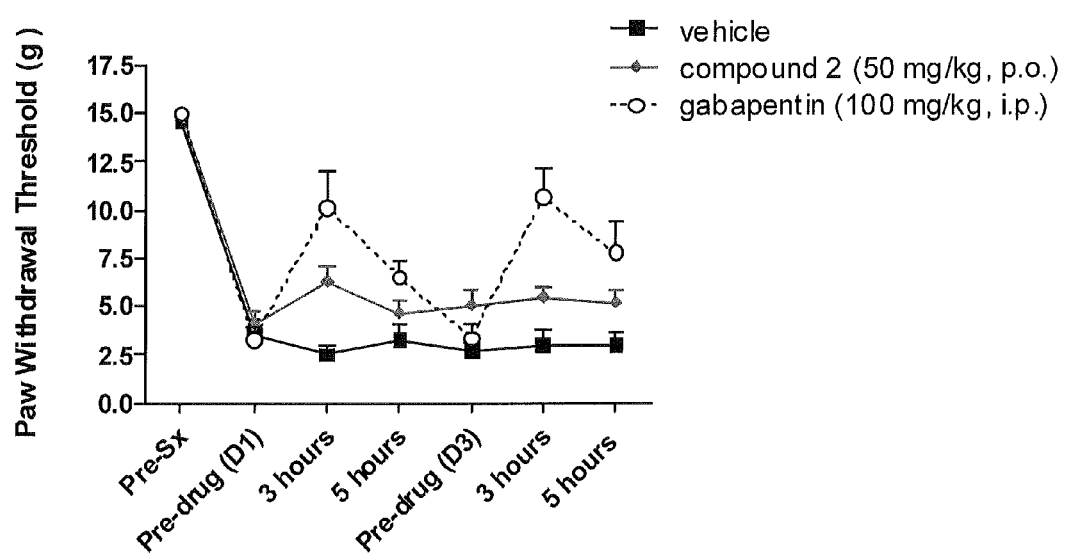
FIG. 24 is a graph illustrating the effect of 50 mg/kg Compound 2 p.o. on spinal nerve ligation induced tactile allodynia.

Paw withdrawal threshold (g) illustrated in FIG. 24.

| | Vehicle | Vehicle | Vehicle | Vehicle | Vehicle | Vehicle | Vehicle | Vehicle |
|---|---|---|---|---|---|---|---|---|
| Pre-Sx | 15 | 11.69 | 15 | 15 | 15 | 15 | 15 | 15 |
| Pre-Drug (D1) | 7.8 | 0.65 | 2.38 | 1.58 | 2.81 | 4.98 | 4.25 | 3.67 |
| 3 hrs | 5.56 | 1.19 | 2.37 | 0.99 | 2.2 | 1.85 | 2.81 | 3.13 |
| 5 hrs | 3.73 | 1.4 | 3.33 | 2.37 | 1.56 | 2.37 | 8.44 | 2.81 |
| Pre-Drug (D3) | 3.67 | 0.99 | 2.2 | 3.73 | 1.85 | 3.58 | 1.85 | 3.73 |
| 3 hrs | 4.25 | 1.65 | 7.94 | 2.38 | 1.99 | 1.65 | 2.37 | 1.65 |
| 5 hrs | 6.58 | 0.44 | 2.2 | 3.13 | 3.33 | 1.85 | 4.25 | 2.2 |

| compound 2 | | | | | | | |
|---|---|---|---|---|---|---|---|
| 15 | 15 | 15 | 15 | 15 | 15 | 15 | 15 |
| 6.58 | 4.4 | 2.75 | 1.4 | 2.81 | 5.04 | 1.18 | 2.81 |
| 4.23 | 10.04 | 6.64 | 3.13 | 6.64 | 5.04 | 1.56 | 5.04 |
| 5.04 | 7.31 | 3.55 | 1.85 | 3.72 | 5.04 | 3.67 | 3.13 |
| 4.25 | 8.44 | 2.81 | 1.4 | 4.98 | 6.4 | 2 | 3.33 |
| 6.58 | 6.58 | 4.47 | 3.13 | 6.58 | 4.25 | 3.67 | 4.4 |
| 2.81 | 4.25 | 6.66 | 1.85 | 6.64 | 4.25 | 2.81 | 6.64 |

| Gabapentin | Gabapentin | Gabapentin | Gabapentin | Gabapentin | Gabapentin | Gabapentin | Gabapentin |
|---|---|---|---|---|---|---|---|
| 15 | 15 | 15 | 15 | 15 | 15 | 15 | 15 |
| 6.64 | 1.65 | 1.33 | 1.56 | 2.81 | 4.23 | 5.04 | 2.81 |
| 15 | 5.18 | 15 | 3.67 | 15 | 15 | 6.58 | 5.56 |
| 10.31 | 5.56 | 6.58 | 1.99 | 6.66 | 7.94 | 6.4 | 6.58 |

TABLE 19-continued

Paw withdrawal threshold (g) illustrated in FIG. 24.

| 6.64 | 1.56 | 1.4  | 1.65 | 5.57  | 3.55 | 3.58 | 2.81 |
| 15   | 15   | 15   | 3.33 | 11.69 | 8.61 | 6.58 | 9.86 |
| 15   | 4.4  | 4.72 | 2.37 | 6.58  | 15   | 7.31 | 6.66 |

TABLE 20

Figure 25:
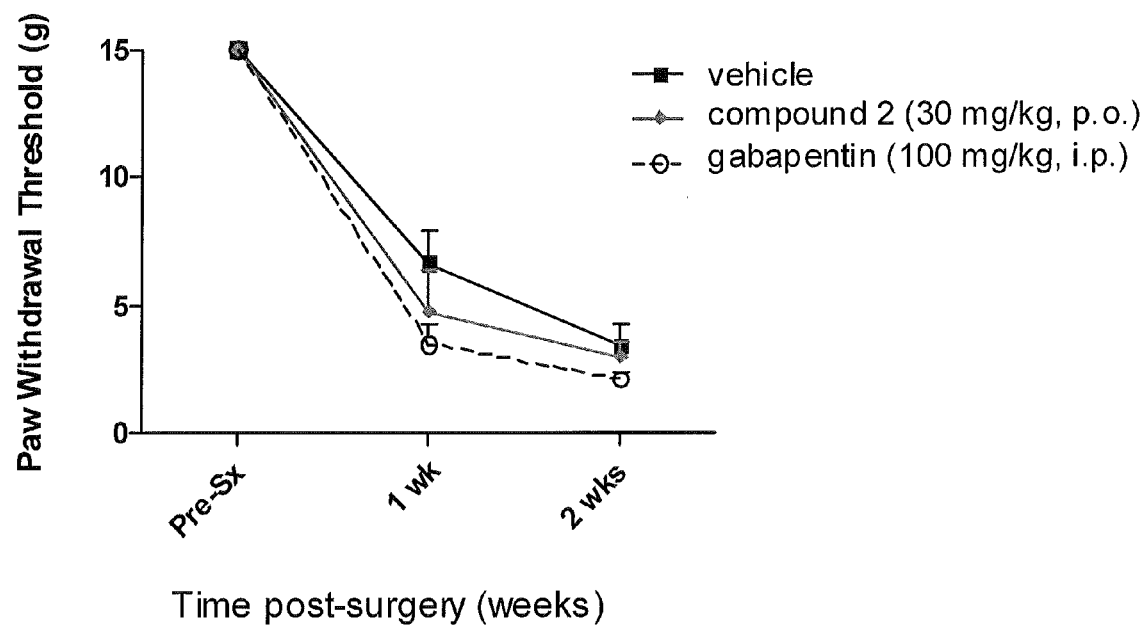
FIG. 25 is a graph illustrating the effect of dosing of single dose (day 1) 30 mg/kg Compound 2 p.o. on spinal nerve ligation induced tactile allodynia.

Paw threshold (g) illustrated in FIG. 25.

|  | Vehicle | Vehicle | Vehicle | Vehicle | Vehicle | Vehicle | Vehicle | Vehicle |
|---|---|---|---|---|---|---|---|---|
| Pre-Sx | 15 | 15 | 15 | 15 | 15 | 15 | 15 | 15 |
| 1 wk | 6.42 | 4.25 | 3.33 | 4.25 | 5.57 | 5.37 | 9.86 | 13.96 |
| 2 wks | 6.66 | 4.25 | 0.4 | 1.85 | 2.81 | 2.2 | 2.81 | 6.42 |

| compound 2 | | | | | | | | |
|---|---|---|---|---|---|---|---|---|
| 15 | 15 | 15 | 15 | 15 | 15 | 15 | 15 |
| 1.85 | 1.18 | 2.81 | 4.47 | 6.4 | 2.2 | 15 | 4.25 |
| 1.65 | 2.81 | 2 | 2 | 3.73 | 0.99 | 5.56 | 5.04 |

| Gabapentin | Gabapentin | Gabapentin | Gabapentin | Gabapentin | Gabapentin | Gabapentin | Gabapentin |
|---|---|---|---|---|---|---|---|
| 15 | 15 | 15 | 15 | 15 | 15 | 15 | 15 |
| 1.56 | 1.56 | 6.58 | 3.73 | 2.2 | 6.58 | 4.25 | 1.4 |
| 0.99 | 1.31 | 3.13 | 1.4 | 2.81 | 2.81 | 1.4 | 2.81 |

TABLE 21

Figure 26:
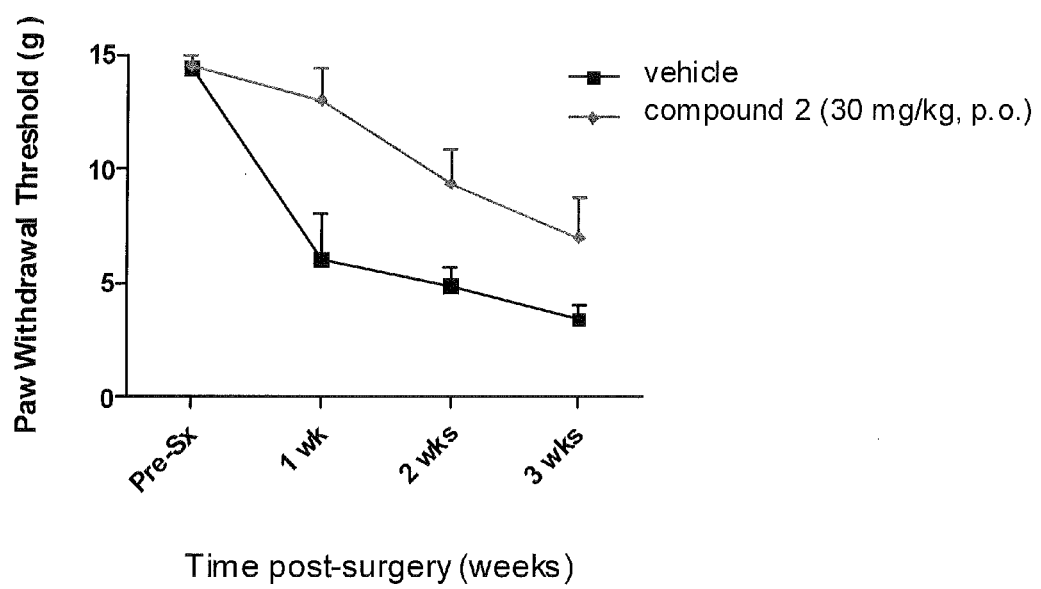
FIG. 26 is a graph illustrating the effect of repeated QD dosing (days 1-5) of 30 mg/kg Compound 2 p.o. on spinal nerve ligation induced tactile allodynia.

Paw threshold (g) illustrated in FIG. 26.

|  | Vehicle | Vehicle | Vehicle | Vehicle | Vehicle | Vehicle | Vehicle | Vehicle |
|---|---|---|---|---|---|---|---|---|
| Pre-Sx | 15 | 15 | 11.69 | 15 | 15 | 15 | 15 | 15 |
| 1 wk | 15 | 1.85 | 3.33 | 5.56 | 15 | 15 | 6.66 | 4.25 |
| 2 wks | 7.94 | 3.33 | 6.64 | 6.66 | 6.42 | 15 | 3.67 | 2.81 |
| 3 wks | 15 | 4.25 | 2.2 | 2.2 | 2.64 | 6.66 | 2.81 | 3.13 |

| compound 2 | | | | | | | | |
|---|---|---|---|---|---|---|---|---|
| 15 | 15 | 15 | 15 | 15 | 11.69 | 15 | 15 |
| 15 | 11.41 | 15 | 3.13 | 1.18 | 15 | 6.66 | 15 |
| 13.96 | 4.25 | 5.37 | 11.69 | 2.8 | 8.44 | 7.94 | 13.96 |
| 7.53 | 6.64 | 4.98 | 2.2 | 4.4 | 2.38 | 10.31 | 15 |

Spinal nerve ligation resulted in the development of tactile allodynia as indicated by a decreased paw withdrawal threshold to a non-noxious tactile mechanical stimulus, 3 to 4 weeks post-surgery (FIGS. 23-26). Using non-fasted animals, Compound 2 (10 and 50 mg/kg, p.o.) did not produce a statistically significant difference from vehicle treated animals at any time point after any of the three administrations (FIG. 23). In separate experiments, gabapentin (100 mg/kg i.p.), the positive control, consistently produced a statistically significant reversal of allodynia (e.g. FIG. 24)

In a follow up study using animals fasted overnight prior to compound administration, Compound 2 (50 mg/kg, p.o.) produced statistically significant dose- and time dependent reversal of allodynia 3 hr post dosing upon first administration. However the magnitude of the effect was small (FIG. 24), and upon subsequent administrations (48 hrs later) Compound 2 failed to produce a statistically significant effect. In contrast, gabapentin (100 mg/kg, i.p.), the positive control, produced a statistically significant reversal of hyperalgesia 3 and 5 hours after each administration.

When Compound 2 (30 mg/kg, p.o.) was given as a single administration immediately following the surgery and behaviorally assessed 1 and 2 weeks later a significant difference between treated animals and vehicle controls was not noted. Gabapentin when dosed on only the day of surgery also failed to alter the course of development of allodynia (FIG. 25). In contrast, when Compound 2 (30 mg/kg, p.o.) was administered repeatedly, once a day for 5 days starting on the day of surgery, a significant reduction in tactile allodynia was noticed 1, 2 and 3 weeks post surgery (FIG. 26).

Overall, Compound 2 (50 mg/kg, p.o.) failed to produce robust and significant reversal of tactile allodynia when given as a single administration 3 weeks post-surgery. In contrast, when given repeatedly during the development of allodynia (QD, days 1-5 post-surgery, 30 mg/kg, p.o.) Compound 2 caused a significant reduction in tactile allodynia as compared to vehicle treated controls. These data suggested that Compound 2 does not have acute efficacy in the treatment of established neuropathic pain. However, it may affect the time course and/or magnitude of allodynia during the development phase, i.e., Compound 2 may delay onset or reduce incidence or severity of neuropathic pain.

Experimental Example #18

Effect of Compound 2 on Latency to Fall in an Accelerating Rotarod Assay of Ataxia Compound 2 was evaluated in a rat accelerating rotarod model of ataxia. Ataxia is a common clinical problem with CNS-active compounds and can often confound interpretation of efficacy in preclinical pain models. The rotarod assay of ataxia has been widely used to assess the side-effect liability of novel pharmacological treatments (Jones & Roberts, 1968, J. Pharm. Pharmacol. 20:302-04). The effect of Compound 2 on latency to fall in an accelerating rotarod assay of ataxia in rats was evaluated. In one aspect, the data could be used to establish a therapeutic index for Compound 2 vs. ataxia/sedation.

The positive control was haloperidol (Sigma, St. Louis), and the negative control was vehicle (which was HPMethyl-Cellulose for Compound 2; and 15% DMA, 65% PEG300, and 20% D5W for haloperidol). Male Sprague-Dawley Rats (Harlan, Ill.) were 250-300 g at time of dosing. Rotarod was obtained from IITC, CA.

To examine the potential effects of Compound 2 on motor performance, rats were tested on an accelerating rotarod (IITC, Ca). In this assay, rats were placed on the rotarod with the speed set to accelerate from 4 to 40 rpm over 300 seconds. The maximum time spent on the rotarod was set at 300 seconds. Rats received two timed training trials (averaged to give the reported baseline) on the first day, then 24 hr later rats were administered Compound 2 (30, 100 and 300 mg/kg, p.o.), haloperidol (3 mg/kg, p.o.), the positive control, or vehicle. Latency to fall was assessed 1 hr post-drug administration corresponding to the $T_{max}$ for Compound 2 in rats when given orally.

Statistical significance was determined on untransformed data using a two-way analysis of variance (Graphpad Prism, NC). Significant main effects were analyzed further by subsequent Bonferronni post-hoc test. The level of significance was set at $p<0.05$. Data are shown as mean±S.E.M. (with an asterisk to denote significance as compared to vehicle treated controls).

Table 22 summarizes the in vivo pharmacology data. Table 23 summarizes the latency to fall data illustrated in FIG. 27.

TABLE 22

In vivo pharmacology data.

| Test System | Species/Strain | Method and Time of Administration | Doses (units) | Gender and No. per Group | Noteworthy Findings |
|---|---|---|---|---|---|
| Rotarod | Rat/SD | p.o. | 30, 100, 300 mg/kg | M, n = 11-12 | Compound 2 did not significantly reduce latency to fall |

TABLE 23

Figure 27:
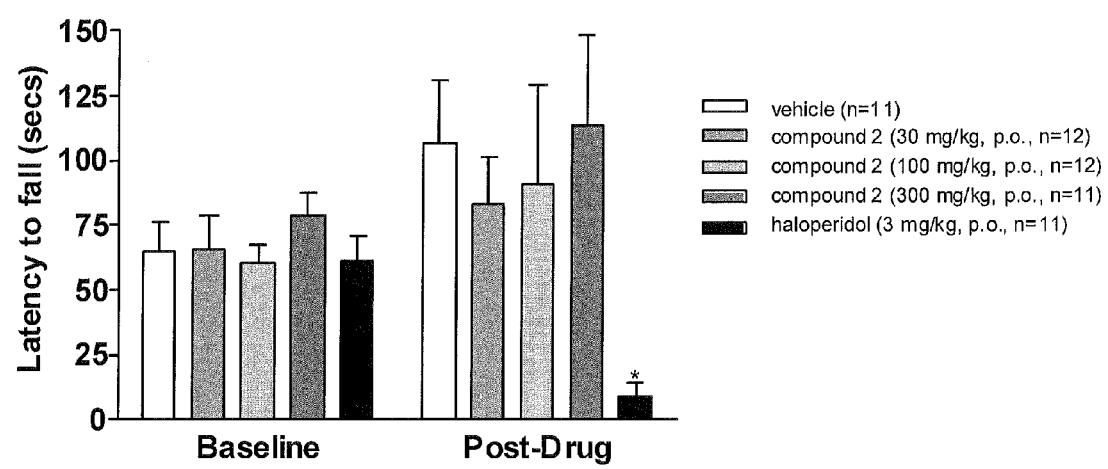
FIG. 27 is a bar graph illustrating the effect of 30, 100 and 300 mg/kg Compound 2 p.o. on latency to fall in the accelerating rotarod assay of ataxia.

Latency to fall (sec) illustrated in FIG. 27.

| | Vehicle | Vehicle | Vehicle | Vehicle | Vehicle | Vehicle | Vehicle | Vehicle |
|---|---|---|---|---|---|---|---|---|
| Baseline | 44.5 | 51.5 | 69 | 64.5 | 50.5 | 62 | 72 | 78.5 |
| Post-Drug | 37 | 127 | 118 | 89 | 87 | 91 | 179 | 140 |

| | compound 2 (300 mg/kg) | | | | | | | |
|---|---|---|---|---|---|---|---|---|
| Baseline | 84 | 76.5 | 57 | 86.5 | 81.5 | 79 | 71.5 | 86.5 |
| Post-Drug | 184 | 55 | 112 | 55 | 105 | 184 | 124 | 175 |

| | Vehicle | Vehicle | Vehicle | compound 2 (30 mg/kg) | | | | |
|---|---|---|---|---|---|---|---|---|
| Baseline | 105.5 | 46 | 64 | 70 | 108.5 | 72 | 68 | |
| Post-Drug | 118 | 105 | 80 | 39 | 99 | 72 | 94 | |

| | compound 2 (300 mg/kg) | | | Haloperidol | Haloperidol | Haloperidol | Haloperidol | |
|---|---|---|---|---|---|---|---|---|
| Baseline | 61 | 97.5 | 89 | 60 | 38 | 42.5 | 59 | |
| Post-Drug | 43 | 131 | 78 | 9 | 10 | 7 | 2 | |

| | compound 2 (30 mg/kg) | | | | | | | |
|---|---|---|---|---|---|---|---|---|
| Baseline | 52 | 49 | 60.5 | 48.5 | 47.5 | 68 | 47.5 | 97 |
| Post-Drug | 66 | 81 | 133 | 120 | 56 | 115 | 50 | 70 |

| | Haloperidol | Haloperidol | Haloperidol | Haloperidol | Haloperidol | Haloperidol | Haloperidol 3 mg/kg |
|---|---|---|---|---|---|---|---|
| Baseline | 68 | 48 | 86 | 62 | 71 | 80 | 57 |
| Post-Drug | 5 | 5 | 6 | 2 | 30 | 10 | 15 |

| | compound 2 (100 mg/kg) | | | | | | |
|---|---|---|---|---|---|---|---|
| Baseline | | 43.5 | 75.5 | 55 | 63 | 60.5 | 73.5 |
| Post-Drug | | 86 | 64 | 45 | 111 | 91 | 221 |
| Baseline | | | | | | | |
| Post-Drug | | | | | | | |

TABLE 23-continued

Latency to fall (sec) illustrated in FIG. 27.

| | compound 2 (100 mg/kg) | | | | | |
|---|---|---|---|---|---|---|
| Baseline | 73 | 72 | 54.5 | 54 | 46.5 | 53 |
| Post-Drug | 72 | 45 | 66 | 20 | 72 | 199 |
| Baseline | | | | | | |
| Post-Drug | | | | | | |

Latency to fall increased in all groups between baseline and post-drug effects; performance improves with repeated runs on the rotarod. Compound 2 (30, 100 and 300 mg/kg, p.o.) did not significantly decrease latency to fall in the rotarod assay at 1 hr post-dosing as compared to vehicle treated animals. In contrast, haloperidol (3 mg/kg, p.o.), the positive control, resulted in significant motor deficits 1 h post-administration (FIG. 27).

The present study evaluated Compound 2 in an rat accelerating rotarod assay, a model of ataxia and sedation. Compound 2 (30-300 mg/kg, p.o.) did not significantly reduce latency to fall 1 hr post-dosing. In contrast, haloperidol (3 mg/kg, p.o.) produced a substantial reduction in latency. These data suggested that high doses of Compound 2 did not cause ataxia in rats. This in turn suggested that efficacy signals seen across multiple pain models were not due to confounding ataxia and sedation. The data also suggested that Compound 2 did not cause ataxia and sedation clinically. This is consistent with Compound 2 having limited CNS penetration, and suggested that the primary site of action for the analgesic effects of GAL-044 may be in the periphery.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound according to Formula I or a salt thereof:

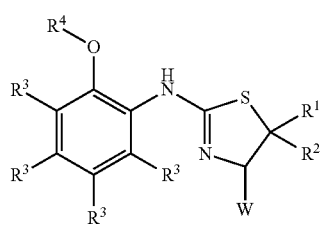

Formula I wherein in Formula I:

$R^1$ and $R^2$ are independently hydrogen or alkyl, or $R^1$ and $R^2$ form together a radical according to the formula $(CH_2)_n$, wherein n is selected from the group consisting of 2, 3, 4, 5 and 6;

$R^3$ is, independently at each occurrence, hydrogen, alkyl, substituted alkyl, alkenyl, alkynyl, halogen, phenyl, substituted phenyl, aryl, substituted aryl, heteroaryl, substituted heteroaryl, hydroxyl, alkoxy, cyano, nitro, acyl, carboxy, carboxyalkyl, or amido;

$R^4$ is hydrogen, alkyl, substituted alkyl, or acyl; and

W is carboxy, or carboxyalkyl.

2. The compound of claim 1, wherein $R^1$ and $R^2$ are $CH_3$.

3. A compound selected from the group consisting of (S)-2-(2-hydroxyphenylamino)-thiazoline-5,5-dimethyl-4-carboxylic acid, (R)-2-(2-hydroxyphenylamino)-thiazoline-5,5-dimethyl-4-carboxylic acid, (R)-2-(2-Hydroxy-4-methoxyphenylamino)-thiazoline-4-carboxylic acid, (R)-2-(4-Fluoro-2-hydroxyphenylamino)-thiazoline-4-carboxylic acid, (R)-2-(3,5-Dichloro-2-hydroxy-4-methylphenylamino)-thiazoline-4-carboxylic acid, (R)-2-(5-tert-Butyl-2-hydroxyphenylamino)-thiazoline-4-carboxylic acid, (R)-2-(2-Hydroxy-4-methoxycarbonylphenylamino)-thiazoline-4-carboxylic acid, (R)-2-(5-Ethanesulfonyl-2-hydroxyphenylamino)-thiazoline-4-carboxylic acid, (R)-2-(4-Chloro-2-hydroxyphenylamino)-thiazoline-4-carboxylic acid, (R)-2-(2-Hydroxy-5-methoxyphenylamino)-thiazoline-4-carboxylic acid, (S)-2-(2-Hydroxy-5-chlorophenylamino)-thiazoline-5,5-dimethyl-4-carboxylic acid methyl ester, (S)-2-(2-Hydroxy-5-chlorophenylamino)-thiazoline-5,5-dimethyl-4-carboxylic acid, (S)-2-(2-Hydroxy-5-methylphenylamino)-thiazoline-5,5-dimethyl-4-carboxylic acid methyl ester, (S)-2-(2-Hydroxy-5-methylphenylamino)-thiazoline-5,5-dimethyl-4-carboxylic acid, (S)-2-(2-Hydroxy-4-methoxyphenylamino)-thiazoline-5,5-dimethyl-4-carboxylic acid, (S)-2-(2-Hydroxy-4-methoxyphenylamino)-thiazoline-5,5-dimethyl-4-carboxylic acid methyl ester, (S)-2-(4-Chloro-2-hydroxyphenylamino)-thiazoline-5,5-dimethyl-4-carboxylic acid, (S)-2-(2-Hydroxy-5-nitrophenylamino)-thiazoline-5,5-dimethyl-4-carboxylic acid methyl ester, (S)-2-(2-Hydroxy-5-nitrophenylamino)-thiazoline-5,5-dimethyl-4-carboxylic acid, (S)-2-(5-Ethanesulfonyl-2-hydroxyphenylamino)-thiazoline-5,5-dimethyl-4-carboxylic acid methyl ester, (S)-2-(5-Ethanesulfonyl-2-hydroxyphenylamino)-thiazoline-5,5-dimethyl-4-carboxylic acid, (R)-2-(2-hydroxyphenylamino)-thiazoline-4-carboxylic acid methyl ester, (S)-2-(2-hydroxyphenylamino)-thiazoline-5,5-dimethyl-4-carboxylic acid methyl ester, (R)-2-(4-chloro-2-hydroxyphenylamino)-thiazoline-4-carboxylic acid methyl ester, (S)-2-(4-chloro-2-hydroxyphenylamino)-thiazoline-5,5-dimethyl-4-carboxylic acid methyl ester, (R)-2-(4-chloro-2-hydroxyphenylamino)-thiazoline-4-carboxylic acid, and (R)-2-(2-hydroxyphenylamino)-thiazoline-5,5-dimethyl-4-carboxylic acid methyl ester, mixtures thereof and salts thereof.

* * * * *